(12) United States Patent
Takemiya et al.

(10) Patent No.: US 7,994,196 B2
(45) Date of Patent: Aug. 9, 2011

(54) INDAZOLE COMPOUND AND PHARMACEUTICAL USE THEREOF

(75) Inventors: Akihiro Takemiya, Tokyo (JP); Masahiro Nakajo, Tokyo (JP); Hisae Oshima, Tokyo (JP); Tomotaka Yanagi, Tokyo (JP); Mami Mochizuki, Tokyo (JP); Hideo Nakamura, Tokyo (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 1175 days.

(21) Appl. No.: 10/589,130

(22) PCT Filed: Feb. 10, 2005

(86) PCT No.: PCT/JP2005/001996
§ 371 (c)(1),
(2), (4) Date: Jan. 16, 2007

(87) PCT Pub. No.: WO2005/077912
PCT Pub. Date: Aug. 25, 2005

(65) Prior Publication Data
US 2007/0173537 A1    Jul. 26, 2007

(30) Foreign Application Priority Data
Feb. 12, 2004   (JP) .................................. 2004-035565

(51) Int. Cl.
*A61K 31/445* (2006.01)
*C07D 401/12* (2006.01)
(52) U.S. Cl. ....................................... 514/322; 546/199
(58) Field of Classification Search .................. 514/322; 546/199
See application file for complete search history.

(56) References Cited

U.S. PATENT DOCUMENTS

| 6,949,579 B2 * | 9/2005 | Dutruc-Rosset et al. ..... 514/403 |
| 7,166,629 B2 * | 1/2007 | Lesuisse et al. ............. 514/397 |
| 7,528,155 B2 * | 5/2009 | Zoller et al. .................. 514/322 |
| 7,632,854 B2 * | 12/2009 | Martina et al. ................ 514/403 |
| 2008/0312226 A1 | 12/2008 | Matsumoto et al. |

FOREIGN PATENT DOCUMENTS

| EP | 1 813 606 A1 | 8/2007 |
| WO | 03 028720 | 4/2003 |
| WO | 03 035005 | 5/2003 |
| WO | 03 064397 | 8/2003 |
| WO | 03 078403 | 9/2003 |
| WO | 03 097610 | 11/2003 |

OTHER PUBLICATIONS

Seddon "Pseudopolymorph . . . " Crystal growth & design 496) 1087 (2004) (two pages form internet).*
Braga et al. "Making crystals from . . . " J. Royal Soc. chem. Chem. Connun. p. 3635-3645 (2005).*
Office Action issued Oct. 14, 2010, in German Patent Application No. 05 710 048.9-1211.

* cited by examiner

*Primary Examiner* — Celia Chang
(74) *Attorney, Agent, or Firm* — Oblon, Spivak, McClelland, Maier & Neustadt, L.L.P.

(57) ABSTRACT

The present invention can provide a cancer treatment drug containing, as an active ingredient, a substance selected from the group consisting of an indazole compound of the following formula (I), a pharmaceutically acceptable salt, a hydrate, a water adduct and a solvate:

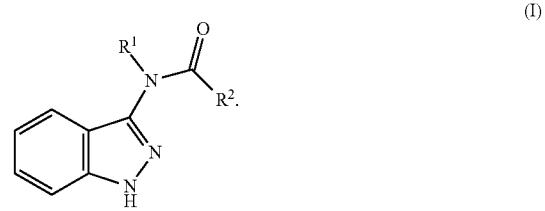

16 Claims, No Drawings

INDAZOLE COMPOUND AND PHARMACEUTICAL USE THEREOF

TECHNICAL FIELD

The present invention relates to novel indazole compounds and pharmaceutical agents comprising the compound as an active ingredient.

BACKGROUND ART

Conventional cancer treatment drugs such as 5-fluorouracil (5-FU), cisplatin and so on are associated with a problem of high expression rate of side effects. Therefore, the development of pharmaceutical agents that selectively act on the cancer cells has been ongoing, and imatinib (Glivec (trademark)), trastuzumab (Herceptin (trademark)) and so on have been placed on the market. All of these drugs target proteins that are specifically expressed in cancer cells. As to other cancer treatment drugs, the development of angiogenesis inhibitors that suppress angiogenesis necessary for the survival and metastasis of tumors has been currently undertaken. Angiogenesis inhibitors are pharmaceutical agents that show an anti-tumor effect by directly acting on the vascular endothelial cells around cancer cells, and indirectly acting on the cancer cells. Accordingly, reduction of side effects and different anti-tumor spectra are expected unlike the existing pharmaceutical agents.

As angiogenesis inhibitors, various pharmaceutical agents such as MMP (matrix metalloproteinase) inhibitors, anti-VEGF (vascular endothelial growth factor) antibodies, VEGF receptor tyrosine kinase inhibitors (VEGFR-TK inhibitors) and so on have been developed.

NF-$_\kappa$B is a transcription factor present in the cytoplasm, which is activated in response to the stimulation by IL-1, TNF-$_\alpha$ and so on. As the gene products of NF-$_\kappa$B, MMP, IL-8 and so on involved in angiogenesis, and Cyclin D and so on involved in cell growth are known. In addition, NF-$_\kappa$B is known to express Bcl-2 and so on, thereby inducing apoptosis resistance of the cells. Furthermore, constitutive activation of NF-$_\kappa$B in cancer cells has been reported, and NF-$_\kappa$B is considered to constitute one of the factors supporting the properties of cancer cells, such as apoptosis resistance, metastasis via new blood vessels and so on.

It is considered that suppression of the activation of NF-$_\kappa$B having such properties and inhibition of the production of the gene product thereof will provide a promising effect of removing the apoptosis resistance of cancer cells and suppressing of angiogenesis, and that a novel angiogenesis inhibitor directly acting on cancer cells can be developed.

In the meantime, there are a number of indazole compounds synthesized to the present. However, the compounds described in WO03035005 (patent reference 1) are not known to have an anti-tumor activity, and the compounds described in WO03097610 (patent reference 2) and WO03028720 (patent reference 3) have an inhibitory action of protein kinase.

patent reference 1: WO03/035005
patent reference 2: WO03/097610
patent reference 3: WO03/028720

DISCLOSURE OF THE INVENTION

Problems to be Solved by the Invention

An object of the present invention is to provide a novel indazole compound having an antiangiogenic action and an anticancer action, and useful as a cancer treatment drug.

Means of Solving the Problems

The present inventors have conducted intensive studies in an attempt to solve the aforementioned problems and found that indazole compounds represented by the following formula (I), pharmaceutically acceptable salts, hydrates, water adducts and solvates thereof show an inhibitory effect of MMP-9 production and have a potent antiangiogenic action and a potent anticancer action. The present invention has been completed based on the above-mentioned findings.

Accordingly, the present invention provides the following.
(1) An indazole compound represented by the following formula (I):

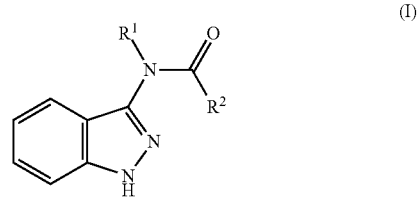

wherein
$R^1$ is a hydrogen atom, an optionally substituted alkyl, an optionally substituted phenyl or an optionally substituted aromatic heterocyclic ring, and
$R^2$ is any of the following formula (II) to the following formula (VII),

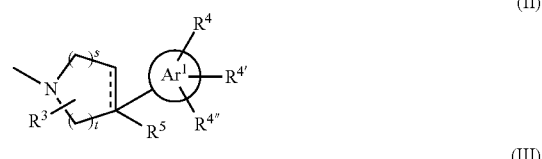

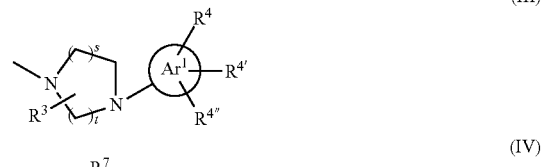

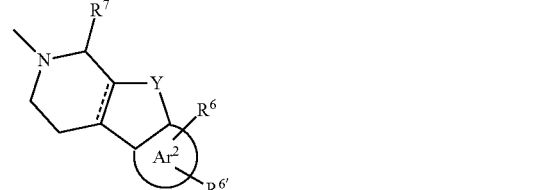

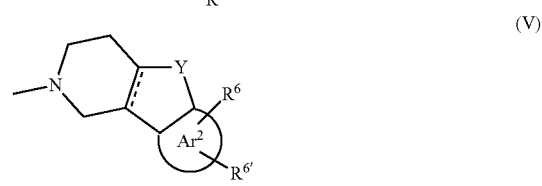

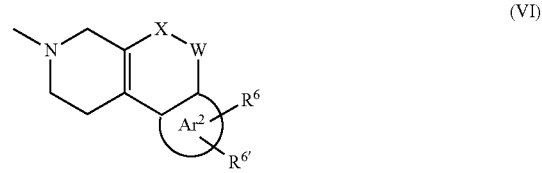

(VII)

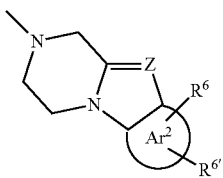

wherein
in the formula (II), -----
is a single bond or a double bond,
in the formulas (II) and (III),
s is an integer of 1 or 2,
t is an integer of 1 or 2,
$R^3$ is a hydrogen atom, a halogen atom, an optionally substituted alkyl, a hydroxyl, an alkoxy, a carboxy or an alkoxycarbonyl,
ring $Ar^1$ is an aryl or an aromatic heterocyclic ring,
$R^4, R^{4'}, R^{4''}$ are the same or different and each is a hydrogen atom, a halogen atom, an optionally substituted alkyl, an optionally substituted alkenyl, an optionally substituted alkynyl, a hydroxyl, an alkoxy, a carboxy, an alkoxycarbonyl, an acyl, —O(C=O)$R^{4a}$ (wherein $R^{4a}$ is an optionally substituted $C_{1-6}$ alkyl), —(C=O)NR$^{4a'}$R$^{4a''}$ (wherein R$^{4a'}$ and R$^{4a''}$ are the same or different and each is a hydrogen atom or an optionally substituted $C_{1-6}$ alkyl, or R$^{4a'}$ and R$^{4a''}$ are taken together to form an optionally substituted 5- to 7-membered non-aromatic heterocyclic ring), —NH(C=O)$R^{4a}$ (wherein $R^{4a}$ is an optionally substituted $C_{1-6}$ alkyl), —SO$_2$NR$^{4a'}$R$^{4a''}$ (wherein R$^{4a'}$ and R$^{4a''}$ are the same or different and each is a hydrogen atom or an optionally substituted $C_{1-6}$ alkyl, or R$^{4a'}$ and R$^{4a''}$ are taken together to form an optionally substituted 5- to 7-membered non-aromatic heterocyclic ring), —NHSO$_2$R$^{4a}$ (wherein R$^{4a}$ is an optionally substituted $C_{1-6}$ alkyl), an amino, an alkylamino, —SR$^{4a}$ (wherein R$^{4a}$ is an optionally substituted $C_{1-6}$ alkyl), —SO$_2$R$^{4a}$ (wherein R$^{4a}$ is an optionally substituted $C_{1-6}$ alkyl), a cyano, an optionally substituted phenyl or an optionally substituted heterocyclic ring, or $R^4$ and $R^{4'}$ are taken together to form an $C_{1-3}$ alkylenedioxy, and
$R^5$ is absent, or a hydrogen atom, a halogen atom, an optionally substituted alkyl, a hydroxyl, an alkoxy, an alkoxycarbonyl, an acyl, —(C=O)NR$^{5a}$R$^{5a'}$ (wherein R$^{5a}$ and R$^{5a'}$ are the same or different and each is a hydrogen atom or an optionally substituted $C_{1-6}$ alkyl), —NH(C=O)R$^{5a''}$ (wherein R$^{5a''}$ is an optionally substituted $C_{1-6}$ alkyl), an amino, an alkylamino, —SR$^{5a}$ (wherein R$^{5a}$ is a hydrogen atom or an optionally substituted $C_{1-6}$ alkyl) or a cyano, in the formulas (IV) and (V), -----
is a single bond or a double bond,
Y is a carbonyl, NR$^{10}$, an oxygen atom or a sulfur atom, wherein R$^{10}$ is a hydrogen atom, an optionally substituted alkyl, an acyl, an alkoxycarbonyl or —SO$_2$R$^{10a}$ (wherein R$^{10a}$ is an optionally substituted $C_{1-6}$ alkyl or an optionally substituted phenyl),
ring $Ar^2$ is a phenyl or an aromatic heterocyclic ring,
$R^6$ and $R^{6'}$ are the same or different and each is a hydrogen atom, a halogen atom, an optionally substituted alkyl, an optionally substituted alkenyl, an optionally substituted alkynyl, a hydroxyl, an alkoxy, a carboxy, an alkoxycarbonyl, an acyl, —O(C=O)R$^{6a}$ (wherein R$^{6a}$ is an optionally substituted $C_{1-6}$ alkyl), —(C=O)NR$^{6a'}$R$^{6a''}$ (wherein R$^{6a'}$ and R$^{6a''}$ are the same or different and each is a hydrogen atom or an optionally substituted $C_{1-6}$ alkyl, or
R$^{6a'}$ and R$^{6a''}$ are taken together to form an optionally substituted 5- to 7-membered non-aromatic heterocyclic ring), —NH(C=O)R$^{6a}$ (wherein R$^{6a}$ is an optionally substituted $C_{1-6}$ alkyl), —SO$_2$NR$^{6a'}$R$^{6a''}$ (wherein R$^{6a'}$ and R$^{6a''}$ are the same or different and each is a hydrogen atom or an optionally substituted $C_{1-6}$ alkyl, or R$^{6a'}$ and R$^{6a''}$ are taken together to form an optionally substituted 5- to 7-membered non-aromatic heterocyclic ring), —NHSO$_2$R$^{6a}$ (wherein R$^{6a}$ is an optionally substituted $C_{1-6}$ alkyl), an amino, an alkylamino, —SR$^{6a}$ (wherein R$^{6a}$ is an optionally substituted $C_{1-6}$ alkyl), a cyano, an optionally substituted phenyl or an optionally substituted heterocyclic ring, or
$R^4$ and $R^{4'}$ are taken together to form a $C_{1-3}$ alkylenedioxy, and
$R^7$ is a hydrogen atom or an optionally substituted alkyl, in the formula (VI),
X and W are any of C(=O) and O, C(=O) and NR$^{11}$, and NR$^{11}$ and C(=O),
wherein R$^{11}$ is a hydrogen atom or an optionally substituted alkyl,
ring $Ar^2$ is a phenyl or an aromatic heterocyclic ring, and $R^6$ and $R^{6'}$ are the same or different and each is a hydrogen atom, a halogen atom, an optionally substituted alkyl, an optionally substituted alkenyl, an optionally substituted alkynyl, a hydroxyl, an alkoxy, a carboxy, an alkoxycarbonyl, an acyl, —O(C=O)R$^{6a}$ (wherein R$^{6a}$ is an optionally substituted $C_{1-6}$ alkyl), —(C=O)NR$^{6a'}$R$^{6a''}$ (wherein R$^{6a'}$ and R$^{6a''}$ are the same or different and each is a hydrogen atom or an optionally substituted $C_{1-6}$ alkyl, or R$^{6a'}$ and R$^{6a''}$ are taken together to form an optionally substituted 5- to 7-membered non-aromatic heterocyclic ring), —NH(C=O)R$^{6a}$ (wherein R$^{6a}$ is an optionally substituted $C_{1-6}$ alkyl), —SO$_2$NR$^{6a'}$R$^{6a''}$ (wherein R$^{6a'}$ and R$^{6a''}$ are the same or different and each is a hydrogen atom or an optionally substituted $C_{1-6}$ alkyl, or R$^{6a'}$ and R$^{6a''}$ are taken together to form an optionally substituted 5- to 7-membered non-aromatic heterocyclic ring), —NHSO$_2$R$^{6a}$ (wherein R$^{6a}$ is an optionally substituted $C_{1-6}$ alkyl), an amino, an alkylamino, —SR$^{6a}$ (wherein R$^{6a}$ is an optionally substituted $C_{1-6}$ alkyl), a cyano, an optionally substituted phenyl or an optionally substituted heterocyclic ring, or $R^4$ and $R^{4'}$ are taken together to form a $C_{1-3}$ alkylenedioxy, and
in the formula (VII),
Z is a carbon atom or a nitrogen atom,
ring $Ar^2$ is a phenyl or an aromatic heterocyclic ring, and $R^6$ and $R^{6'}$ are the same or different and each is a hydrogen atom, a halogen atom, an optionally substituted alkyl, an optionally substituted alkenyl, an optionally substituted alkynyl, a hydroxyl, an alkoxy, a carboxy, an alkoxycarbonyl, an acyl, —O(C=O)R$^{6a}$ (wherein R$^{6a}$ is an optionally substituted $C_{1-6}$ alkyl), —(C=O)NR$^{6a'}$R$^{6a''}$ (wherein R$^{6a'}$ and R$^{6a''}$ are the same or different and each is a hydrogen atom or an optionally substituted $C_{1-6}$ alkyl, or
R$^{6a'}$ and R$^{6a''}$ are taken together to form an optionally substituted 5- to 7-membered non-aromatic heterocyclic ring), —NH(C=O)R$^{6a}$ (wherein R$^{6a}$ is an optionally substituted $C_{1-6}$ alkyl), —SO$_2$NR$^{6a'}$R$^{6a''}$ (wherein R$^{6a'}$ and R$^{6a''}$ are the same or different and each is a hydrogen atom or an optionally substituted $C_{1-6}$ alkyl, or R$^{6a'}$ and R$^{6a''}$ are taken together to form an optionally substituted 5- to 7-membered non-aromatic heterocyclic ring), —NHSO$_2$R$^{6a}$ (wherein R$^{6a}$ is an optionally substituted C$_{1-6}$ alkyl), an amino, an alkylamino, —SR$^{6a}$ (wherein R$^{6a}$ is an optionally substituted C$_{1-6}$ alkyl), a cyano, an optionally substituted phenyl or an optionally substituted heterocyclic ring, or R$^4$ an R$^{4'}$ are taken together to form a C$_{1-3}$ alkylenedioxy, a pharmaceutically acceptable salt thereof, a hydrate thereof, a water adduct thereof or a solvate thereof.

(2) The indazole compound of the above-mentioned (1), wherein, in the above-mentioned formula (I), R$^2$ is any of the following formula (II) to the following formula (V),

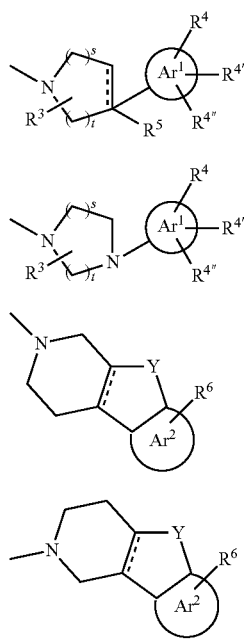

wherein
in the formula (II), ‑‑‑‑‑
is a single bond or a double bond,
in the formulas (II) and (III),
s is an integer of 1 or 2,
t is an integer of 0 to 2,
R$^3$ is a hydrogen atom, a halogen atom, an optionally substituted alkyl, a carboxyl, an alkoxycarbonyl, a hydroxy or an alkoxy,
ring Ar$^1$ is a phenyl or an aromatic heterocyclic ring, R$^4$, R$^{4'}$ and R$^{4''}$ are the same or different and each is a hydrogen atom, a halogen atom, an optionally substituted alkyl, an alkoxycarbonyl, a hydroxy, an alkoxy, a sulfonamide, a mercapto, a sulfinyl, a sulfonyl, an amino or an alkylamino, and
R$^5$ is absent, or a hydrogen atom, a halogen atom, an optionally substituted alkyl, a hydroxy, an alkoxy, an amino, an alkylamino, a sulfanyl or a cyano, and in the formulas (IV) and (V), ‑‑‑‑‑
is a single bond or a double bond,
Y is a carbonyl, NR$^{10}$, an oxygen atom or a sulfur atom, wherein R$^{10}$ is a hydrogen atom, an optionally substituted alkyl, an acyl, an alkoxycarbonyl or a sulfonyl,
ring Ar$^2$ is a phenyl or an aromatic heterocyclic ring,
R$^6$ is a hydrogen atom, a halogen atom, an optionally substituted alkyl, a cyano, a hydroxy or an alkoxy, a pharmaceutically acceptable salt thereof, a hydrate thereof, a water adduct thereof or a solvate thereof.

(3) The indazole compound of the above-mentioned (1), wherein,
in the above-mentioned formula (I),
R$^1$ is a hydrogen atom or an optionally substituted alkyl, in the above-mentioned formulas (II) and (III),
s is an integer of 1,
t is an integer of 2,
R$^3$ is a hydrogen atom,
ring Ar$^1$ is a phenyl or a thiophene,
R$^{4'}$, R$^{4''}$, R$^4$ are the same or different and each is a hydrogen atom, a halogen atom, an optionally substituted alkyl, a hydroxy, an alkoxy, —SR$^{4a}$ (wherein R$^{4a}$ is an optionally substituted C$_{1-6}$ alkyl) or an cyano, and
R$^5$ is a hydroxy or a cyano,
in the above-mentioned formulas (IV) and (V), Y is NR$^{10}$, wherein R$^{10}$ is a hydrogen atom or an optionally substituted alkyl,
ring Ar$^2$ is a phenyl, and
R$^6$ and R$^{6'}$ are the same or different and each is a hydrogen atom, a halogen atom, an optionally substituted alkyl, a hydroxy or an alkoxy,
in the above-mentioned formula (VI),
X and W are any of C(=O) and O, C(=O) and NR$^{11}$, and NR$^{11}$ and C(=O),
wherein R$^{11}$ is a hydrogen atom,
ring Ar$^2$ is a phenyl, and
R$^6$ and R$^{6'}$ are the same or different and each is a hydrogen atom, a halogen atom or an optionally substituted alkyl, and
in the above-mentioned formula (VII),
ring Ar$^2$ is a phenyl, and
R$^6$ and R$^{6'}$ are the same or different and each is a hydrogen atom, a halogen atom or an optionally substituted alkyl, a pharmaceutically acceptable salt thereof, a hydrate thereof, a water adduct thereof or a solvate thereof.

(4) The indazole compound of the above-mentioned (1) or (3), wherein,
in the above-mentioned formula (I),
R$^1$ is a hydrogen atom,
in the above-mentioned formulas (II) and (III),
s is an integer of 1,
t is an integer of 2,
R$^3$ is a hydrogen atom,
ring Ar$^1$ is a phenyl,
R$^4$, R$^{4'}$, R$^{4''}$ are the same or different and each is a hydrogen atom, a halogen atom or an optionally substituted alkyl, and
R$^5$ is a hydroxy or a cyano, and
in the above-mentioned formula (IV),
Y is NR$^{10}$,
wherein R$^{10}$ is a hydrogen atom or a methyl,
a pharmaceutically acceptable salt thereof, a hydrate thereof, a water adduct thereof or a solvate thereof.

(5) The indazole compound of any of the above-mentioned (1) to (4),
wherein,
in the above-mentioned formula (I),
R$^1$ is a hydrogen atom, and
in the above-mentioned formula (II),
s is an integer of 1,
t is an integer of 2,
R$^3$ is a hydrogen atom,
ring Ar$^1$ is a phenyl, R⁴, R⁴', R⁴" are the same or different and each is a hydrogen atom, a halogen atom or an optionally substituted alkyl, and R⁵ is a hydroxyl, a pharmaceutically acceptable salt thereof, a hydrate thereof, a water adduct thereof or a solvate thereof.

(6) The indazole compound of the above-mentioned (1), which is selected from (1) 4-[4-chloro-3-(trifluoromethyl)phenyl]-4-hydroxy-1-piperidinecarboxylic acid (1H-indazol-3-yl)amide, (3) 4-hydroxy-4-[3-(trifluoromethyl)phenyl]-1-piperidinecarboxylic acid (1H-indazol-3-yl)amide, (4) 4-(4-chlorophenyl)-4-hydroxy-1-piperidinecarboxylic acid (1H-indazol-3-yl)amide, (6) 4-[3-fluoro-5-(trifluoromethyl)phenyl]-4-hydroxy-1-piperidinecarboxylic acid (1H-indazol-3-yl)amide, (9) 4-[4-fluoro-3-(trifluoromethyl)phenyl]-4-hydroxy-1-piperidinecarboxylic acid (1H-indazol-3-yl)amide,

(10) 4-hydroxy-4-[4-methyl-3-(trifluoromethyl)phenyl]-1-piperidinecarboxylic acid (1H-indazol-3-yl)amide,

(12) 4-(3,5-difluorophenyl)-4-hydroxy-1-piperidinecarboxylic acid (1H-indazol-3-yl)amide,

(15) 4-(3-chloro-4-fluorophenyl)-4-hydroxy-1-piperidinecarboxylic acid (1H-indazol-3-yl)amide,

(20) 4-(3-chloro-2-fluorophenyl)-4-hydroxy-1-piperidinecarboxylic acid (1H-indazol-3-yl)amide,

(21) 4-(3,4-dichlorophenyl)-4-hydroxy-1-piperidinecarboxylic acid (1H-indazol-3-yl)amide,

(22) 4-(3-chloro-5-fluorophenyl)-4-hydroxy-1-piperidinecarboxylic acid (1H-indazol-3-yl)amide,

(23) 4-(4-chloro-3-methylphenyl)-4-hydroxy-1-piperidinecarboxylic acid (1H-indazol-3-yl)amide,

(24) 4-(3-chlorophenyl)-4-hydroxy-1-piperidinecarboxylic acid (1H-indazol-3-yl)amide,

(27) 4-(1,3-benzodioxol-5-yl)-4-hydroxy-1-piperidinecarboxylic acid (1H-indazol-3-yl)amide,

(28) 4-hydroxy-4-(3-methylphenyl)-1-piperidinecarboxylic acid (1H-indazol-3-yl)amide,

(29) 4-(3-cyanophenyl)-4-hydroxy-1-piperidinecarboxylic acid (1H-indazol-3-yl) amide,

(30) 4-hydroxy-4-[3-(methylthio)phenyl]-1-piperidinecarboxylic acid (1H-indazol-3-yl)amide,

(31) 4-(3-ethylphenyl)-4-hydroxy-1-piperidinecarboxylic acid (1H-indazol-3-yl)amide,

(33) 4-(2,5-dichlorophenyl)-4-hydroxy-1-piperidinecarboxylic acid (1H-indazol-3-yl)amide,

(34) 4-[3,5-bis(trifluoromethyl)phenyl]-4-hydroxy-1-piperidinecarboxylic acid (1H-indazol-3-yl)amide,

(35) 4-[2-fluoro-5-(trifluoromethyl)phenyl]-4-hydroxy-1-piperidinecarboxylic acid (1H-indazol-3-yl)amide,

(36) 4-[2-chloro-5-(trifluoromethyl)phenyl]-4-hydroxy-1-piperidinecarboxylic acid (1H-indazol-3-yl)amide,

(40) 4-cyano-4-(2-methoxyphenyl)-1-piperidinecarboxylic acid (1H-indazol-3-yl)amide,

(42) 4-cyano-4-[3-(trifluoromethyl)phenyl]-1-piperidinecarboxylic acid (1H-indazol-3-yl)amide,

(43) 4-cyano-4-(2-fluorophenyl)-1-piperidinecarboxylic acid (1H-indazol-3-yl)amide,

(44) 4-[4-chloro-3-(trifluoromethyl)phenyl]-4-cyano-1-piperidinecarboxylic acid (1H-indazol-3-yl)amide,

(46) 4-(5-bromo-2-thienyl)-4-cyano-1-piperidinecarboxylic acid (1H-indazol-3-yl)amide,

(47) 4-cyano-4-(3,5-difluorophenyl)-1-piperidinecarboxylic acid (1H-indazol-3-yl)amide,

(48) 4-(4-bromo-2-chlorophenyl)-4-cyano-1-piperidinecarboxylic acid (1H-indazol-3-yl)amide,

(49) 4-phenyl-1,2,3,6-tetrahydropyridine-1-carboxylic acid (1H-indazol-3-yl)amide,

(50) 4-(4-fluorophenyl)-1,2,3,6-tetrahydropyridine-1-carboxylic acid (1H-indazol-3-yl)amide,

(52) 4-(2-fluorophenyl)-1,2,3,6-tetrahydropyridine-1-carboxylic acid (1H-indazol-3-yl)amide,

(53) 4-(3-chloro-4-fluorophenyl)-1,2,3,6-tetrahydropyridine-1-carboxylic acid (1H-indazol-3-yl)amide,

(55) 4-(3-fluorophenyl)-1,2,3,6-tetrahydropyridine-1-carboxylic acid (1H-indazol-3-yl)amide,

(56) 4-(2,3-difluorophenyl)-1,2,3,6-tetrahydropyridine-1-carboxylic acid (1H-indazol-3-yl)amide,

(58) 4-(5-chloro-2-thienyl)-1,2,3,6-tetrahydropyridine-1-carboxylic acid (1H-indazol-3-yl)amide,

(59) 4-(3-methyl-2-thienyl)-1,2,3,6-tetrahydropyridine-1-carboxylic acid (1H-indazol-3-yl)amide,

(60) 4-(2-thienyl)-1,2,3,6-tetrahydropyridine-1-carboxylic acid (1H-indazol-3-yl)amide,

(61) 4-[3-(trifluoromethyl)phenyl]-1,2,3,6-tetrahydropyridine-1-carboxylic acid (1H-indazol-3-yl)amide,

(62) 4-(3,4-dimethoxyphenyl)-1,2,3,6-tetrahydropyridine-1-carboxylic acid (1H-indazol-3-yl)amide,

(63) 4-[3-(dimethylamino)phenyl]-1,2,3,6-tetrahydropyridine-1-carboxylic acid (1H-indazol-3-yl)amide,

(64) 1,3,4,9-tetrahydro-β-carboline-2-carboxylic acid (1H-indazol-3-yl)amide,

(65) 9-methyl-1,3,4,9-tetrahydro-β-carboline-2-carboxylic acid (1H-indazol-3-yl)amide,

(66) 9-(2-methoxyethyl)-1,3,4,9-tetrahydro-β-carboline-2-carboxylic acid (1H-indazol-3-yl)amide,

(69) 6-(trifluoromethyl)-1,3,4,9-tetrahydro-β-carboline-2-carboxylic acid (1H-indazol-3-yl)amide,

(70) 6-fluoro-1,3,4,9-tetrahydro-β-carboline-2-carboxylic acid (1H-indazol-3-yl)amide,

(71) 7-fluoro-1,3,4,9-tetrahydro-β-carboline-2-carboxylic acid (1H-indazol-3-yl)amide,

(72) 6-chloro-1,3,4,9-tetrahydro-β-carboline-2-carboxylic acid (1H-indazol-3-yl)amide,

(73) 6-methoxy-1,3,4,9-tetrahydro-β-carboline-2-carboxylic acid (1H-indazol-3-yl)amide,

(74) 6-hydroxy-1,3,4,9-tetrahydro-β-carboline-2-carboxylic acid (1H-indazol-3-yl)amide,

(75) 7-chloro-1,3,4,9-tetrahydro-β-carboline-2-carboxylic acid (1H-indazol-3-yl) amide,

(76) 7-(trifluoromethyl)-1,3,4,9-tetrahydro-β-carboline-2-carboxylic acid (1H-indazol-3-yl)amide,

(77) 5-fluoro-1,3,4,9-tetrahydro-β-carboline-2-carboxylic acid (1H-indazol-3-yl)amide,

(78) 5-chloro-1,3,4,9-tetrahydro-β-carboline-2-carboxylic acid (1H-indazol-3-yl)amide,

(79) 8-methyl-1,3,4,9-tetrahydro-β-carboline-2-carboxylic acid (1H-indazol-3-yl)amide,

(80) 3,4-dihydro[1]benzothieno[2,3-c]pyridine-2-carboxylic acid (1H-indazol-3-yl)amide,

(81) 6-methyl-1,3,4,9-tetrahydro-β-carboline-2-carboxylic acid (1H-indazol-3-yl)amide,

(82) 7-chloro-6-fluoro-1,3,4,9-tetrahydro-β-carboline-2-carboxylic acid (1H-indazol-3-yl)amide,

(83) 7-chloro-6-(trifluoromethyl)-1,3,4,9-tetrahydro-β-carboline-2-carboxylic acid (1H-indazol-3-yl)amide,

(93) 4-[4-chloro-3-(trifluoromethyl)phenyl]-1-piperazinecarboxylic acid (1H-indazol-3-yl)amide,

(94) 4-[4-fluoro-3-(trifluoromethyl)phenyl]-1-piperazinecarboxylic acid (1H-indazol-3-yl)amide,

(95) 4-[4-methoxy-3-(trifluoromethyl)phenyl]-1-piperazinecarboxylic acid (1H-indazol-3-yl)amide,

(97) 4-[3-fluoro-5-(trifluoromethyl)phenyl]-1-piperazinecarboxylic acid (1H-indazol-3-yl)amide,
(98) 4-(3,4-dichlorophenyl)-1-piperazinecarboxylic acid (1H-indazol-3-yl)amide,
(99) 4-[2-chloro-5-(trifluoromethyl)phenyl]-1-piperazinecarboxylic acid (1H-indazol-3-yl)amide,
(100) 4-[3-(trifluoromethyl)phenyl]-1-piperazinecarboxylic acid (1H-indazol-3-yl)amide,
(103) 5-oxo-1,5-dihydro-2H-chromeno[3,4-c]pyridine-3-carboxylic acid (1H-indazol-3-yl)amide,
(104) 5-oxo-1,4,5,6-tetrahydrobenzo[c]-2,7-naphthyridine-3-carboxylic acid (1H-indazol-3-yl)amide,
(105) 3,4-dihydropyrazino[1,2-a]benzimidazole-2-carboxylic acid (1H-indazol-3-yl)amide,
(106) 3,4-dihydropyrazino[1,2-a]indole-2-carboxylic acid (1H-indazol-3-yl)amide,
(108) 1-[(dimethylamino)methyl]-1,3,4,9-tetrahydro-β-carboline-2-carboxylic acid (1H-indazol-3-yl)amide,
(109) 6-oxo-1,4,5,6-tetrahydrobenzo[c]-1,7-naphthyridine-3-carboxylic acid (1H-indazol-3-yl)amide,
(112) 4-[3-(trifluoromethyl)phenyl]piperidine-1-carboxylic acid (1H-indazol-3-yl)amide,
(116) 4-[4-chloro-3-(trifluoromethyl)phenyl]-4-methoxypiperidine-1-carboxylic acid (1H-indazol-3-yl)amide,
(117) 4-[4-chloro-3-(trifluoromethyl)phenyl]-3-ethylpiperazine-1-carboxylic acid (1H-indazol-3-yl)amide,
(123) 4-[4-chloro-3-(trifluoromethyl)phenyl]-4-fluoropiperidine-1-carboxylic acid (1H-indazol-3-yl)amide,
(130) 4-(2-fluoro-5-methylphenyl)-4-hydroxy-1-piperidinecarboxylic acid (1H-indazol-3-yl)amide,
(131) 4-(3-chloro-2-methylphenyl)-4-hydroxy-1-piperidinecarboxylic acid (1H-indazol-3-yl)amide,
(132) 4-(3-chloro-4-methylphenyl)-4-hydroxy-1-piperidinecarboxylic acid (1H-indazol-3-yl)amide,
(134) 4-(3-fluoro-2-methylphenyl)-4-hydroxy-1-piperidinecarboxylic acid (1H-indazol-3-yl)amide,
(135) 4-(5-fluoro-2-methylphenyl)-4-hydroxy-1-piperidinecarboxylic acid (1H-indazol-3-yl)amide,
(136) 4-(4-fluoro-3-methylphenyl)-4-hydroxy-1-piperidinecarboxylic acid (1H-indazol-3-yl)amide,
(138) 4-(3-fluoro-5-methylphenyl)-4-hydroxy-1-piperidinecarboxylic acid (1H-indazol-3-yl)amide,
(139) 4-(2,5-dimethylphenyl)-4-hydroxy-1-piperidinecarboxylic acid (1H-indazol-3-yl)amide,
(140) 4-hydroxy-4-[2-methyl-3-(trifluoromethyl)phenyl]-1-piperidinecarboxylic acid (1H-indazol-3-yl)amide,
(141) 4-hydroxy-4-[2-methyl-5-(trifluoromethyl)phenyl]-1-piperidinecarboxylic acid (1H-indazol-3-yl)amide,
(142) 4-(3,4-dimethylphenyl)-4-hydroxy-1-piperidinecarboxylic acid (1H-indazol-3-yl)amide,
(143) 4-(3,5-dimethylphenyl)-4-hydroxy-1-piperidinecarboxylic acid (1H-indazol-3-yl)amide, and
(144) 4-(2,3-dimethylphenyl)-4-hydroxy-1-piperidinecarboxylic acid (1H-indazol-3-yl)amide,
a pharmaceutically acceptable salt thereof, a hydrate thereof, a water adduct thereof or a solvate thereof.
(7) The indazole compound of the above-mentioned (1), which is 4-hydroxy-4-(3-methylphenyl)-1-piperidinecarboxylic acid (1H-indazol-3-yl)amide, a pharmaceutically acceptable salt thereof, a hydrate thereof, a water adduct thereof or a solvate thereof.
(8) The indazole compound of the above-mentioned (1), which is 4-(3-chloro-2-fluorophenyl)-4-hydroxy-1-piperidinecarboxylic acid (1H-indazol-3-yl)amide, a pharmaceutically acceptable salt thereof, a hydrate thereof, a water adduct thereof or a solvate thereof.
(9) The indazole compound of the above-mentioned (1), which is 4-(4-fluorophenyl)-1,2,3,6-tetrahydropyridine-1-carboxylic acid (1H-indazol-3-yl)amide, a pharmaceutically acceptable salt thereof, a hydrate thereof, a water adduct thereof or a solvate thereof.
(10) The indazole compound of the above-mentioned (1), which is 1,3,4,9-tetrahydro-β-carboline-2-carboxylic acid (1H-indazol-3-yl)amide, a pharmaceutically acceptable salt thereof, a hydrate thereof, a water adduct thereof or a solvate thereof.
(11) The indazole compound of the above-mentioned (1), which is 4-[4-chloro-3-(trifluoromethyl)phenyl]-1-piperazinecarboxylic acid (1H-indazol-3-yl)amide, a pharmaceutically acceptable salt thereof, a hydrate thereof, a water adduct thereof or a solvate thereof.
(12) An agent for the prophylaxis and/or treatment of cancer, which comprises an indazole compound of any of the above-mentioned (1) to (11), a pharmaceutically acceptable salt thereof, a hydrate thereof, a water adduct thereof or a solvate thereof.

Effect of the Invention

The present invention can provide a cancer treatment drug comprising, as an active ingredient, a substance selected from the group consisting of an indazole compound represented by the above-mentioned formula (I), a pharmaceutically acceptable salt, a hydrate, a water adduct and a solvate.

BEST MODE FOR EMBODYING THE INVENTION

The present invention is explained in detail in the following.

Respective substituents represented by the above-mentioned formula (I) of the present invention are defined in the following.

As the "substituent" of the "optionally substituted alkyl" for $R^1$, for example, a halogen atom (e.g., fluorine, chlorine, bromine, iodine), cyano, nitro, hydroxy, mercapto, amino, formyl, carboxy, carbamoyl, $(C_{2-6})$alkenyl, $(C_{2-6})$alkynyl, $(C_{1-6})$alkoxy, $(C_{2-6})$alkenyloxy, $(C_{2-6})$alkynyloxy, $(C_{1-6})$alkylthio, $(C_{1-6})$alkylsulfonyl, $(C_{1-6})$alkylamino, di[$(C_{1-6})$alkyl]amino, $(C_{1-6})$alkoxycarbonyl, N-$(C_{1-6})$alkylcarbamoyl, N,N-di[$(C_{1-6})$alkyl]carbamoyl, $(C_{2-6})$alkanoyl, $(C_{2-6})$alkanoyloxy, $(C_{2-6})$alkanoylamino, N-$(C_{1-6})$alkyl-$(C_{2-6})$alkanoylamino, $(C_{3-6})$alkenoylamino, N-$(C_{1-6})$alkyl-$(C_{3-6})$alkenoylamino, $(C_{3-6})$alkynoylamino, N-$(C_{1-6})$alkyl-$(C_{3-6})$alkynoylamino, N-$(C_{1-6})$alkylsulfamoyl, N,N-di[$(C_{1-6})$alkyl]sulfamoyl, $(C_{1-6})$alkanesulfonylamino, N-$(C_{1-6})$alkyl-$(C_{1-6})$alkanesulfonylamino and so on can be mentioned.

As the "alkyl" of the "optionally substituted alkyl" for $R^1$, for example, $C_{1-6}$ alkyl (e.g., methyl, ethyl, propyl, isopropyl, butyl, isobutyl, sec-butyl, tert-butyl, pentyl, hexyl, cyclopentyl, cyclohexyl etc.) can be mentioned, with particular preference given to $C_{1-3}$ alkyl (e.g., methyl, ethyl, propyl, isopropyl). The "alkyl" optionally has, for example, 1 to 5, preferably 1 to 3, substituents mentioned above at substitutable position(s), and when the number of the substituents is not less than 2, respective substituents may be the same or different. For example, the $C_{1-6}$ alkyl optionally has 1 to 3 halogen atoms (e.g., fluorine, chlorine, bromine, iodine) (e.g., chloromethyl, difluoromethyl, trifluoromethyl, trifluoroethyl etc.) can be mentioned.

As the "substituent" of the "optionally substituted phenyl" for $R^1$, for example, those exemplarily recited as the "substituent" of the aforementioned "optionally substituted alkyl" for $R^1$ can be mentioned.

As the "substituent" of the "optionally substituted aromatic heterocyclic ring" for $R^1$, for example, those exemplarily recited as the "substituent" of the aforementioned "optionally substituted alkyl" for $R^1$ can be mentioned.

As the "aromatic heterocyclic ring" of the "optionally substituted aromatic heterocyclic ring" for $R^1$, for example, a 5- or 6-membered aromatic heterocyclic ring containing, besides carbon atoms, one or two kinds of 1 to 4 heteroatoms selected from a nitrogen atom, a sulfur atom and an oxygen atom (e.g., thiophene, furan, pyrrole, imidazole, pyrazole, pyridine, pyrazine, pyrimidine, thiazole, oxazole etc.), and an aromatic fused heterocyclic ring containing, besides carbon atoms, one or two kinds of 1 to 4 heteroatoms selected from a nitrogen atom, a sulfur atom and an oxygen atom (e.g., benzothiophene, indole, quinazoline etc.) can be mentioned.

As the "halogen atom" for $R^3$, for example, fluorine, chlorine, bromine and iodine can be mentioned.

As the "substituent" and "alkyl" of the "optionally substituted alkyl" for $R^3$, for example, those exemplarily recited as the "substituent" and "alkyl" of the aforementioned "optionally substituted alkyl" for $R^1$ can be mentioned.

As the "alkoxy" for $R^3$, for example, alkoxy having a total carbon number of 1 to 6, i.e., $-OR^{3b}$, can be mentioned. As used herein, as $R^{3b}$, $C_{1-6}$ alkyl (e.g., methyl, ethyl, propyl, isopropyl, butyl, isobutyl, sec-butyl, tert-butyl, pentyl, hexyl etc.) can be mentioned. As the alkoxy, for example, methoxy, ethoxy, propoxy, isopropoxy, butoxy, tertiary butoxy and so on can be mentioned.

As the "alkoxycarbonyl" for $R^3$, for example, alkoxycarbonyl having a total carbon number of 1 to 7, i.e., $-(C=O)OR^{3a}$, can be mentioned. As used herein, as $R^{3a}$, $C_{1-6}$ alkyl (e.g., methyl, ethyl, propyl, isopropyl, butyl, isobutyl, sec-butyl, tert-butyl etc.) can be mentioned. As the alkoxycarbonyl, for example, methoxycarbonyl, ethoxycarbonyl, propoxycarbonyl, isopropoxycarbonyl, butoxycarbonyl, tertiary butoxycarbonyl and so on can be mentioned.

As the "aryl" for $Ar^1$, a monocyclic or fused ring can be mentioned and, for example, phenyl, 1-naphthyl, 2-naphthyl and so on, preferably phenyl can be mentioned.

As the "aromatic heterocyclic ring" for $Ar^1$, for example, those exemplarily recited as the "aromatic heterocyclic ring" of the aforementioned "optionally substituted aromatic heterocyclic ring" for $R^1$ can be mentioned. Particularly, thiophene is preferable.

As the "halogen atom" for $R^4$, $R^{4'}$ or $R^{4''}$, for example, those exemplarily recited as the aforementioned "halogen atom" for $R^3$ can be mentioned. Particularly, fluorine, chlorine and bromine are preferable.

As the "substituent" and "alkyl" of the "optionally substituted alkyl" for $R^4$, $R^{4'}$ or $R^{4''}$, for example, those exemplarily recited as the "substituent" and "alkyl" of the aforementioned "optionally substituted alkyl" for $R^1$ can be mentioned. Particularly, methyl, ethyl and trifluoromethyl are preferable.

As the "substituent" of the "optionally substituted alkenyl" for $R^4$, $R^{4'}$ or $R^{4''}$, for example, those exemplarily recited as the "substituent" of the aforementioned "optionally substituted alkyl" for $R^1$ can be mentioned.

As the "alkenyl" of the "optionally substituted alkenyl" for $R^4$, $R^{4'}$ or $R^{4''}$, for example, $C_{2-6}$ alkenyl (e.g., vinyl, isopropenyl, allyl, but-2-enyl etc.) can be mentioned.

As the "substituent" of the "optionally substituted alkynyl" for $R^4$, $R^{4'}$ or $R^{4''}$, for example, those exemplarily recited as the "substituent" of the aforementioned "optionally substituted alkyl" for $R^1$ can be mentioned.

As the "alkynyl" of the "optionally substituted alkynyl" for $R^4$, $R^{4'}$ or $R^{4''}$, for example, $C_{2-6}$ alkynyl (e.g., ethynyl, 2-propynyl, but-2-ynyl etc.) can be mentioned.

As the "alkoxy" for $R^4$, $R^{4'}$ or $R^{4''}$, for example, those exemplarily recited as the aforementioned "alkoxy" for $R^3$ can be mentioned. Particularly, methoxy and trifluoromethoxy are preferable.

As the "alkoxycarbonyl" for $R^4$, $R^{4'}$ or $R^{4''}$, for example, those exemplarily recited as the aforementioned "alkoxycarbonyl" for $R^3$ can be mentioned.

As the "acyl" for $R^4$, $R^{4'}$ or $R^{4''}$, for example, acyl having a total carbon number of 1 to 6, for example, formyl, acetyl, propionyl, 2-methylpropionyl, butyryl and so on can be mentioned.

As the "substituent" and "alkyl" of the "optionally substituted alkyl" for $R^{4a}$, $R^{4a'}$ or $R^{4a''}$, for example, those exemplarily recited as the "substituent" and "alkyl" of the aforementioned "optionally substituted alkyl" for $R^1$ can be mentioned.

As the "substituent" of the "optionally substituted 5- to 7-membered non-aromatic heterocyclic ring" for $NR^{4a'}R^{4a''}$ in $-(C=O)NR^{4a'}R^{4a''}$ or $-SO_2NR^{4a'}R^{4a''}$, for example, those exemplarily recited as the "substituent" of the aforementioned "optionally substituted alkyl" for $R^1$ can be mentioned.

As the "non-aromatic heterocyclic ring" of the "optionally substituted 5- to 7-membered non-aromatic heterocyclic ring" for $NR^{4a'}R^{4a''}$ in $-(C=O)NR^{4a'}R^{4a''}$ or $-SO_2NR^{4a'}R^{4a''}$, for example, a 5- to 7-membered non-aromatic heterocyclic ring containing, besides carbon atoms, one or two kinds of 1 to 3 heteroatoms selected from a nitrogen atom, a sulfur atom and an oxygen atom (e.g., piperidine, piperazine, pyrrolidine, morpholine, thiomorpholine etc.) can be mentioned.

As the "alkylamino" for $R^4$, $R^{4'}$ or $R^{4''}$, for example, alkylamino having a total carbon number of 1 to 6, i.e., $-NR^{4a}R^{4a''}$, can be mentioned. As used herein, as $R^{4b}$, hydrogen and $C_{1-6}$ alkyl (e.g., methyl, ethyl, propyl, isopropyl, butyl, isobutyl, sec-butyl, tert-butyl, pentyl, hexyl etc.) can be mentioned. As $R^{4b'}$, $C_{1-6}$ alkyl (e.g., methyl, ethyl, propyl, isopropyl, butyl, isobutyl, sec-butyl, tert-butyl, pentyl, hexyl etc.) can be mentioned. As the alkylamino, for example, methylamino, ethylamino, n-propylamino, isopropylamino, n-butylamino, dimethylamino, diethylamino, N-methyl-N-ethylamino and so on can be mentioned. Particularly, dimethylamino can be mentioned.

As the "substituent" of the "optionally substituted phenyl" for $R^4$, $R^{4'}$ or $R^{4''}$, for example, those exemplarily recited as the "substituent" of the aforementioned "optionally substituted alkyl" for $R^1$ can be mentioned.

As the "substituent" of the "optionally substituted heterocyclic ring" for $R^4$, $R^{4'}$ or $R^{4''}$, for example, those exemplarily recited as the "substituent" of the aforementioned "optionally substituted alkyl" for $R^1$ can be mentioned.

As the "heterocyclic ring" of the "optionally substituted heterocyclic ring" for $R^4$, $R^{4'}$ or $R^{4''}$, for example, a 5- to 7-membered aromatic heterocyclic ring or non-aromatic heterocyclic ring optionally containing, besides carbon atoms, one or two kinds of 1 to 4 heteroatoms selected from a nitrogen atom, a sulfur atom and an oxygen atom, to be specific, pyrrolidine, piperidine, piperazine, morpholine, thiomorpholine, homopiperazine, thiophene, furan, pyrrole, imidazole, pyrazole, pyridine, pyrazine, pyrimidine, thiazole, oxazole and so on can be mentioned, preferably pyrrolidine, piperidine, piperazine and morpholine can be mentioned. The "heterocyclic ring" optionally has, for example, 1 to 3, substituents mentioned above at substitutable position(s), and when the number of the substituents is not less than 2, respective substituents may be the same or different.

As the "halogen atom" for $R^5$, for example, those exemplarily recited as the aforementioned "halogen atom" for $R^3$ can be mentioned. Particularly, fluorine is preferable.

As the "substituent" and "alkyl" of the "optionally substituted alkyl" for $R^5$, for example, those exemplarily recited as the "substituent" and "alkyl" of the aforementioned "optionally substituted alkyl" for $R^1$ can be mentioned. Particularly, methoxymethyl is preferable.

As the "alkoxy" for $R^5$, for example, those exemplarily recited as the aforementioned "alkoxy" for $R^4$, $R^{4'}$ or $R^{4''}$ can be mentioned. Particularly, methoxy is preferable.

As the "alkoxycarbonyl" for $R^5$, for example, those exemplarily recited as the aforementioned "alkoxycarbonyl" for $R^3$ can be mentioned.

As the "acyl" for $R^5$, for example, those exemplarily recited as the aforementioned "acyl" for $R^4$, $R^{4'}$ or $R^{4''}$ can be mentioned.

As the "substituent" and of the "optionally substituted alkyl" for $R^{5a}$, $R^{5a'}$ or $R^{5a''}$, for example, those exemplarily recited as the "substituent" and "alkyl" of the aforementioned "optionally substituted alkyl" for $R^1$ can be mentioned.

As the "alkylamino" for $R^5$, for example, those exemplarily recited as the aforementioned "alkylamino" for $R^3$ can be mentioned.

As the "halogen atom" for $R^6$ or $R^{6'}$, for example, those exemplarily recited as the aforementioned "halogen atom" for $R^3$ can be mentioned. Particularly, fluorine and chlorine are preferable.

As the "substituent" and "alkyl" of the "optionally substituted alkyl" for $R^6$ or $R^{6'}$, for example, those exemplarily recited as the "substituent" and "alkyl" of the aforementioned "optionally substituted alkyl" for $R^1$ can be mentioned. Particularly, trifluoromethyl can be mentioned.

As the "substituent" of the "optionally substituted alkenyl" for $R^6$ or $R^{6'}$, for example, those exemplarily recited as the "substituent" of the aforementioned "optionally substituted alkyl" for $R^1$ can be mentioned.

As the "alkenyl" of the "optionally substituted alkenyl" for $R^6$ or $R^{6'}$, for example, those exemplarily recited as the "alkenyl" of the aforementioned "optionally substituted alkenyl" for $R^4$, $R^{4'}$ or $R^{4''}$ can be mentioned.

As the "substituent" of the "optionally substituted alkynyl" for $R^6$ or $R^{6'}$, for example, those exemplarily recited as the "substituent" of the aforementioned "optionally substituted alkyl" for $R^1$ can be mentioned.

As the "alkynyl" of the "optionally substituted alkynyl" for $R^6$ or $R^{6'}$, for example, those exemplarily recited as the "alkynyl" of the aforementioned "optionally substituted alkynyl" for $R^4$, $R^{4'}$ or $R^{4''}$ can be mentioned.

As the "alkoxy" for $R^6$ or $R^{6'}$, for example, those exemplarily recited as the aforementioned "alkoxy" for $R^3$ can be mentioned.

As the "alkoxycarbonyl" for $R^6$ or $R^{6'}$, for example, those exemplarily recited as the aforementioned "alkoxycarbonyl" for $R^3$ can be mentioned.

As the "acyl" for $R^6$ or $R^{6'}$, for example, those exemplarily recited as the aforementioned "acyl" for $R^4$, $R^{4'}$, $R^{4''}$ can be mentioned.

As the "substituent" and "alkyl" of the "optionally substituted alkyl" for $R^{6a}$, $R^{6a'}$ or $R^{6a''}$, for example, those exemplarily recited as the "substituent" and "alkyl" of the aforementioned "optionally substituted alkyl" for $R^1$ can be mentioned. Particularly, methyl and ethyl are can be mentioned.

As the "substituent" of the "optionally substituted 5- to 7-membered non-aromatic heterocyclic ring" for $NR^{6a'}R^{6a''}$ in $-(C=O)NR^{6a'}R^{6a''}$ or $-SO_2NR^{6a'}R^{6a''}$, for example, those exemplarily recited as the "substituent" of the aforementioned "optionally substituted alkyl" for $R^1$ can be mentioned.

As the "non-aromatic heterocyclic ring" of the "optionally substituted 5- to 7-membered non-aromatic heterocyclic ring" for $NR^{6a'}R^{6a''}$ in $-(C=O)NR^{6a'}R^{4a''}$ or $-SO_2NR^{6a'}R^{6a''}$, for example, those exemplarily recited as the "non-aromatic heterocyclic ring" of the aforementioned "optionally substituted 5- to 7-membered non-aromatic heterocyclic ring" for $NR^{4a'}R^{4a''}$ in $-(C=O)NR^{4a'}R^{4a''}$ or $-SO_2NR^{4a'}R^{4a''}$ can be mentioned.

As the "alkylamino" for $R^6$ or $R^{6'}$, for example, those exemplarily recited as the aforementioned "alkylamino" for $R^4$, $R^{4'}$ or $R^{4''}$ can be mentioned.

As the "substituent" of the "optionally substituted phenyl" for $R^{6a}$ or $R^{4a'}$, for example, those exemplarily recited as the "substituent" of the aforementioned "optionally substituted alkyl" for $R^1$ can be mentioned.

As the "substituent" and "heterocyclic ring" of the "optionally substituted heterocyclic ring" for $R^6$ or $R^{6'}$, for example, those exemplarily recited as the "substituent" and "heterocyclic ring" of the aforementioned "optionally substituted heterocyclic ring" for $R^4$, $R^{4'}$ or $R^{4''}$ $R^1$ can be mentioned.

As the "substituent" and "alkyl" of the "optionally substituted alkyl" for $R^7$, for example, those exemplarily recited as the "substituent" and "alkyl" of the aforementioned "optionally substituted alkyl" for $R^1$ can be mentioned. Particularly, dimethyl aminomethyl is preferable.

As the "substituent" and "alkyl" of the "optionally substituted alkyl" for $R^{10}$, for example, those exemplarily recited as the "substituent" and "alkyl" of the aforementioned "optionally substituted alkyl" for $R^1$ can be mentioned. Particularly, methyl and 2-methoxyethyl can be mentioned.

As the "acyl" for $R^{10}$, for example, those exemplarily recited as the aforementioned "acyl" for $R^4$, $R^{4'}$ or $R^{4''}$ can be mentioned.

As the "alkoxycarbonyl" for $R^{10}$, for example, those exemplarily recited as the aforementioned "alkoxycarbonyl" for $R^3$ can be mentioned.

As the "substituent" and "alkyl" of the "optionally substituted alkyl" for $R^{10a}$, for example, those exemplarily recited as the "substituent" and "alkyl" of the aforementioned "optionally substituted alkyl" for $R^1$ can be mentioned.

As the "substituent" of the "optionally substituted phenyl" for $R^{10a}$, for example, those exemplarily recited as the "substituent" of the aforementioned "optionally substituted alkyl" for $R^1$ can be mentioned.

As the "aromatic heterocyclic ring" for $Ar^2$, for example, a 5- or 6-membered aromatic heterocyclic ring containing, besides carbon atoms, one or two kinds of 1 to 4 heteroatoms selected from a nitrogen atom, a sulfur atom and an oxygen atom (e.g., thiophene, furan, pyrrole, imidazole, pyrazole, pyridine, pyrazine, pyrimidine, thiazole, oxazole etc.) can be mentioned.

As the "substituent" and "alkyl" of the "optionally substituted alkyl" for $R^{11}$, for example, those exemplarily recited as the "substituent" and "alkyl" of the aforementioned "optionally substituted alkyl" for $R^1$ can be mentioned.

As the pharmaceutically acceptable salt of the compound of the formula (I), an acid addition salt with an inorganic acid or an organic acid can be mentioned.

The pharmaceutically acceptable salt of the compound of the formula (I) may be present as a water adduct, a hydrate or a solvate. Therefore, these water adduct, hydrate and solvate are also encompassed in the present invention.

An optically active form of the compound of the formula (I) is also encompassed in the present invention.

The compounds of the present invention included in the formula (I) can be synthesized by the following method.

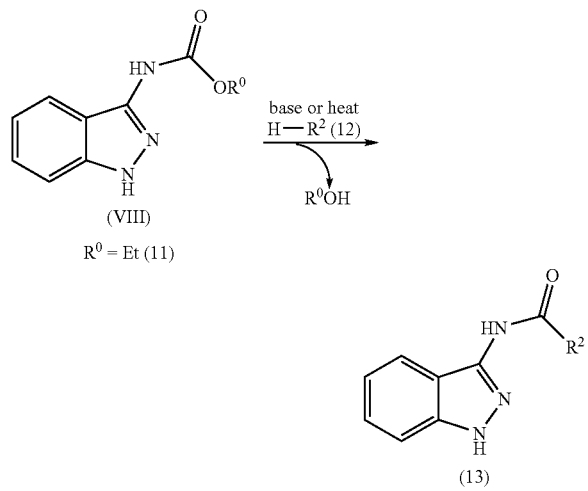

The compound of the formula (13) can be obtained by heating the compound of the formula (VIII) and the compound of the formula (12) in a suitable solvent in the presence of a base. When the base is absent, the reaction proceeds thermally by raising the reaction temperature, whereby compound (13) can be obtained. Here, the compound of the formula (12) is an amine or a salt thereof.

It is assumed that the reaction will proceed when $R^0$ in the formula (VIII) is a functional group considered to be suitable as a leaving group. $R^0$ is, for example, optionally substituted $C_{1-6}$ alkyl (e.g., methyl, ethyl, propyl etc.) or optionally substituted phenyl (e.g., phenyl, p-nitrophenyl etc.). Particularly, a compound of the formula (11) wherein $R^0$ is ethyl (i.e., ethyl 1H-indazol-3-ylcarbamate) (synthesized according to the method described in Tetrahedron, 1976, 32(4), 493.), and a compound of the formula (VIII) wherein $R^0$ is methyl are preferable.

The above-mentioned base is not particularly limited as long as it promotes the reaction, and metal alkoxides such as tertiary amine, potassium tert-butoxide and so on, guanidine such as amidine (e.g., diazabicyclo[5,4,0]undecene and so on) and so on, metal hydrides such as sodium hydride and so on, metal fluorides such as potassium fluoride and so on, a solid carrying metal fluoride and so on can be mentioned. Particularly, diazabicyclo[5,4,0]undecene (DBU) and a potassium fluoride on alumina are preferable.

The amount of the additive is generally 0.1 to 30 equivalents, preferably 0.1 to 10 equivalents, relative to the compound.

The solvent to be used for the reaction is not limited as long as it does not inhibit the reaction. Preferably, tetrahydrofuran, dimethyl sulfoxide, 1,4-dioxane, N,N-dimethylformamide and so on can be mentioned. The temperature of this reaction is generally 60° C. to 200° C., preferably 80° C. to 150° C.

While the reaction time varies depending on the temperature and the kind of the solvent, it is generally 30 min. to 8 hr.

The reaction also proceeds in the same manner even in a compound wherein the nitrogen in the pyrazole of the compound of the formula (VIII) is protected by a conventional protecting group, and a corresponding protected form of the formula (13) can be obtained, which may then be deprotected to give a compound of the formula (13). In addition, a compound wherein, in the formula (I), $R^1$ is other than a hydrogen atom can be obtained by introducing a protecting group into the pyrazole of compound of the formula (13) according to a conventional method, introducing the $R^1$ moiety of the formula (I) according to a conventional method, and then eliminating the protecting group.

After completion of the above-mentioned reaction, the object product of each reaction can be recovered from the reaction mixture according to a conventional method. For example, after the reaction mixture is concentrated, or after the solid product is removed by filtration when a solid product is present, a solvent miscible with water, such as methanol, tetrahydrofuran and so on, is added thereto to dilute the solution, which is then added to an acidic or neutral water to allow for crystal precipitation, whereby an object product is obtained. When the object product does not permit crystal precipitation, it can be obtained by washing with an organic solvent immiscible with water, such as ethyl acetate and chloroform, separating the organic layer containing the object product, drying the layer over anhydrous magnesium sulfate etc. and evaporating the solvent. The obtained object compound can be further purified as necessary by a conventional method, such as recrystallization, re-precipitation, washing with solvent, chromatography and so on.

The compound of the formula (I) obtained by the above-mentioned methods, a pharmaceutically acceptable salt thereof, a water adduct thereof, a hydrate thereof and a solvate thereof have a potent antiangiogenic action and a potent anti-cancer action, and are useful as drugs for the prophylaxis and/or treatment of cancer.

The dose is determined according to the age, body weight, general health condition, sex, diet, administration time, administration method, clearance rate, combination of drugs, level of the disease for which the patients are under treatment or in consideration of other factors. The compound of the present invention, an optical isomer thereof and a pharmaceutically acceptable salt thereof are low toxic and can be used safely. The dose thereof can be appropriately determined according to the conditions such as age, health condition, body weight and so on of patients, the conditions of the kind, administration frequency and so on of the pharmaceutical agent, if any, to be simultaneously administered or properties of the desired effect and so on. Generally, the daily dose of the active ingredient is 0.5-300 mg/kg body weight, generally 1-30 mg/kg body weight, which can be administered once or more times in divided doses, per day.

When the compound of the present invention is used as a pharmaceutical agent, a pharmaceutical composition containing the above-mentioned active ingredient and one or more kinds of formulation additives is preferably prepared and administered.

As a pharmaceutical composition suitable for oral administration, for example, tablet, capsule, powder, liquid, elixir and so on can be mentioned and, as a pharmaceutical composition suitable for parenteral administration, for example, a pharmaceutical composition in the form of a sterile liquid such as a liquid agent, a suspension and so on can be mentioned.

The kind of the formulation additives to be used for the preparation of pharmaceutical compositions is not particularly limited, and appropriate formulation additives can be selected according to the various forms of pharmaceutical compositions. The formulation additives may be solid or liquid and, for example, a solid carrier, a liquid carrier and so on can be used.

As an exemplary solid carrier, a conventional gelatin-type capsule can be used. Moreover, for example, the active ingredient can be formed into a tablet together with one or more kinds of formulation additives, or without formulation additives, or can be formed into and packaged as a powder. These capsules, tablets and powders can generally contain 5-95 wt %, preferably 5-90 wt %, of the active ingredient relative to the total weight of the preparation, where the administration unit preferably contains 5-500 mg, preferably 25-250 mg, of the active ingredient. As the liquid carrier, water, oil derived from animal or plant, such as petroleum, peanut oil, soy bean oil, mineral oil, sesame oil and so on, or synthetic oil is used.

In general, moreover, saline, dextrol or similar sucrose solution, and glycols such as ethylene glycol, propylene glycol, polyethylene glycol and so on are preferable as liquid carriers. Particularly, in the case of an injection using physiological saline, it can be prepared to generally contain 0.5-20% by weight, preferably 1-10% by weight, of the active ingredient.

EXAMPLES

The present invention is explained in more detail in the following by referring to Starting Material Synthetic Examples, Examples and Pharmacological Experimental Examples, which are not to be construed as limitative.

Starting Material Synthetic Example 1 tert-Butyl 1,3,4,9-tetrahydro-1H-β-carboline-2-carboxylate (synthesized according to the method described in J. Med. Chem., 45, 11, 2002, 2197-2206, 800 mg) was dissolved in tetrahydrofuran (10 ml), sodium hydride (60 wt % in oil, 130 mg) was added, and the mixture was stirred at room temperature for 15 min. Then, 2-chloroethyl-methylether (Aldrich Co., 322 µl) was added, and the mixture was stirred with heating at 70° C. for 2 hr. After cooling the reaction mixture, water was added, and the mixture was extracted with ethyl acetate. The organic layer was dried, and the solvent was evaporated under reduced pressure. The obtained residue was dissolved in ethyl acetate, a 4N hydrochloric acid-ethyl acetate solution was added, and the mixture was stirred at room temperature for 2 hr. The precipitated solid was collected by filtration, washed with ethyl acetate, and dried to give 9-(2-methoxyethyl)-2,3,4,9-tetrahydro-1H-β-carboline hydrochloride (662 mg, yield 84%).

$^1$H-NMR(300 MHz, DMSO-$d_6$)δ(ppm): 2.88-2.97(2H, m), 3.19(3H, s), 3.34-3.42(2H, m), 3.52-3.59(2H, m), 4.20-4.48(4H, m), 7.00-7.21(2H, m), 7.44-7.52(2H, m), 9.78(2H, brs).

Starting Material Synthetic Example 2

By a similar operation as in Starting Material Synthetic Example 1 and using dimethylformamide as a solvent, 9-(2-morpholin-4-ylethyl)-2,3,4,9-tetrahydro-1H-β-carboline dihydrochloride (377 mg, yield 36%) was obtained from 1,3,4,9-tetrahydro-1H-β-carboline-2-carboxylic acid tert-butyl ester (synthesized according to the method described in J. Med. Chem., 45, 11, 2002, 2197-2206, 800 mg) and N-(2-chloroethyl)-morpholine hydrochloride (Aldrich Co., 659 mg).

$^1$H-NMR(300 MHz, DMSO-$d_6$)δ(ppm): 2.90-3.57(10H, m), 3.78-4.08(4H, m), 4.52(2H, s), 4.60-4.74(2H, m), 7.06-7.27(2H, m), 7.51(1H, d, J=7.8 Hz), 7.68(1H, d, J=7.8 Hz)9.86(2H, brs), 12.09(1H, brs).

Starting Material Synthetic Example 3

6-Fluoroindole (Aldrich Co., 1.00 g) and N,N-dimethylnitroethylene (LANCASTER Co., 859 mg) were dissolved in trifluoroacetic acid (7.4 ml), and the mixture was stirred at room temperature for 1 hr. The reaction mixture was poured into a saturated aqueous sodium hydrogen carbonate solution. The precipitated solid was collected by filtration, washed with water, and dried to give 6-fluoro-3-[(E)-2-nitrovinyl]-1H-indole (1.48 g, yield 97%).

$^1$H-NMR(400 MHz, DMSO-$d_6$)δ(ppm): 7.08(1H, ddd, J=9.4 Hz, 8.6 Hz, 2.4 Hz), 7.33(1H, dd, J=9.4 Hz, 2.4 Hz), 8.01(1H, dd, J=8.6 Hz, 5.5 Hz), 8.04(1H, d, J=13.3 Hz), 8.25(1H, s), 8.39(1H, d, J=13.3 Hz), 12.16(1H, brs).

Aluminum lithium hydride (1.36 g) was suspended in tetrahydrofuran (72 ml), 6-fluoro-3-[(E)-2-nitrovinyl]-1H-indole (1.48 g) was dissolved in tetrahydrofuran (20 ml) and added dropwise under ice-cooling, and the mixture was stirred at 60° C. for 1 hr. Under ice-cooling, excess aluminum lithium hydride was decomposed with ice water, ethyl acetate was added, and the mixture was filtered through a celite (trademark) filter. A 1N aqueous sodium hydroxide solution was added to the filtrate, pH was adjusted to not less than 11, and the mixture was extracted with ethyl acetate. The organic layer was washed with saturated brine, and dried over anhydrous sodium sulfate. The solvent was evaporated under reduced pressure to give a brown oil. The oil was purified by amine coating silica gel column chromatography (elution solvent:ethyl acetate-ethyl acetate-methanol (10:1)) to give 6-fluorotryptamine (1.24 g, yield 97%).

$^1$H-NMR(400 MHz, DMSO-$d_6$)δ(ppm): 1.18(2H, brs), 2.69-2.76(2H, m), 2.76-2.83(2H, m), 6.82(1H, ddd, J=10.2 Hz, 8.6 Hz, 2.4 Hz), 7.09(1H, dd, J=10.2 Hz, 2.4 Hz), 7.12(1H, d, J=1.3 Hz), 7.49(1H, dd, J=8.6 Hz, 5.5 Hz), 10.86(1H, s).

6-Fluorotryptamine (0.71 g) was dissolved in tetrahydrofuran (30 ml), a 4N hydrochloric acid-ethyl acetate solution (1.2 ml) was added dropwise, and the mixture was stirred at room temperature. The solvent was evaporated under reduced pressure. Glyoxylic acid monohydrate (Aldrich Co., 403 mg), a 1N potassium hydroxide solution (3.98 ml) and water (80 ml) were added to the obtained residue, and the mixture was stirred with heating at 80° C. for 1.5 hr. After ice-cooling, the precipitate was collected by filtration and washed with water to give a pale-brown solid. Water (80 ml) and concentrated hydrochloric acid (2 ml) were added to the obtained solid, and the mixture was stirred with heating at 80° C. for 1 hr. Concentrated hydrochloric acid (2 ml) was further added, and the mixture was heated under reflux for 1 hr. The insoluble material was hot filtrated, and the filtrate was adjusted to pH 12 or above with a 6N aqueous sodium hydroxide solution. The precipitated solid was collected by filtration, washed with water, and dried to give 7-fluoro-2,3,4,9-tetrahydro-1H-β-carboline (516 mg, yield 68%).

$^1$H-NMR(400 MHz, DMSO-$d_6$)δ(ppm): 2.36(1H, brs), 2.56(2H, t, J=5.5 Hz), 2.95(2H, t, J=5.5 Hz), 3.82(2H, s), 6.77(1H, ddd, J=10.2 Hz, 8.6 Hz, 2.4 Hz), 7.04(1H, dd, J=10.2 Hz, 2.4 Hz), 7.31(1H, dd, J=8.6 Hz, 5.5 Hz), 10.76(1H, s).

Starting Material Synthetic Example 4

By a similar operation as in Starting Material Synthetic Example 3, 6-fluoro-2,3,4,9-tetrahydro-1H-β-carboline (516 mg, yield 42%) was obtained from 5-fluoroindole (Aldrich Co., 1.00 g).

$^1$H-NMR(400 MHz, DMSO-$d_6$)δ(ppm): 2.54(1H, brs), 2.55(2H, t, J=5.5 Hz), 2.95(2H, t, J=5.5 Hz), 3.83(2H, s), 6.81(1H, m), 7.08(1H, dd, J=10.2 Hz, 2.4 Hz), 7.23(1H, dd, J=8.6 Hz, 4.7 Hz), 10.75(1H, s).

Starting Material Synthetic Example 5

By a similar operation as in Starting Material Synthetic Example 3, 6-chloro-2,3,4,9-tetrahydro-1H-β-carboline (573 mg, yield 64%) was obtained from 5-chlorotryptamine hydrochloride (Tokyo Chemical Industry CO., LTD., 1.00 g).
$^1$H-NMR(400 MHz, DMSO-$d_6$)δ(ppm): 2.40(1H, brs), 2.56(2H, t, J=5.5 Hz), 2.95(2H, t, J=5.5 Hz), 3.84(2H, s), 6.98(1H, dd, J=8.6 Hz, 2.4 Hz), 7.26(1H, d, J=8.6 Hz), 7.36 (1H, d, J=2.4 Hz), 10.87(1H, s).

Starting Material Synthetic Example 6

By a similar operation as in Starting Material Synthetic Example 3, 6-hydroxy-2,3,4,9-tetrahydro-1H-β-carboline (0.77 g, yield 87%) was obtained from 5-hydroxytryptamine hydrochloride (Aldrich Co., 1.0 g).
$^1$H-NMR(400 MHz, DMSO-$d_6$)δ(ppm): 2.48-2.54(3H, m), 2.95(2H, t, J=5.5 Hz), 3.80(2H, s), 6.49(1H, dd, J=8.6 Hz, 2.4 Hz), 6.65(1H, d, J=2.4 Hz), 7.02(1H, d, J=8.6 Hz), 8.49 (1H, brs), 10.27(1H, s). MS(ESI)m/z:189[M+H]$^+$.

Starting Material Synthetic Example 7

By a similar operation as in Starting Material Synthetic Example 3, 7-chloro-2,3,4,9-tetrahydro-1H-β-carboline (708 mg, yield 77%) was obtained from 6-chloroindole (Aldrich Co., 1.00 g).
$^1$H-NMR(400 MHz, DMSO-$d_6$)δ(ppm): 2.41(1H, brs), 2.57(2H, t, J=5.5 Hz), 2.96(2H, t, J=5.5 Hz), 3.83(2H, s), 6.93(1H, dd, J=8.6 Hz, 1.6 Hz), 7.29(1H, d, J=1.6 Hz), 7.34 (1H, d, J=8.6 Hz), 10.84(1H, s).

Starting Material Synthetic Example 8

By a similar operation as in Starting Material Synthetic Example 3, 7-(trifluoromethyl)-2,3,4,9-tetrahydro-1H-β-carboline (184 mg, yield 14%) was obtained from 6-(trifluoromethyl)indole (LANCASTER Co., 1.02 g).
$^1$H-NMR(400 MHz, DMSO-$d_6$)δ(ppm): 2.40(1H, brs), 2.62(2H, t, J=5.5 Hz), 2.98(2H, t, J=5.5 Hz), 3.90(2H, s), 7.20-7.56(2H, m), 7.59(1H, s), 11.16(1H, s).

Starting Material Synthetic Example 9

By a similar operation as in Starting Material Synthetic Example 3, 5-fluoro-2,3,4,9-tetrahydro-1H-β-carboline (379 mg, yield 23%) was obtained from 4-fluoroindole (Aldrich Co., 1.19 g).
$^1$H-NMR(400 MHz, DMSO-$d_6$)δ(ppm): 2.38(1H, brs), 2.72(2H, t, J=5.5 Hz), 2.95(2H, t, J=5.5 Hz), 6.65(1H, m), 6.92(1H, dt, J=7.8 Hz, 5.5 Hz), 7.08(1H, d, J=7.8 Hz), 10.95 (1H, s).

Starting Material Synthetic Example 10

By a similar operation as in Starting Material Synthetic Example 3, 5-chloro-2,3,4,9-tetrahydro-1H-β-carboline (241 mg, yield 19%) was obtained from 4-chloroindole (Aldrich Co., 954 mg).
$^1$H-NMR(400 MHz, DMSO-$d_6$)δ(ppm): 2.86-3.40(5H, m), 3.87(2H, s), 6.88-7.25(3H, m), 11.00(1H, s).

Starting Material Synthetic Example 11

By a similar operation as in Starting Material Synthetic Example 3, 8-methyl-2,3,4,9-tetrahydro-1H-β-carboline (530 mg, yield 38%) was obtained from 7-methylindole (Aldrich Co., 1.00 g).
$^1$H-NMR(400 MHz, DMSO-$d_6$)δ(ppm): 2.37(1H, brs), 2.40(3H, s), 2.57(2H, t, J=5.5 Hz), 2.96(2H, t, J=5.5 Hz), 3.86(2H, s), 6.98(1H, dd, J=8.6 Hz, 2.4 Hz), 6.76-6.86(2H, m), 7.16(1H, d, J=7.8 Hz), 10.51(1H, s).

Starting Material Synthetic Example 12

By a similar operation as in Starting Material Synthetic Example 3, 6-methyl-2,3,4,9-tetrahydro-1H-β-carboline (800 mg, yield 87%) was obtained from 5-methyltryptamine hydrochloride (Aldrich Co., 1.04 g).
$^1$H-NMR(400 MHz, DMSO-$d_6$)δ(ppm): 2.35(3H, s), 2.69 (2H, t, J=5.5 Hz), 3.14(2H, t, J=5.5 Hz), 4.02(2H, s), 6.83-6.88(1H, m), 7.14-7.20(2H, m), 10.62(1H, s).

Starting Material Synthetic Example 13

By a similar operation as in Starting Material Synthetic Example 3, 7-chloro-6-fluoro-2,3,4,9-tetrahydro-1H-β-carboline (559 mg, yield 61%) was obtained from 6-chloro-5-fluoroindole (synthesized according to the method described in Tetrahedron Lett., 43, 42, 2002, 7581-7584, 1.82 g).
$^1$H-NMR(400 MHz, DMSO-$d_6$)δ(ppm): 2.59(2H, t, J=5.5 Hz), 3.00(2H, t, J=5.5 Hz), 3.20-4.00(1H, m), 3.89(2H, s), 7.30-7.44(2H, m), 10.94(1H, s).

Starting Material Synthetic Example 14

A mixture of 5-amino-2-chloro-4-nitrobenzotrifluoride (synthesized according to the method described in J. Org. Chem., 60, 18, 1995, 5838-5842, 24.9 g) and 48% aqueous hydrogen bromide (400 ml) was ice-cooled. Sodium nitrite (12.9 g) was dissolved in a small amount of water and added dropwise thereto. The reaction mixture was stirred for 4 hr while warming from −5° C. to 15° C., ice-cooled and alkalified with a 6N aqueous sodium hydroxide solution. The precipitated solid was collected by filtration and washed with water to give a brown solid. The solid was purified by silica gel column chromatography (elution solvent:ethyl acetate-hexane (1:50)) to give 5-bromo-2-chloro-4-nitrobenzotrifluoride (17.7 g, yield 56%).
$^1$H-NMR(400 MHz, DMSO-$d_6$)δ(ppm): 8.42(1H, s), 8.54 (1H, s).
A mixture of reduced iron (17.7 g), acetic acid (290 ml) and water (145 ml) was stirred with heating at 60° C. for 15 min, 5-bromo-2-chloro-4-nitrobenzotrifluoride (17.7 g) dissolved in 1,4-dioxane (100 ml) was added thereto, and the mixture was stirred with heating at 60° C. for 30 min. The reaction mixture was ice-cooled, ethyl acetate (700 ml) was added and the mixture was stirred at room temperature, The reaction mixture was filtered through a celite (trademark) filter. The filtrate was washed three times with a 1N aqueous sodium hydroxide solution and then with saturated brine, and dried over anhydrous sodium sulfate. The solvent was evaporated under reduced pressure to give 2-bromo-5-chloro-4-(trifluoromethyl)aniline (17.1 g, yield 100%).
$^1$H-NMR(400 MHz, DMSO-$d_6$)δ(ppm): 6.34(2H, brs), 6.97(1H, s), 7.71(1H, s).
A mixture of 2-bromo-5-chloro-4-(trifluoromethyl)aniline (17.1 g), trimethylsilylacetylene (14.8 ml), bistriphenylphosphinepalladium dichloride (816 mg) and triethylamine (115 ml) was stirred at 60° C. for 9 hr. The reaction mixture was ice-cooled, diethyl ether was added and the mixture was filtered through a celite (trademark) filter. The filtrate was evaporated under reduced pressure to give a brown oil. The oil was purified by silica gel column chromatography (elution solvent:ethyl acetate-hexane (1:20-1:10)) to give 5-chloro-4-(trifluoromethyl)-2-[(trimethylsilyl)ethynyl]aniline (16.5 g, yield 92%).

$^1$H-NMR(400 MHz, DMSO-$d_6$)δ(ppm): 0.24(9H, s), 6.27 (2H, brs), 6.94(1H, s), 7.49(1H, s).

A mixture of 5-chloro-4-(trifluoromethyl)-2-[(trimethylsilyl)ethynyl]aniline (16.5 g), copper(I) iodide (20.4 g) and dimethylformamide (100 ml) was stirred at room temperature for 10 min and then stirred with heating at 100° C. for 2.5 hr. The reaction mixture was allowed to cool, diethyl ether was added and the mixture was stirred at room temperature. The reaction mixture was filtered through a celite (trademark) filter, and the filtrate was washed with water and saturated brine, dried over anhydrous sodium sulfate. The solvent was evaporated under reduced pressure to give a brown oil. The oil was purified by silica gel column chromatography (elution solvent:ethyl acetate-hexane (1:5-1:3)) to give 6-chloro-5-(trifluoromethyl)-1H-indole (5.75 g, yield 46%).

$^1$H-NMR(400 MHz, DMSO-$d_6$)δ(ppm): 6.64(1H, s), 7.57 (1H, s), 7.68(1H, s), 8.09(1H, s), 11.62(1H, s).

Phosphorus oxychloride (1.83 ml) was added dropwise to dimethylformamide (16 ml) under ice-cooling, and the mixture was stirred at 0° C. for 20 min. 6-Chloro-5-(trifluoromethyl)-1H-indole (3.24 g) dissolved in dimethylformamide (10 ml) was added to the reaction mixture, and the mixture was stirred at 0° C. for 3 hr. Water was added to the reaction mixture, and the mixture was stirred at room temperature for 3 hr, and the mixture was alkalified with a 1N aqueous sodium hydroxide solution. The precipitated solid was collected by filtration, washed with water and dried to give 6-chloro-5-(trifluoromethyl)indole-3-carbaldehyde (3.25 g, yield 89%).

$^1$H-NMR(400 MHz, DMSO-$d_6$)δ(ppm): 7.85(1H, s), 8.49-8.53(2H, m), 10.00(1H, s), 12.53(1H, s).

Nitromethane (20 ml) and ammonium acetate (1.6 g) were added to 6-chloro-5-(trifluoromethyl)indole-3-carbaldehyde (3.25 g) and the mixture was heated under reflux for 1 hr. The reaction mixture was allowed to cool, and the precipitated solid was collected by filtration, washed with methanol-water (1:1) and dried to give a brown solid. This solid was washed in a suspension state with diethyl ether, collected by filtration and dried to give 6-chloro-3-[(E)-2-nitrovinyl]-5-(trifluoromethyl)-1H-indole (1.86 g, yield 49%).

$^1$H-NMR(400 MHz, DMSO-$d_6$)δ(ppm): 7.82(1H, s), 8.18 (1H, d, J=13.3 Hz), 8.43(1H, s), 8.47(1H, s), 8.47(1H, d, J=13.3 Hz), 12.54(1H, brs).

Then, by a similar operation as in Starting Material Synthetic Example 3, 7-chloro-6-(trifluoromethyl)-2,3,4,9-tetrahydro-1H-β-carboline (512 mg, yield 29%) was obtained from 6-chloro-3-[(E)-2-nitrovinyl]-5-(trifluoromethyl)-1H-indole (1.86 g).

$^1$H-NMR(400 MHz, DMSO-$d_6$)δ(ppm): 2.86(2H, t, J=5.5 Hz), 3.29(2H, t, J=5.5 Hz), 4.22(2H, s), 7.66(1H, s), 7.96(1H, s), 11.62(1H, s).

Starting Material Synthetic Example 15

A mixture of 2-iodothiophene (Aldrich Co., 1.0 g), 1-(tert-butoxycarbonyl)piperazine (Aldrich Co. (hereafter the same), 1.06 g), copper(I) iodide (45 mg), ethylene glycol (530 μl), potassium phosphate (2.02 g) and 2-propanol (5 ml) was heated under reflux for 20 hr. Ethyl acetate was added, and the mixture was filtered through a Celite (trademark) filter. The filtrate was washed 3 times with 28% aqueous ammonia, and then washed with saturated brine. The solvent was evaporated under reduced pressure to give a brown solid. The solid was purified by silica gel column chromatography (elution solvent: ethyl acetate-hexane (7:3)) to give 4-(2-thienyl)piperazine-1-carboxylic acid tert-butyl ester (984 mg, yield 77%).

$^1$H-NMR(300 MHz, DMSO-$d_6$)δ(ppm): 1.42(9H, s), 3.01 (4H, m), 3.45(4H, m), 6.18-6.22(1H, m), 6.74-6.78(2H, m).

4-(2-Thienyl)piperazine-1-carboxylic acid tert-butyl ester (700 mg) was dissolved in ethyl acetate (4 ml), a 4N hydrochloric acid-ethyl acetate solution (4 ml) was added, and the mixture was stirred at room temperature for 1.5 hr. The precipitated solid was collected by filtration, washed with ethyl acetate and dried to give 1-(2-thienyl)piperazine hydrochloride (532 mg, yield 98%).

$^1$H-NMR(300 MHz, DMSO-$d_6$)δ(ppm): 3.17-3.36(8H, m), 6.28(1H, d, J=3.5 Hz), 6.75-6.88(2H, m), 9.51(1H, brs).

Starting Material Synthetic Example 16

4-Bromobenzyl bromide (Aldrich Co., 2.0 g) and morpholine (0.73 ml) were dissolved in acetonitrile (15 ml), potassium carbonate (1.3 g) was added, and the mixture was heated under reflux for 4 hr. The insoluble material was filtered off, and the filtrate was evaporated under reduced pressure. The obtained residue was purified by silica gel column chromatography (elution solvent: hexane-ethyl acetate (5:1)) to give 4-(4-bromobenzyl)morpholine (1.55 g). 4-(4-Bromobenzyl)morpholine (1.55 g), 1-(tert-butoxycarbonyl)piperazine (1.27 g), 2-(di-tert-butylphosphino)biphenyl (37 mg), tris(dibenzylideneacetone)dipalladium (57 mg) and sodium tert-butoxide (1.2 g) were added to toluene (13 ml), and the mixture was heated under reflux for 5 hr. The insoluble material was filtered through a Celite (trademark) filter, and the filtrate was evaporated under reduced pressure. The obtained residue was purified by silica gel column chromatography. The obtained 4-[4-(morpholine-4-ylmethyl)phenyl]piperazine-1-carboxylic acid tert-butyl ester was dissolved in dichloromethane, trifluoroacetic acid was added and the mixture was stirred overnight at room temperature. The mixture was neutralized with an aqueous sodium hydroxide solution, and extracted with dichloromethane. The organic layer was dried and the solvent was evaporated under reduced pressure to give 4-(4-piperazin-1-ylbenzyl)morpholine (1.06 g, yield 51%).

$^1$H-NMR(300 MHz, DMSO-$d_6$)δ(ppm): 2.28(4H, t, J=4.2 Hz), 2.76-2.84(4H, m), 2.95-3.02(4H, m), 3.05(1H, brs), 3.52 (4H, t, J=4.5 Hz), 6.83(2H, d, J=8.4 Hz), 7.09(2H, d, J=8.4 Hz).

Starting Material Synthetic Example 17

By a similar operation as in Starting Material Synthetic Example 16, 4-[4-fluoro-3-(trifluoromethyl)phenyl]piperazine-1-carboxylic acid tert-butyl ester was synthesized from 5-bromo-2-fluorobenzotrifluoride (Aldrich Co., 1.5 g) and 1-(tert-butoxycarbonyl)piperazine (1.38 g). These were dissolved in ethyl acetate, 4N hydrochloric acid-ethyl acetate was added, and the mixture was stirred at room temperature for 6 hr. The precipitated solid was collected by filtration and dried to give 1-[4-fluoro-3-(trifluoromethyl)phenyl]piperazine hydrochloride (1.31 g, yield 75%).

$^1$H-NMR(300 MHz, DMSO-$d_6$)δ(ppm): 3.17-3.22(4H, m), 3.40-3.46(4H, m), 7.22-7.45(3H, m), 9.46(2H, brs).

Starting Material Synthetic Example 18

By a similar operation as in Starting Material Synthetic Example 17, 1-[4-methoxy-3-(trifluoromethyl)phenyl]piperazine hydrochloride (1.0 g, yield 86%) was obtained from 5-bromo-2-methoxybenzotrifluoride (LANCASTER Co., 1.0 g) and 1-(tert-butoxycarbonyl)piperazine (840 mg).

$^1$H-NMR(300 MHz, DMSO-d$_6$)δ(ppm): 3.18-3.23(4H, m), 3.28-3.35(4H, m), 7.15-7.32(3H, m), 9.31(2H, brs).

Starting Material Synthetic Example 19

2-Amino-4-(trifluoromethyl)thiazole (Wako Pure Chemical Industries, Ltd., 500 mg) was added to 48% aqueous hydrogen bromide (6 ml) and, under ice-cooling, sodium nitrite (266 mg) dissolved in water (1 ml) was added dropwise thereto. The mixture was stirred at 0° C. for 1 hr. A sodium hydrogen sulfite aqueous solution, and then an aqueous sodium hydroxide solution were added, and the mixture was extracted with diethyl ether. The organic layer was dried and the solvent was evaporated under reduced pressure. The obtained residue was purified by silica gel column chromatography (elution solvent: ethyl acetate-hexane (1:9)) to give 2-bromo-4-(trifluoromethyl)thiazole (167 mg, yield 24%).

$^1$H-NMR(300 MHz, DMSO-d$_6$)δ(ppm): 8.55(1H, s).

By a similar operation as in Starting Material Synthetic Example 17, 1-[4-(trifluoromethyl)-1,3-thiazol-2-yl]piperazine hydrochloride (194 mg, yield 53%) was obtained from 2-bromo-4-(trifluoromethyl)thiazole (309 mg) and 1-(tert-butoxycarbonyl)piperazine (300 mg).

$^1$H-NMR(300 MHz, DMSO-d$_6$)δ(ppm): 3.19-3.24(4H, m), 3.66-3.75(4H, m), 7.68(1H, s), 9.57(2H, brs).

Starting Material Synthetic Example 20

By a similar operation as in Starting Material Synthetic Example 17, 1-[3-fluoro-5-(trifluoromethyl)phenyl]piperazine hydrochloride (951 mg, yield 81%) was obtained from 3-bromo-5-fluorobenzotrifluoride (Aldrich Co., 1.0 g) and 1-(tert-utoxycarbonyl)piperazine (920 mg).

$^1$H-NMR(300 MHz, DMSO-d$_6$)δ(ppm): 3.00-3.65(8H, m), 6.80-7.19(3H, m), 9.16(2H, brs)

Starting Material Synthetic Example 21

Under ice-cooling, 1-chloromethyl-4,9-dihydro-3H-β-carboline hydrochloride (synthesized according to the method described in J. Med. Chem., 34, 8, 1991, 2624-2633, 400 mg) was added to a mixture of morpholine (684 mg) and methanol (4.5 ml), and the mixture was stirred at room temperature for 6 hr. Under ice-cooling, sodium borohydride (119 mg) was added, and the mixture was stirred at room temperature for 16.5 hr. The reaction mixture was alkalified with a 1N aqueous sodium hydroxide solution, and the mixture was extracted with chloroform. The organic layer was washed with saturated brine and dried over anhydrous sodium sulfate. The solvent was evaporated under reduced pressure to give a brown oil. The oil was purified by silica gel column chromatography (elution solvent: chloroform-methanol (20:1)) to give 1-(morpholine-4-ylmethyl)-2,3,4,9-tetrahydro-1H-β-carboline (353 mg, yield 83%).

$^1$H-NMR(400 MHz,CDCl$_3$)δ(ppm): 2.47-2.55(2H, m), 2.58-2.84(7H, m), 3.01-3.10(1H, m), 3.37-3.45(1H, m), 3.80-3.86(1H, m), 4.20-4.27(1H, m), 7.06-7.18(2H, m), 7.32-7.37 (1H, m), 7.47-7.52(1H, m), 9.28(1H, brs).

Starting Material Synthetic Example 22

By a similar operation as in Starting Material Synthetic Example 21 and adding triethylamine (1.28 ml), dimethyl(2,3,4,9-tetrahydro-1H-β-carboline-1-ylmethyl)amine (305 mg, yield 72%) was obtained from dimethylamine hydrochloride (751 mg) and 1-chloromethyl-4,9-dihydro-3H-β-carboline hydrochloride (synthesized according to the method described in J. Med. Chem., 34, 8, 1991, 2624-2633, 470 mg).

$^1$H-NMR(400 MHz,CDCl$_3$)δ(ppm): 2.40(6H, s), 2.48-2.54(1H, m), 2.60-2.68(1H, m), 2.69-2.90(2H, m), 3.02-3.11 (1H, m), 3.37-3.45(1H, m), 4.15-4.23(1H, m), 7.04-7.51(4H, m), 9.50(1H, brs).

Starting Material Synthetic Example 23

To a mixture of 1-(tert-butoxycarbonyl)-1,2,5,6-tetrahydropyridine-3-carboxylic acid (synthesized according to the method described in Bioorg. Med. Chem., 8, 5, 2000, 1041-1058, 3.9 g), triethylamine (2.87 ml) and benzene (12 ml) was added diphenylphosphoryl azide (Aldrich Co., 4.44 ml) under ice-cooling, and the mixture was stirred at 0° C. for 1 hr. The reaction mixture was passed through a silica gel filter, and the filtrate was evaporated under reduced pressure to give a pale-yellow oil. Toluene (20 ml) was added to the oil, and the mixture was heated under reflux for 2 hr. The solvent was evaporated under reduced pressure. Dichloromethane (35 ml) and lead tetracetate (5.70 g) were added to the obtained residue. Thereafter, 1-aminobenzotriazole (Aldrich Co., 1.54 g) was dissolved in dichloromethane (15 ml) was added thereto. The mixture was stirred at room temperature for 30 min. The reaction mixture was filtered, and the filtrate was evaporated under reduced pressure. The obtained residue was purified by silica gel column chromatography to give 6-oxo-1,4,5,6-tetrahydrobenzo[c]-1,7-naphthyridine-3(2H)-carboxylic acid tert-butyl ester (1.14 g, yield 33%).

$^1$H-NMR(400 MHz, DMSO-d$_6$)δ(ppm): 1.44(9H, s), 2.68 (2H, t, J=5.5 Hz), 3.65(2H, t, J=5.5 Hz), 4.31(2H, s), 7.45-8.23(4H, m), 11.24(1H, brs).

6-Oxo-1,4,5,6-tetrahydrobenzo[c]-1,7-naphthyridine-3 (2H)-carboxylic acid tert-butyl ester (1.13 g) was added to tetrahydrofuran (30 ml) and dissolved by stirring the mixture at 60° C. 4N Hydrochloric acid-ethyl acetate (20 ml) was added, and the mixture was stirred with heating at 60° C. for 1 hr. The reaction mixture was ice-cooled, and the precipitated solid was collected by filtration, washed with ethyl acetate and dried to give 1,3,4,5-tetrahydrobenzo[c]-1,7-naphthyridin-6(2H)-one (884 mg, yield 90%).

$^1$H-NMR(400 MHz, DMSO-d$_6$)δ(ppm): 2.87-2.95(2H, m), 3.38-3.47(2H, m), 4.04(2H, s), 7.52-8.25(4H, m), 9.69 (2H, brs), 11.37(1H, brs).

Starting Material Synthetic Example 24 bis(2-Chloroethyl)amine hydrochloride (Tokyo Chemical Industry CO., LTD., 25.2 g) was suspended in methylene chloride (280 ml), and the suspension was cooled to 0° C. Pyridine (24 ml) and p-toluenesulfonyl chloride (28.3 g) were added, and the mixture was stirred at room temperature for 4 hr. After completion of the reaction, a saturated aqueous sodium hydrogencarbonate solution was added and the mixture was extracted with methylene chloride. The organic layer was washed with 1N aqueous hydrochloric acid and water and dried. The solvent was evaporated under reduced pressure. The obtained residue was purified by silica gel column chromatography (elution solvent: hexane-ethyl acetate (15:1-5:1)) to give N,N-bis(2-chloroethyl)-4-methylbenzenesulfoneamide (30.0 g, yield 71%).

$^1$H-NMR(300 MHz, DMSO-d$_6$)δ(ppm): 2.41(3H, s), 3.45 (4H, t, J=6.9 Hz), 3.72(4H, t, J=6.9 Hz), 7.44(2H, d, J=8.2 Hz), 7.75(2H, d, J=8.2 Hz).

Starting Material Synthetic Example 25

By a similar operation as in Starting Material Synthetic Example 24, N,N-bis(2-bromoethyl)-4-methylbenzenesulfoneamide (7.7 g, yield 61%) was obtained from bis(2-bromoethyl)amine hydrobromide (synthesized according to the method described in J. Med. Chem., 43, 16, 2000, 3157-3167, 10.2 g). $^1$H-NMR(300 MHz, DMSO-$d_6$)δ(ppm): 2.40(3H, s), 3.47-3.60(8H, m), 7.44(2H, d, J=8.2 Hz), 7.75(2H, d, J=8.2 Hz).

Starting Material Synthetic Example 26 bis(2-Chloroethyl)amine hydrochloride (Tokyo Chemical Industry CO., LTD., 3.0 g) was dissolved in acetone (50 ml), potassium carbonate (3.0 g) and ethyl chloroformate (2.4 ml) were added, and the mixture was heated under reflux for 4 hr. After completion of the reaction, the mixture was cooled to room temperature, and the solid was filtered off. The filtrate was evaporated under reduced pressure to give ethyl bis(2-chloroethyl)carbamate (3.7 g, yield 100%).
$^1$H-NMR(300 MHz, CDCl$_3$)δ(ppm): 1.28(3H, t, J=7.1 Hz), 3.63-3.67(8H, m), 4.17(2H, q, J=7.1 Hz).

Starting Material Synthetic Example 27 bis(2-Chloroethyl)amine hydrochloride (Tokyo Chemical Industry CO., LTD., 1.0 g) was added to a mixture of diethyl ether (15 ml) and water (15 ml). Potassium carbonate (0.85 g) and di-tert-butyl bicarbonate (1.6 g) were added, and the mixture was stirred at room temperature for 5 hr. After completion of the reaction, the organic layer was separated. The aqueous layer was extracted with diethyl ether. The organic layers were combined and dried. The solvent was evaporated under reduced pressure to give tert-butyl bis(2-chloroethyl)carbamate (0.83 g, yield 61%).
$^1$H-NMR(300 MHz, DMSO-$d_6$)δ(ppm): 1.48(9H, s), 3.57-3.62(4H, m), 3.74-3.78(4H, m).

Starting Material Synthetic Example 28

Isonipecotic acid amide (Tokyo Chemical Industry CO., LTD., 2.1 g) was dissolved in methylene chloride (50 ml). The mixture was cooled to 0° C., pyridine (4 ml) and trifluoroacetic acid anhydride (5.6 ml) were added, and the mixture was stirred for 8 hr. After completion of the reaction, a saturated aqueous sodium hydrogencarbonate solution was added, and the mixture was extracted with methylene chloride. The organic layer was washed with water, and dried. The solvent was evaporated under reduced pressure. The obtained residue was dissolved in diethyl ether (34 ml) and cooled to 0° C. A 2N aqueous sodium hydroxide solution (34 ml) was added di-tert-Butyl bicarbonate (7.2 g) dissolved in diethyl ether (10 ml) was added, and the mixture was stirred at room temperature for 12 hr. After completion of the reaction, the reaction mixture was partitioned by adding water. The organic layer was washed with water, and dried. The solvent was evaporated under reduced pressure to give 4-cyanopiperidine-1-carboxylic acid tert-butyl ester (3.1 g, yield 88%).
$^1$H-NMR(300 MHz, DMSO-$d_6$)δ(ppm): 1.39(9H, s), 1.54-1.67(2H, m), 1.74-1.87(2H, m), 2.93-3.20(3H, m), 3.50-3.57(2H, m).

Starting Material Synthetic Example 29

4-Fluorobenzyl cyanide (Aldrich Co., 2.5 g) was dissolved in dimethylsulfoxide (50 ml), and sodium amide (1.45 g) was added thereto. While stirring with heating at 50° C., the compound (5 g) of Starting Material Synthetic Example 24 was added, and the mixture was stirred for 6 hr. After completion of the reaction, an aqueous ammonium chloride solution was added, and the mixture was extracted with methylene chloride. The organic layer was dried and the solvent was evaporated under reduced pressure. The obtained residue was purified by silica gel column chromatography (elution solvent: hexane-ethyl acetate (10:1-2:1)). To the intermediate was added a hydrobromide saturated acetic acid solution (5 ml), and the mixture was stirred with heating at 80° C. for 5 hr. After completion of the reaction, the mixture was cooled to room temperature and diethyl ether (20 ml) was added. The precipitated solid was collected by filtration to give 4-cyano-4-(4-fluorophenyl)piperidine hydrobromide (0.84 g, yield 61%).
$^1$H-NMR(300 MHz, DMSO-$d_6$)δ(ppm): 2.22-2.28(2H, m), 2.42-2.49(2H, m), 3.12-3.17(2H, m), 3.50-3.55(2H, m), 7.32-7.39(2H, m), 7.55-7.61(2H, m), 8.67(2H, s).

Starting Material Synthetic Example 30

By a similar operation as in Starting Material Synthetic Example 29, 4-cyano-4-(2-methoxyphenyl)piperidine hydrobromide (2.1 g, yield 30%) was obtained from 2-methoxybenzyl cyanide (Tokyo Chemical Industry CO., LTD., 3.18 g) and the compound (5.1 g) of Starting Material Synthetic Example 26.
$^1$H-NMR(300 MHz, DMSO-$d_6$)δ(ppm): 2.16-2.26(2H, m), 2.49-2.57(2H, m), 3.17(2H, d, J=13.2 Hz), 3.52(2H, d, J=13.2 Hz), 3.89(3H, s), 7.06(1H, t, J=7.4 Hz), 7.20(1H, d, J=8.0 Hz), 7.39(1H, d, J=8.0 Hz), 7.47(1H, t, J=7.4 Hz), 8.74(2H, s).

Starting Material Synthetic Example 31

The compound (1.75 g) of Starting Material Synthetic Example 28 and 4-fluorobenzotrifluoride (Aldrich Co., 0.41 g) were dissolved in toluene (1 ml). A potassium hexamethyldisylazide-toluene solution (0.5 M, 7.5 ml) was added, and the mixture was stirred with heating at 60° C. for 1 hr. The reaction mixture was poured into ice-cooled 1N aqueous hydrochloric acid, and the mixture was extracted with toluene. The organic layer was washed with water and dried. The solvent was evaporated under reduced pressure. The obtained residue was dissolved in ethyl acetate (1 ml), and a 4N hydrochloric acid-ethyl acetate solution (3 ml) was added at 0° C. The mixture was gradually warmed to room temperature with stirring. After completion of the reaction, the solvent was evaporated under reduced pressure. Diethyl ether was added and the precipitated solid was collected by filtration to give 4-cyano-4-[4-(trifluoromethyl)phenyl]piperidine hydrochloride (0.33 g, yield 45%).
$^1$H-NMR(300 MHz, DMSO-$d_6$)δ(ppm): 2.41-2.51(4H, m), 3.06-3.16(2H, m), 3.50-3.57(2H, m), 7.77-7.79(2H, m), 7.89-7.91(2H, m), 9.29(2H, s).

Starting Material Synthetic Example 32

By a similar operation as in Starting Material Synthetic Example 31, 4-cyano-4-[3-(trifluoromethyl)phenyl]piperidine hydrochloride (0.33 g, yield 45%) was obtained from compound (500 mg) of Starting Material Synthetic Example 28 and 3-fluorobenzotrifluoride (Aldrich Co., 590 mg).
$^1$H-NMR(300 MHz, DMSO-$d_6$)δ(ppm): 2.28-2.34(2H, m), 2.50-2.55(2H, m), 3.11-3.20(2H, m), 3.53-3.57(2H, m), 7.75-7.89(4H, m), 8.64(2H, s).

Starting Material Synthetic Example 33

2-Fluorobenzyl cyanide (Tokyo Chemical Industry CO., LTD., 0.99 g) was dissolved in tetrahydrofuran (18 ml) and the mixture was cooled to 0° C. Sodium amide (550 mg) and the compound (1.91 g) of Starting Material Synthetic Example 24 were added, and the mixture was stirred with heating at 60° C. for 3 hr. After completion of the reaction, a saturated aqueous ammonium chloride solution was added, and the mixture was extracted with diethyl ether. The organic layer was dried and the solvent was evaporated under reduced pressure. The resulting solid was washed in a suspension state with diethyl ether. A hydrobromide saturated acetic acid solution (5 ml) was added to the intermediate, and the mixture was stirred at 80° C. for 5 hr. The reaction mixture was cooled to room temperature. The solvent was evaporated under reduced pressure, and diethyl ether was added to the obtained residue. The precipitated solid was collected by filtration to give 4-cyano-4-(2-fluorophenyl)piperidine hydrobromide (0.27 g, yield 15%).

$^1$H-NMR(300 MHz, DMSO-d$_6$)δ(ppm): 2.22-2.32(2H, m), 2.50-2.54(2H, m), 3.11-3.23(2H, m), 3.52-3.57(2H, m), 7.32-7.41(2H, m), 7.50-7.55(2H, m), 8.65(1H, s), 8.76(1H, s).

Starting Material Synthetic Example 34

4-Chloro-3-[(trifluoromethyl)phenyl]benzyl cyanide (MATRIX Co., 830 mg) was dissolved in tetrahydrofuran (5 ml), and the mixture was cooled to 0° C. Sodium amide (290 mg) and the compound (830 mg) of Starting Material Synthetic Example 27 were added, and the mixture was stirred with heating at 60° C. for 3 hr. After completion of the reaction, a saturated aqueous ammonium chloride solution was added, and the mixture was extracted with diethyl ether. The organic layer was dried and the solvent was evaporated under reduced pressure. The obtained residue was purified by silica gel column chromatography (elution solvent: hexane-ethyl acetate (10:1-2:1)). A 4N hydrochloric acid-ethyl acetate solution (5 ml) was added to the intermediate, and the mixture was stirred at room temperature for 2 hr. Diethyl ether was added and the mixture was stirred at 0° C. The precipitated solid was collected by filtration. An aqueous sodium hydrogen carbonate solution was added to the solid, and the mixture was extracted with methylene chloride. The organic layer was dried and the solvent was evaporated under reduced pressure. The obtained residue was purified by silica gel column chromatography (elution solvent: methanol-chloroform (20:1)) to give 4-[4-chloro-3-(trifluoromethyl)phenyl]-4-cyanopiperidine (74 mg, yield 8%).

$^1$H-NMR(300 MHz, DMSO-d$_6$)δ(ppm): 1.89-1.95(2H, m), 2.05-2.10(2H, m), 2.75-2.84(2H, m), 3.04-3.08(2H, m), 7.81-7.89(3H, m).

Starting Material Synthetic Example 35

By a similar operation as in Starting Material Synthetic Example 33, 4-cyano-4-[3-fluoro-5-(trifluoromethyl)phenyl]piperidine hydrobromide (0.4 g, yield 20%) was obtained from 3-fluoro-5-(trifluoromethyl)benzyl cyanide (APOLLO Co., 1.7 g) and the compound (2.9 g) of Starting Material Synthetic Example 25.

$^1$H-NMR(300 MHz, DMSO-d$_6$)δ(ppm): 2.29-2.37(2H, m), 2.58(2H, d, J=13.7 Hz), 3.10-3.19(2H, m), 3.56(2H, d, J=13.7 Hz), 7.75-7.85(3H, m), 8.62(1H, s), 8.85(1H, s).

Starting Material Synthetic Example 36

By a similar operation as in Starting Material Synthetic Example 33, 4-(5-bromo-2-thienyl)-4-cyanopiperidine hydrobromide (0.25 g, yield 41%) was obtained from thiophene-2-acetonitrile (Aldrich Co., 700 mg) and the compound (1.9 g) of Starting Material Synthetic Example 25.

$^1$H-NMR(300 MHz, DMSO-d$_6$)δ(ppm): 1.77-1.86(2H, m), 2.13-2.17(2H, m), 2.69-2.77(2H, m), 2.97-3.02(2H, m), 7.03-7.07(1H, m), 7.16-7.20(2H, m).

Starting Material Synthetic Example 37

By a similar operation as in Starting Material Synthetic Example 33, 4-cyano-4-(3,5-difluorophenyl)piperidine hydrobromide (1.5 g, yield 98%) was obtained from 3,5-difluorobenzyl cyanide (Aldrich Co., 1.0 g) and the compound (2.3 g) of Starting Material Synthetic Example 25.

$^1$H-NMR(300 MHz, DMSO-d$_6$)δ(ppm): 2.20-2.31(2H, m), 2.50-2.54(2H, m), 3.00-3.20(2H, m), 3.51-3.55(2H, m), 7.29-7.42(3H, m), 8.61(1H, s), 8.80(1H, s).

Starting Material Synthetic Example 38

The compound (2.0 g) of Starting Material Synthetic Example 28 was dissolved in toluene (2 ml), a sodiumhexamethyldisylazide-toluene solution (0.6 M, 18.7 ml) was added thereto, and the mixture was stirred at room temperature for 10 min. The reaction mixture was added to a mixture of 4-bromo-2-chlorofluorobenzene (Aldrich Co., 1.8 g), palladium acetate (116 mg), 2,2-bis(diphenylphosphino)-1,1-binaphthyl (323 mg) and toluene (3 ml), and the mixture was stirred with heating at 100° C. for 8 hr. After completion of the reaction, the mixture was cooled to room temperature. Water was added, and the mixture was extracted with diethyl ether. The organic layer was dried and the solvent was evaporated under reduced pressure. The obtained residue was dissolved in ethyl acetate (1 ml), and a 4N hydrochloric acid-ethyl acetate solution (3 ml) was added at 0° C. The mixture was gradually warmed to room temperature when stirring. The solvent was evaporated under reduced pressure and diethyl ether was added. The precipitated solid was collected by filtration to give 4-(4-bromo-2-chlorophenyl)-4-cyanopiperidine hydrochloride (0.32 g, yield 11%).

$^1$H-NMR(300 MHz, DMSO-d$_6$)δ(ppm): 2.26-2.34(2H, m), 2.69(2H, d, J=13.3 Hz), 3.08-3.20(2H, m), 3.53(2H, d, J=13.3 Hz), 7.49(1H, d, J=8.6 Hz), 7.72(1H, d, J=8.6 Hz), 7.92(1H, s), 9.24(1H, s), 9.26(1H, s).

Starting Material Synthetic Example 39

4-{[(Trifluoromethyl)sulfonyl]oxy}-3,6-dihydropyridine-1(2H)carboxylic acid tert-butyl ester (synthesized according to the method described in Synthesis, 1991, 993-995, 1.0 g), 3-chloro-4-fluorophenylboric acid (Aldrich Co., 790 mg), lithium chloride (380 mg), tetrakistriphenylphosphine palladium (170 mg) and a 2N sodium carbonate aqueous solution (5 ml) were added to dimethoxyethane (12 ml), and the mixture was heated under reflux for 6 hr. After completion of the reaction, the reaction mixture was washed with a sodium carbonate aqueous solution and aqueous ammonia, and the aqueous layer was extracted with ethyl acetate. The organic layers were combined and dried, and the solvent was evaporated under reduced pressure. The obtained residue was purified by silica gel column chromatography (elution solvent: hexane-ethyl acetate (20:1-10:1)). The intermediate was dissolved in methylene chloride, and trifluoroacetic acid was added. The mixture was stirred at room temperature for 8 hr. After completion of the reaction, a saturated aqueous sodium hydrogen carbonate solution was added and the mixture was extracted with chloroform. The organic layer was dried and the solvent was evaporated under reduced pressure. The precipitated solid was collected by filtration to give 4-(3-chloro-4-fluorophenyl)-1,2,3,6-tetrahydropyridine (357 mg, yield 56%).

$^1$H-NMR(300 MHz, DMSO-d$_6$)δ(ppm): 2.40-2.42(2H, m), 3.00-3.01(2H, m), 3.46-3.47(2H, m), 6.26(1H, s), 7.05-7.62(3H, m).

Starting Material Synthetic Example 40

By a similar operation as in Starting Material Synthetic Example 39, 4-(2,3-difluorophenyl)-1,2,3,6-tetrahydropyridine 15 (278 mg, yield 62%) was obtained from 2,3-difluorophenylboric acid (Aldrich Co., 363 mg).

$^1$H-NMR(300 MHz, DMSO-d$_6$)δ(ppm): 2.60-2.61(2H, m), 3.26-3.29(2H, m), 3.73-3.74(2H, m), 6.09(1H, s), 7.18-7.42(3H, m).

Starting Material Synthetic Example 41

By a similar operation as in Starting Material Synthetic Example 39, 4-(2,4-difluorophenyl)-1,2,3,6-tetrahydropyridine (1.0 g, yield 65%) was obtained from 2,4-difluorophenylboric acid (Aldrich Co., 1.42 g).

$^1$H-NMR(300 MHz, DMSO-d$_6$)δ(ppm): 2.50-2.51(2H, m), 3.31-3.32(2H, m), 3.75-3.76(2H, m), 6.00(1H, s), 7.09-7.46(3H, m).

Starting Material Synthetic Example 42

A 5-chlorothienyl magnesium bromide-tetrahydrofuran solution (Aldrich Co., 0.5 M, 22 ml) was cooled to 0° C., and 1-(tert-butoxycarbonyl)-4-piperidone (Aldrich Co. (hereafter the same), 2.0 g) was dissolved in tetrahydrofuran (10 ml) and added thereto. The mixture was heated under reflux for 8 hr. After completion of the reaction, the mixture was cooled to 0° C. A saturated aqueous ammonium chloride solution was added, and a solid was filtered off. The filtrate was extracted with diethyl ether. The organic layer was dried and the solvent was evaporated under reduced pressure. The obtained residue was purified by silica gel column chromatography (elution solvent:hexane-ethyl acetate (5:1)). The intermediate was dissolved in ethyl acetate, and a 4N hydrochloric acid-ethyl acetate solution (3 ml) was added. The mixture was stirred at room temperature for 3 hr. After completion of the reaction, the solvent was evaporated under reduced pressure. The precipitated solid was collected by filtration to give 4-(5-chloro-2-thienyl)-1,2,3,6-tetrahydropyridine hydrochloride (637 mg, yield 23%).

$^1$H-NMR(300 MHz, DMSO-d$_6$)δ(ppm): 2.26-2.27(2H, m), 2.84-2.85(2H, m), 3.29-3.30(2H, m), 6.06(1H, s), 6.89 (2H, d, J=2.7 Hz), 7.01(2H, d, J=2.7 Hz).

Starting Material Synthetic Example 43

3-Bromo-N,N-dimethylaniline (Aldrich Co., 1.24 g) was dissolved in tetrahydrofuran (18 ml) and the mixture was cooled to −78° C. An n-butyllithium hexane solution (2.6 M, 3.0 ml) was added to the solution and the mixture was stirred for min. 1-(tert-Butoxycarbonyl)-4-piperidone (1.0 g) was added thereto, and the mixture was gradually warmed to room temperature. After completion of the reaction, a saturated aqueous ammonium chloride solution was added, and the mixture was extracted with diethyl ether. The organic layer was dried and the solvent was evaporated under reduced pressure. The obtained residue was purified by silica gel column chromatography (elution solvent: hexane:ethyl acetate (5:1-2:1)). 10% Aqueous sulfuric acid (5 ml) and 1,4-dioxane (5 ml) were added to the intermediate, and the mixture was stirred with heating at 70° C. for 3 hr. After completion of the reaction, the mixture was cooled to 0° C. A 1N aqueous sodium hydroxide solution was added, and the mixture was extracted with ethyl acetate. The organic layer was dried and the solvent was evaporated under reduced pressure to give 4-[3-(dimethylamino)phenyl]-1,2,3,6-tetrahydropyridine (119 mg, yield 10%).

$^1$H-NMR(300 MHz, DMSO-d$_6$)δ(ppm): 2.35-2.51(2H, m), 2.91(6H, s), 2.95-3.00(2H, m), 3.37-3.40(2H, m), 6.07 (1H, s), 6.60-6.73(3H, m), 7.07-7.13(1H, m).

Starting Material Synthetic Example 44

5-Bromo-2-chlorobenzotrifluoride (Aldrich Co., 2.0 g) was dissolved in diethyl ether (50 ml), and the mixture was cooled to −78° C. An n-butyllithium hexane solution (2.6 M, 3.2 ml) was added to the solution and the mixture was stirred for 10 min. 1-(tert-Butoxycarbonyl)-3-piperidone (Aldrich Co., 1.6 g) was added, and the mixture was gradually warmed to room temperature. After completion of the reaction, a saturated aqueous ammonium chloride solution was added, and the mixture was extracted with diethyl ether. The organic layer was dried and the solvent was evaporated under reduced pressure. The obtained residue was purified by silica gel column chromatography (elution solvent: hexane-ethyl acetate (5:1-2:1)). The intermediate was dissolved in ethyl acetate, and a 4N hydrochloric acid-ethyl acetate solution (3 ml) was added. The mixture was stirred at room temperature for 3 hr. After completion of the reaction, the solvent was evaporated under reduced pressure. The precipitated solid was collected by filtration to give 3-[4-chloro-3-(trifluoromethyl)phenyl]piperidin-3-ol hydrochloride (655 mg, yield 27%).

$^1$H-NMR(300 MHz, DMSO-d$_6$)δ(ppm): 1.68-1.83(2H, m), 2.01-2.13(1H, m), 2.51-2.61(1H, m), 2.92-2.96(1H, m), 3.10-3.26(2H, m), 3.70-3.78(1H, m), 6.45(1H, s), 7.70-7.78 (2H, m), 8.11(1H, s), 8.44(1H, s), 9.46(1H, s).

Starting Material Synthetic Example 45

5-Bromo-3-fluorobenzo trifluoride (APOLLO Co., 9.0 g) was dissolved in diethyl ether (110 ml), and the mixture was cooled to −78° C. An n-butyllithium hexane solution (2.71 M, 17.5 ml) was added to this solution, and the mixture was stirred at −78° C. for 1 hr. Then, 1-(tert-butoxycarbonyl)-4-piperidone (6.71 g) was added. The reaction temperature was then warmed to 0° C., and the mixture was further stirred for 1 hr. After completion of the reaction, water was added, and the mixture was extracted three times with ethyl acetate. The organic layer was dried and the solvent was evaporated under reduced pressure. The obtained residue was purified by silica gel column chromatography (elution solvent: hexane-ethyl acetate (5:1-2:1)). Then, the residue was dissolved in 1,4-dioxane (150 ml), and 10% aqueous sulfuric acid (10 ml) was added thereto. The mixture was stirred with heating at 70° C. for 2 hr. After completion of the reaction, the reaction system was basified (pH=9) with an 1N aqueous sodium hydroxide solution, and extracted three times with chloroform. The organic layer was dried and the solvent was evaporated under reduced pressure to give 4-[3-fluoro-5-(trifluoromethyl)phenyl]piperidin-4-ol (9.89 g, yield 56%).

$^1$H-NMR(300 MHz, DMSO-d$_6$)δ(ppm): 1.76-1.81(2H, m), 2.21-2.31(2H, m), 3.17-3.32(4H, m), 5.85(1H, s), 7.55-7.60(3H, m).

Starting Material Synthetic Example 46

By a similar operation as in Starting Material Synthetic Example 45, 4-[2-(trifluoromethyl)phenyl]piperidin-4-ol (952 mg, yield 85%) was obtained from 2-(trifluoromethyl)bromobenzene (Tokyo Chemical Industry CO., LTD., 1.0 g).

$^1$H-NMR(400 MHz, DMSO-$d_6$)δ(ppm): 1.88-1.93(2H, m), 2.27-2.29(2H, m), 3.18-3.19(4H, m), 5.47(1H, s), 7.46-7.79(4H, m).

Starting Material Synthetic Example 47

By a similar operation as in Starting Material Synthetic Example 45, 4-[3-(trifluoromethoxy)phenyl]piperidin-4-ol (381 mg, yield 37%) was obtained from 3-(trifluoromethoxy)bromobenzene (Tokyo Chemical Industry CO., LTD., 700 mg).

$^1$H-NMR(400 MHz, DMSO-$d_6$)δ(ppm): 1.74-1.75(2H, m), 2.22-2.25(2H, m), 3.16-3.19(4H, m), 5.04(1H, s), 7.26-7.54(4H, m).

Starting Material Synthetic Example 48

By a similar operation as in Starting Material Synthetic Example 45, 4-[4-fluoro-3-(trifluoromethyl)phenyl]piperidin-4-ol (832 mg, yield 69%) was obtained from 4-fluoro-3-(trifluoromethyl)bromobenzene (APOLLO CO., 1.0 g).

$^1$H-NMR(400 MHz, DMSO-$d_6$)δ(ppm): 1.74-1.78(2H, m), 2.25-2.28(2H, m), 3.00-3.12(4H, m), 5.04(1H, s), 7.51-7.83(3H, m).

Starting Material Synthetic Example 49

By a similar operation as in Starting Material Synthetic Example 45, 4-[4-methyl-3-(trifluoromethyl)phenyl]piperidin-4-ol (1.76 g, yield 68%) was obtained from 4-methyl-3-(trifluoromethyl)bromobenzene (APOLLO CO., 2.9 g).

$^1$H-NMR(400 MHz, DMSO-$d_6$)δ(ppm): 1.76-1.78(2H, m), 2.22-2.26(2H, m), 2.43(3H, s), 2.50-2.52(2H, m), 2.99-3.00(2H, m), 5.05(1H, s), 7.44-7.75(3H, m).

Starting Material Synthetic Example 50

1-(tert-Butoxycarbonyl)-4-piperidone (2.19 g) was dissolved in tetrahydrofuran (30 ml) and the mixture was cooled to 0° C. 3-Fluorophenylmagnesiumbromide (Tokyo Chemical Industry CO., LTD., 1M, 13.2 ml) was added and the mixture was stirred for 6 hr. After completion of the reaction, a saturated aqueous ammonium chloride solution was added, and the mixture was extracted three times with ethyl acetate. The organic layer was dried and the solvent was evaporated under reduced pressure. The obtained residue was purified by silica gel column chromatography (elution solvent: hexane-ethyl acetate (5:1-2:1)). Then, 4N hydrochloric acid-ethyl acetate (10 ml) was added and the mixture was stirred for 3 hr. Diethyl ether was added and the precipitated solid was collected by filtration to give 4-(3-fluorophenyl)piperidin-4-ol hydrochloride (902 mg, yield 35%).

$^1$H-NMR(300 MHz, DMSO-$d_6$)δ(ppm): 1.72-1.77(2H, m), 2.19-2.29(2H, m), 3.18(4H, m), 5.62(1H, s), 7.07-7.46 (4H, m), 8.96(2H, m).

Starting Material Synthetic Example 51

By a similar operation as in Starting Material Synthetic Example 45, 4-(3,5-difluorophenyl)piperidin-4-ol (6.6 g, yield 60%) was obtained from 3,5-difluorobromobenzene (Tokyo Chemical Industry CO., LTD., 10.0 g).

$^1$H-NMR(400 MHz, DMSO-$d_6$)δ(ppm): 1.73-1.76(2H, m), 2.22-2.26(2H, m), 2.50-2.57(2H, m), 3.10-3.12(2H, s), 5.23(1H, s), 7.00-7.16(3H, m).

Starting Material Synthetic Example 52

By a similar operation as in Starting Material Synthetic Example 45, 4-(3-pyridyl)piperidin-4-ol (600 mg, yield 34%) was obtained from 3-bromopyridine(Tokyo Chemical Industry CO., LTD., 1.9 g).

$^1$H-NMR(400 MHz, DMSO-$d_6$)δ(ppm): 1.57-1.62(2H, m), 1.81-1.87(2H, m), 2.73-2.78(2H, m), 2.89-2.98(2H, m), 5.04(1H, s), 7.32-8.71(4H, m).

Starting Material Synthetic Example 53

By a similar operation as in Starting Material Synthetic Example 45, 4-(5-chloro-2-thienyl)piperidin-4-ol (3.08 g, yield 81%) was obtained from 2-bromo-5-chlorothiophene (Tokyo Chemical Industry CO., LTD., 2.77 g).

$^1$H-NMR(400 MHz, DMSO-$d_6$)δ(ppm): 1.64-1.78(4H, m), 2.68-2.72(2H, m), 2.80-2.86(2H, m), 5.48(1H, s), 6.76 (2H, d, J=3.6 Hz), 6.92(2H, d, J=3.6 Hz).

Starting Material Synthetic Example 54

By a similar operation as in Starting Material Synthetic Example 45, 4-(3-chloro-4-fluorophenyl)piperidin-4-ol (3.13 g, yield 53%) was obtained from 3-chloro-4-fluorobromobenzene (Tokyo Chemical Industry CO., LTD., 12.6 g).

$^1$H-NMR(400 MHz, DMSO-$d_6$)δ(ppm): 1.45-1.49(2H, m), 1.72-1.82(2H, m), 2.72-2.92(4H, m), 5.00(1H, s), 7.29-7.59(3H, m).

Starting Material Synthetic Example 55

By a similar operation as in Starting Material Synthetic Example 45, 4-(3,4,5-trifluorophenyl)piperidin-4-ol (393 mg, yield 17%) was obtained from 3,4,5-trifluorobromobenzene(Tokyo Chemical Industry CO., LTD., 2.53 g).

$^1$H-NMR(400 MHz, DMSO-$d_6$)δ(ppm): 1.42-1.46(2H, m), 1.77-1.82(2H, m), 2.64-2.71(2H, m), 2.81-2.85(2H, m), 5.04(1H, s), 7.25-7.54(2H, m).

Starting Material Synthetic Example 56

Starting Material Synthetic Example 58

By a similar operation as in Starting Material Synthetic Example 45, 4-(4-chloro-3-fluorophenyl)piperidin-4-ol (1.13 g, yield 49%) was obtained from 4-chloro-3-fluorobromobenzene(Tokyo Chemical Industry CO., LTD., 2.5 g).

$^1$H-NMR(400 MHz, DMSO-$d_6$)δ(ppm): 1.40-1.46(2H, m), 1.75-1.81(2H, m), 2.67-2.72(2H, m), 2.82-2.86(2H, m), 5.01(1H, s), 7.32-7.61(3H, m).

As a byproduct, 4-(5-bromo-3-chloro-2-fluorophenyl)piperidin-4-ol can also be obtained.

Starting Material Synthetic Example 57

By a similar operation as in Starting Material Synthetic Example 45, 4-[4-fluoro-2-(trifluoromethyl)phenyl]piperidin-4-ol (120 mg, yield 32%) was obtained from 4-fluoro-2-(trifluoromethyl)bromobenzene(APOLLO CO., 300 mg).

¹H-NMR(400 MHz, DMSO-d₆)δ(ppm): 1.92-1.94(2H, m), 2.46-2.48(2H, m), 3.20-3.22(4H, m), 5.54(1H, s), 7.64-7.65(3H, m).

Starting Material Synthetic Example 59

3-Chloro-2-fluoroiodobenzene (Tokyo Chemical Industry CO., LTD., 3.1 g) was dissolved in tetrahydrofuran (20 ml) and the mixture was cooled to 0° C. An isopropylmagnesium chloride-tetrahydrofuran solution (2M, 18 ml) was added, and the mixture was stirred for 3 hr. Then, 1-(tert-butoxycarbonyl)-4-piperidone (2 g) was added and the mixture was stirred for 3 hr. After completion of the reaction, a saturated aqueous ammonium chloride solution was added, and the mixture was extracted three times with ethyl acetate. The organic layer was dried and the solvent was evaporated under reduced pressure. The obtained residue was purified by silica gel column chromatography (elution solvent: hexane-ethyl acetate (5:1-2:1)). Then, the residue was dissolved in 1,4-dioxane (30 ml) and 10% aqueous sulfuric acid (5 ml) was added thereto. The mixture was stirred with heating at 70° C. for 2 hr. After completion of the reaction, the reaction system was basified (pH=9) with a 1N aqueous sodium hydroxide solution and extracted three times with chloroform. The organic layer was dried and the solvent was evaporated under reduced pressure to give 4-(3-chloro-2-fluorophenyl)piperidin-4-ol (1.0 g, yield 44%).
¹H-NMR(400 MHz, DMSO-d₆)δ(ppm): 1.48-1.51(2H, m), 2.01-2.05(2H, m), 2.69-2.70(2H, m), 2.89-2.92(2H, m), 5.13(1H, s), 7.17-7.60(3H, m).

Starting Material Synthetic Example 60

By a similar operation as in Starting Material Synthetic Example 45, 4-(3,4-dichlorophenyl)piperidin-4-ol (1.2 g, yield 49%) was obtained from 3,4-dichlorobromobenzene (Tokyo Chemical Industry CO., LTD., 2.5 g).
¹H-NMR(400 MHz, DMSO-d₆)δ(ppm): 1.49-1.52(2H, m), 1.74-1.79(2H, m), 2.50-2.51(2H, m), 2.89-2.92(2H, m), 5.03(1H, s), 7.40-7.70(3H, m).

Starting Material Synthetic Example 61

By a similar operation as in Starting Material Synthetic Example 45, 4-(3-chloro-5-fluorophenyl)piperidin-4-ol (1.27 g, yield 55%) was obtained from 3-chloro-5-fluorobromobenzene (APOLLO CO., 2.3 g).
¹H-NMR(400 MHz, DMSO-d₆)δ(ppm): 1.42-1.45(2H, m), 1.73-1.82(2H, m), 2.62-2.73(2H, m), 2.80-2.84(2H, m), 5.04(1H, s), 7.25-7.71(3H, m).

Starting Material Synthetic Example 62

By a similar operation as in Starting Material Synthetic Example 45, 4-(4-chloro-3-methylphenyl)piperidin-4-ol (1.17 g, yield 52%) was obtained from 5-bromo-2-chlorotoluene (Tokyo Chemical Industry CO., LTD., 2.3 g).
¹H-NMR(400 MHz, DMSO-d₆)δ(ppm): 1.71-1.73(2H, m), 2.20-2.28(2H, m), 3.12-3.17(4H, m), 5.54(1H, s), 7.27-7.47(3H, m).

Starting Material Synthetic Example 63

By a similar operation as in Starting Material Synthetic Example 45, 4-(3-chlorophenyl)piperidin-4-ol (890 mg, yield 42%) was obtained from 3-chlorobromobenzene (Tokyo Chemical Industry CO., LTD., 2.1 g).
¹H-NMR(400 MHz, DMSO-d₆)δ(ppm): 1.50-1.52(2H, m), 1.75-1.80(2H, m), 2.50-2.51(2H, m), 2.89-2.92(2H, m), 5.03(1H, s), 7.35-7.70(4H, m).

Starting Material Synthetic Example 64

The title compound [4-(2-naphthyl)piperidin-4-ol] can be synthesized according to the method described in WO97/48698.

Starting Material Synthetic Example 65

By a similar operation as in Starting Material Synthetic Example 59, 4-(2-chloropyridin-4-yl)piperidin-4-ol (717 mg, yield 20%) was obtained from 2-chloro-4-iodopyridine (Frontier Co., 4.25 g).
¹H-NMR(400 MHz, DMSO-d₆)δ(ppm): 1.47-1.50(2H, m), 1.76-1.84(2H, m), 2.76-2.90(2H, m), 2.91-2.95(2H, m), 5.24(1H, s), 7.43-8.35(3H, m).

Starting Material Synthetic Example 66

4-Bromo-1,2-(methylenedioxy)benzene (Tokyo Chemical Industry CO., LTD., 2.0 g) was dissolved in tetrahydrofuran (15 ml) and the mixture was cooled to −78° C. An n-butyllithium hexane solution (2.44 M, 5.7 ml) was added to the solution. The mixture was stirred at −78° C. for 1 hr, and 1-(ethoxycarbonyl)-4-piperidone (Aldrich Co., 1.7 g) was added. Then, the reaction temperature was raised to 0° C., and the mixture was further stirred for 1 hr. After completion of the reaction, water was added and the mixture was extracted three times with ethyl acetate. The organic layer was dried and the solvent was evaporated under reduced pressure. The obtained residue was purified by silica gel column chromatography (elution solvent: hexane-ethyl acetate (5:1-2:1)). Then, the residue was dissolved in ethylene glycol (20 ml), a 50% aqueous potassium hydroxide solution was added, and the mixture was stirred with heating at 120° C. for 6 hr. After completion of the reaction, the mixture was extracted three times with chloroform. The organic layer was dried and the solvent was evaporated under reduced pressure to give 4-(1,3-benzodioxol-5-yl)piperidin-4-ol (1.0 g, yield 43%).
¹H-NMR(400 MHz, DMSO-d₆)δ(ppm): 1.29-1.32(2H, m), 1.56-1.61(2H, m), 2.53-2.55(2H, m), 2.90-2.93(2H, m), 4.53(1H, brs), 5.79(2H, s), 6.64-6.84(3H, m).

Starting Material Synthetic Example 67

By a similar operation as in Starting Material Synthetic Example 59, 4-(3-methylphenyl)piperidin-4-ol (13.5 g, yield 68%) was obtained from 3-iodotoluene (Tokyo Chemical Industry CO., LTD., 20 g).
¹H-NMR(400 MHz, DMSO-d₆)δ(ppm): 1.48(2H, d, J=11.6 Hz), 1.72-1.79(2H, m), 2.29(3H, s), 2.89(2H, d, J=11.6 Hz), 2.91-2.98(2H, m), 6.98-7.28(4H, m).

Starting Material Synthetic Example 68

By a similar operation as in Starting Material Synthetic Example 59, 4-(3-cyanophenyl)piperidin-4-ol (484 mg, yield 30%) was obtained from 3-cyanoiodobenzene (Wako Pure Chemical Industries, Ltd., 2.0 g).
¹H-NMR(400 MHz, DMSO-d₆)δ(ppm): 1.50(2H, d, J=16.0 Hz), 1.80-1.86(2H, m), 2.76(2H, d, J=16.0 Hz), 2.90-2.96(2H, m), 5.06(1H, s), 7.52-7.85(4H, m).

Starting Material Synthetic Example 69

By a similar operation as in Starting Material Synthetic Example 45, 4-[3-(methylthio)phenyl]piperidin-4-ol (1.6 g, yield 81%) was obtained from 3-bromothioanisole (Aldrich Co., 1.5 g).
$^1$H-NMR(400 MHz, DMSO-$d_6$)δ(ppm): 1.43-1.45(2H, m), 1.72-1.75(2H, m), 2.40(3H, s), 2.85-2.88(2H, m), 2.88-2.91(2H, m), 5.04(1H, s), 7.00-7.28(4H, m).

Starting Material Synthetic Example 70

By a similar operation as in Starting Material Synthetic Example 45, 4-(3-ethylphenyl)piperidin-4-ol (1.46 g, yield 79%) was obtained from 3-ethylbromobenzene (Avocado Co., 2.0 g).
$^1$H-NMR(400 MHz, DMSO-$d_6$)δ(ppm): 1.18-1.99(3H, m), 1.48(2H, d, J=11.2 Hz), 1.77-1.80(2H, m), 2.49-2.62(2H, m), 2.70(2H, d, J=11.2 Hz), 2.91-2.94(2H, m), 4.67(1H, s), 7.01-7.31(4H, m).

Starting Material Synthetic Example 71

By a similar operation as in Starting Material Synthetic Example 45, 4-(1-acetyl-2,3-dihydro-1H-indol-5-yl)piperidin-4-ol (576 mg, yield 32%) was obtained from 1-acetyl-5-bromoindoline (Lancaster Co., 2.0 g).
$^1$H-NMR(400 MHz, DMSO-$d_6$)δ(ppm): 1.50-1.64(4H, m), 1.72-1.85(4H, m), 2.44(3H, s), 2.50-2.51(2H, m), 2.89-2.92(2H, m), 4.84(1H, s), 7.00-7.20(3H, m).

Starting Material Synthetic Example 72

By a similar operation as in Starting Material Synthetic Example 59, 4-(2,5-dichlorophenyl)piperidin-4-ol (7.5 g, yield 39%) was obtained from 1,4-dichloro-2-iodobenzene (Tokyo Chemical Industry CO., LTD., 25 g).
$^1$H-NMR(400 MHz, DMSO-$d_6$)δ(ppm): 1.36(2H, d, J=12.0 Hz), 2.41-2.48(2H, m), 2.74(2H, d, J=12.0 Hz), 2.91-2.95(2H, m), 7.30-8.31(3H, m).

Starting Material Synthetic Example 73

By a similar operation as in Starting Material Synthetic Example 45, 4-[3,5-bis(trifluoromethyl)phenyl]piperidin-4-ol (663 mg, yield 35%) was obtained from 3,5-bis(trifluoromethyl)bromobenzene (Tokyo Chemical Industry CO., LTD., 1.46 g).
$^1$H-NMR(300 MHz, DMSO-$d_6$)δ(ppm): 1.69(2H, d, J=12.6 Hz), 2.06-2.17(2H, m), 3.05(2H, d, J=12.6 Hz), 3.33-3.59(2H, m), 5.69(1H, s), 8.03-8.08(3H, m).

Starting Material Synthetic Example 74

By a similar operation as in Starting Material Synthetic Example 45, 4-[2-fluoro-5-(trifluoromethyl)phenyl]piperidin-4-ol (409 mg, yield 32%) was obtained from 3-bromo-4-fluorobenzotrifluoride (APOLLO Co., 1.44 g).
$^1$H-NMR(300 MHz, DMSO-$d_6$)δ(ppm): 1.43-1.48(2H, m), 2.02-2.11(2H, m), 2.70-2.75(2H, m), 2.92(2H, m), 5.30 (1H, s), 7.34-7.98(3H, m).

Starting Material Synthetic Example 75

By a similar operation as in Starting Material Synthetic Example 45, 4-[2-chloro-5-(trifluoromethyl)phenyl]piperidin-4-ol (903 mg, yield 65%) was obtained from 3-bromo-4-chlorobenzotrifluoride (APOLLO Co., 1.56 g).
$^1$H-NMR(300 MHz, DMSO-$d_6$)δ(ppm): 1.37-1.41(2H, m), 2.51-2.53(2H, m), 2.71-2.81(2H, m), 2.90-3.00(2H, m), 5.33(1H, s), 7.64-8.16(3H, m).

Starting Material Synthetic Example 76

An aqueous hydrobromide acid solution (2 M, 2 ml) was added to 5-bromo-2-chlorobenzyl alcohol (Aldrich Co., 1 g), and the mixture was stirred with heating at 70° C. for 1 hr. After completion of the reaction, the mixture was extracted three times with diethyl ether. The organic layer was dried and the solvent was evaporated under reduced pressure to give 5-bromo-2-chlorobenzylbromide (1.3 g).
$^1$H-NMR(400 MHz, DMSO-$d_6$)δ(ppm): 4.71(2H, s), 7.45-7.47(1H, m), 7.56-7.59 (1H, m), 7.89 (1H, m)
5-Bromo-2-chlorobenzylbromide (1.3 g) was dissolved in acetonitrile (30 ml). Diethylamine (334 mg) and potassium carbonate (2 g) were added thereto, and the mixture was heated under reflux for 1 hr. After completion of the reaction, the reaction mixture was filtrated, and the filtrate was concentrated. The obtained residue was purified by silica gel column chromatography (elution solvent: hexane-ethyl acetate (2:1-1:2)) to give a white solid. By a similar operation as in Starting Material Synthetic Example 45, 4-{4-chloro-3-[(diethylamino)methyl]phenyl}piperidin-4-ol (610 mg, yield 46%) was obtained from this white solid (1.24 g).
$^1$H-NMR(400 MHz, DMSO-$d_6$)δ(ppm): 1.05-1.07(6H, m), 1.48-1.51(2H, m), 1.77-1.81(2H, m), 2.70-2.73(2H, m), 2.89-2.92(2H, m), 3.51(2H, s), 7.11-7.41 (3H, m).

Starting Material Synthetic Example 77

1-(tert-Butoxycarbonyl)-4-phenylpiperidine-4-carboxylic acid (Bionet Co., 1.0 g), 1-ethyl-3-(3-dimethylaminopropyl) carbodiimide (733 mg), 1-hydroxybenzotriazole (370 mg), morpholine (1 g) and triethylamine (0.76 ml) were dissolved in dimethylformamide (6 ml), and the mixture was stirred at room temperature for 10 hr. After completion of the reaction, 1N sodium hydroxide was added thereto. The precipitated solid was collected by filtration to give 4-(morpholin-4-ylcarbonyl)-4-phenyl-1-piperidinecarboxylic acid tert-butyl ester (907 mg, yield ds89%).
$^1$H-NMR(300 MHz, DMSO-$d_6$)δ(ppm): 1.73-1.79(2H, m), 2.16-2.21(2H, m), 3.17-3.38(10H, m), 4.01-4.04(2H, m), 7.24-7.41(5H, m).
4-(Morpholin-4-ylcarbonyl)-4-phenyl-1-piperidinecarboxylic acid tert-butyl ester (907 mg) was dissolved in methylene chloride (6 ml) and trifluoroacetic acid (1 ml) was added thereto. The mixture was stirred at room temperature for 10 hr. After completion of the reaction, a 10% aqueous sodium hydroxide solution was added, and the mixture was extracted three times with methylene chloride. The organic layer was dried and the solvent was evaporated under reduced pressure to give 4-(morpholin-4-ylcarbonyl)-4-phenylpiperidine (600 mg, yield 91%).
$^1$H-NMR(300 MHz, DMSO-$d_6$)δ(ppm): 1.69-1.76(2H, m), 2.09-2.13(2H, m), 2.73-2.84(4H, m), 3.21-3.30(8H, m), 7.23-7.41(5H, m).

Starting Material Synthetic Example 78

1-(tert-Butoxycarbonyl)-4-phenylpiperidine-4-carboxylic acid (Bionet Co., 1.0 g) was dissolved in tetrahydrofuran (10 ml) and triethylamine (0.55 ml), and the mixture was cooled to 0° C. Under ice-cooling, ethyl chloroformate (0.34 ml) was added to the mixture, and the mixture was stirred for 30 min. Sodium borohydride (250 mg) was added and the mixture was stirred for 30 min. The mixture was warmed to room temperature and stirred for 2 hr. After completion of the reaction, 1N sodium hydroxide was added, and the mixture was extracted with ethyl acetate. The organic layer was dried and the solvent was evaporated under reduced pressure to give 4-(hydroxymethyl)-4-phenyl-1-piperidinecarboxylic acid tert-butyl ester (1.0 g, yield 98%).

$^1$H-NMR(300 MHz, DMSO-d$_6$)δ(ppm): 1.37-1.39(9H, m), 1.73-1.77(2H, m), 2.67-2.69(2H, m), 2.69-2.71(2H, m), 3.62-3.66(2H, m), 4.04-4.66(1H, m), 7.19-7.38(5H, m).

4-(Hydroxymethyl)-4-phenyl-1-piperidinecarboxylic acid tert-butyl ester (953 mg) was dissolved in tetrahydrofuran (10 ml), and the mixture was cooled to 0° C. Sodium hydride (157 mg) was added and the mixture was stirred for 20 min. Dimethylsulfuric acid (0.5 ml) was added, and the mixture was stirred for 5 hr. After completion of the reaction, a saturated aqueous ammonium chloride solution was added, and the mixture was extracted three times with ethyl acetate. The organic layer was dried and the solvent was evaporated under reduced pressure. The obtained residue was purified by silica gel column chromatography to give a colorless oil. Methylene chloride (6 ml) and trifluoroacetic acid (0.5 ml) were added to the oil, and the mixture was stirred at room temperature for 7 hr. After completion of the reaction, 1N sodium hydroxide was added, and the mixture was extracted three times with chloroform. The organic layer was dried and the solvent was evaporated under reduced pressure to give 4-(methoxymethyl)-4-phenylpiperidine (237 mg, yield 35%).

$^1$H-NMR(300 MHz, DMSO-d$_6$)δ(ppm): 1.78-1.83(2H, m), 1.97-1.99(2H, m), 2.49-2.59(2H, m), 2.77-2.82(2H, m), 3.11(3H, s), 3.57-3.59(2H, m), 7.16-7.38(5H, m).

Starting Material Synthetic Example 79

4-[4-Chloro-3-(trifluoromethyl)phenyl]-4-hydroxypiperidine (ACROS Co., 2.0 g) was dissolved in methylene chloride (10 ml), and pyridine (0.6 ml) and ethyl chloroformate (0.8 ml) were added thereto. The mixture was stirred at room temperature for 5 hr. After completion of the reaction, the reaction mixture was concentrated. The obtained residue was purified by silica gel column chromatography (elution solvent: hexane-ethyl acetate (1:2)) to give 4-[4-chloro-3-(trifluoromethyl)phenyl]-4-hydroxy-1-piperidinecarboxylic acid ethyl ester (2.03 g, yield 81%).

$^1$H-NMR(400 MHz, DMSO-d$_6$)δ(ppm): 1.18-1.21(3H, m), 1.55-1.59(2H, m), 1.88-1.89(2H, m), 3.01-3.33(2H, m), 3.90-3.98(2H, m), 4.04-4.06(2H, m), 5.46(1H, s), 7.65-7.96 (3H, m).

4-[4-Chloro-3-(trifluoromethyl)phenyl]-4-hydroxy-1-piperidinecarboxylic acid ethyl ester (2.0 g) was dissolved in dimethylformamide and the mixture was cooled to 0° C. Sodium hydride (250 mg) was added thereto, and the mixture was stirred for 30 min. Then, methyl iodide (0.4 ml) was added, and the mixture was further stirred for 30 min and warmed to room temperature. Water was added thereto, and the mixture was extracted three times with methylene chloride. The organic layer dried over magnesium sulfate and the solvent was evaporated under reduced pressure. Ethanol (20 ml) and a 6N aqueous sodium hydroxide solution (15 ml) were added to the obtained residue, and the mixture was heated under reflux for hr. The reaction mixture was allowed to cool to room temperature, neutralized with 12N aqueous hydrochloric acid, and extracted three times with chloroform. The organic layer was dried and the solvent was evaporated under reduced pressure to give 4-[4-chloro-3-(trifluoromethyl)phenyl]-4-methoxypiperidine (1.56 g, yield 93%).

$^1$H-NMR(400 MHz, DMSO-d$_6$)δ(ppm): 2.14-2.18(4H, m), 2.93(3H, s), 3.02-3.23(4H, m), 7.69-7.81(3H, m).

Starting Material Synthetic Example 80

1-(tert-Butoxycarbonyl)-3-methylpiperazine (Oakwood Co., 1.36 g), 5-bromo-2-chlorobenzotrifluoride (Tokyo Chemical Industry CO., LTD., 2.0 g), 2-(di-tert-phosphino) biphenyl (STREM, 41 mg), tris(dibenzylideneacetone)dipalladium (Aldrich Co., 62 mg) and sodium tert-butoxide (980 mg) were added to toluene (10 ml), and the mixture was stirred with heating at 60° C. for 3 hr. After completion of the reaction, the insoluble material was filtered off, and the filtrate was evaporated under reduced pressure. The obtained residue was purified by silica gel column chromatography (elution solvent: hexane-ethyl acetate (7:1-3:1)). A 4N hydrochloric acid-ethyl acetate solution was added to the obtained solid and the mixture was stirred for 5 hr. Diethyl ether was added thereto, and the precipitated solid was collected by filtration to give 1-[4-chloro-3-(trifluoromethyl)phenyl]-2-methylpiperazine hydrochloride (692 mg, yield 32%).

$^1$H-NMR(400 MHz, DMSO-d$_6$)δ(ppm): 1.11-1.23(3H, m), 3.01-3.30(5H, m), 4.27-4.31(1H, m), 7.21-7.55(3H, m), 9.10(1H, s), 9.61(1H, s).

Starting Material Synthetic Example 81

Phenyllithium (0.94 M, 27 ml) was dissolved in diethyl ether (50 ml), and the mixture was cooled to −78° C. 1-Benzyl-3-methyl-4-piperidone (KANTO CHEMICAL CO. INC., 5 g) was added, and the mixture was stirred for 2 hr. After completion of the reaction, water was added, and the mixture was extracted three times with ethyl acetate. The organic layer was dried and the solvent was evaporated under reduced pressure. The obtained residue was purified by silica gel column chromatography (elution solvent: hexane-ethyl acetate (4:1-0:1)). Phosphoric acid (40 g) and diphosphorus pentoxide (45 g) were added to the obtained oil, and the mixture was stirred with heating at 100° C. for 5 hr. After completion of the reaction, the reaction mixture was poured into water, basified with 1N sodium hydroxide and extracted four times with hexane. The organic layer was washed with water, and dried. The solvent was evaporated under reduced pressure to give a brown oil. The oil was dissolved in 1,2-dichloroethane. The mixture was cooled to 0° C. and 1-chloroethyl chloroformate (857 mg) was added. After heating under reflux for 5 hr, the reaction solution was concentrated. Methanol (10 ml) was added and the mixture was heated under reflux for 2 hr. After completion of the reaction, the reaction mixture was basic (pH=9) with a 1N aqueous sodium hydroxide solution, and extracted three times with chloroform. The organic layer was dried and the solvent was evaporated under reduced pressure to give 5-methyl-4-phenyl-1,2,3,6-tetrahydropyridine (1.00 g, yield 90%).

$^1$H-NMR(400 MHz, DMSO-d$_6$)δ(ppm): 1.51(3H, s), 2.14-3.05(6H, m), 7.16-7.39(5H, m).

Starting Material Synthetic Example 82

4-[4-Chloro-3-(trifluoromethyl)phenyl]-4-hydroxypiperidine (ACROS CO., 2.2 g) was dissolved in tetrahydrofuran (10 ml), di-tert-butyl bicarbonate (1.9 g) and triethylamine (2 ml) were added, and the mixture was stirred for 8 hr. The reaction mixture was concentrated and the obtained residue was purified by silica gel column chromatography (elution solvent: hexane-ethyl acetate (1:1-0:1)) to give 4-[4-chloro-3-(trifluoromethyl)phenyl]-4-hydroxy-1-piperidinecarboxylic acid tert-butyl ester (2.8 g, yield 96%).

$^1$H-NMR(400 MHz, DMSO-d$_6$)δ(ppm): 1.42(9H, s), 1.56-1.59(2H, m), 1.81-1.88(2H, m), 3.09-3.11(2H, m), 3.86-3.88 (2H, m), 5.41(1H, s), 7.65-7.93(3H, m).

4-[4-Chloro-3-(trifluoromethyl)phenyl]-4-hydroxy-1-piperidinecarboxylic acid tert-butyl ester (2.8 g) was dissolved in methylene chloride (20 ml) and the mixture was cooled to −78° C. DEOXO-FLUOR (trademark) (APOLLO CO., 1.8 g) was added, and the mixture was stirred for 2 hr. Then, after stirring at room temperature for 2 hr, water was added, and the mixture was extracted three times with chloroform. The organic layer was dried and the solvent was evaporated under reduced pressure. The obtained residue was purified by silica gel column chromatography (elution solvent: hexane:ethyl acetate(10:1-5:1)) to give a solid. 1,4-Dioxane (20 ml) and 10% aqueous sulfuric acid (5 ml) were added to the solid, and the mixture was stirred with heating at 70° C. for 1.5 hr. After completion of the reaction, the reaction system was basified (pH=9) with a 1N aqueous sodium hydroxide solution, and extracted three times with chloroform. The organic layer was dried and the solvent was evaporated under reduced pressure to give 4-[4-chloro-3-(trifluoromethyl)phenyl]-4-fluoropiperidine (655 mg, yield 31%).

$^1$H-NMR(400 MHz, DMSO-d$_6$)δ(ppm): 1.90-2.08(4H, m), 2.71-2.94(4H, m), 7.65-7.77(3H, m).

Starting Material Synthetic Example 83

The compound (2.0 g) of Example 1, ethyl chloroformate (0.5 ml) and pyridine (0.4 ml) were dissolved in tetrahydrofuran (20 ml), and the mixture was heated under reflux for 2 hr. After completion of the reaction, the reaction solution was concentrated. Water was added, and the precipitated solid was collected by filtration. The solid was washed with acetonitrile to give 3-({4-[4-chloro-3-(trifluoromethyl)phenyl]-4-hydroxypiperidin-1-yl}carbonylamino)-1H-indazole-1-carboxylic acid ethyl ester (1.8 g, yield 75%).

$^1$H-NMR(400 MHz, DMSO-d$_6$)δ(ppm): 1.37-1.40(3H, m), 1.65(2H, d, J=13.2 Hz), 3.25-3.26(2H, m), 4.13(2H, d, J=13.2 Hz), 4.44-4.49(2H, m), 5.47(1H, s), 7.31-8.12(7H, m), 9.77(1H, s).

Starting Material Synthetic Example 84

By a similar operation as in Starting Material Synthetic Example 83, 3-({[4-(4-fluorophenyl)-3,6-dihydropyridine-1(2H)-yl]carbonyl}amino)-1H-indazole-1-carboxylic acid ethyl ester (3.7 g, yield 66%) was obtained from compound (4.32 g) of Example 50.

$^1$H-NMR(400 MHz, DMSO-d$_6$)δ(ppm): 1.23-1.41(2H, m), 2.50-2.56(2H, m), 3.72-3.76(2H, m), 4.20-4.21(2H, m), 4.44-4.49(2H, m), 6.20(1H, s), 7.16-8.12(8H, m), 9.85(1H, s).

Starting Material Synthetic Example 85

By a similar operation as in Starting Material Synthetic Example 39, 4-(3-fluorophenyl)-1,2,3,6-tetrahydropyridine (666 mg, yield 47%) was obtained from 3-fluorophenylboric acid (Aldrich Co., 632 mg).

$^1$H-NMR(400 MHz, DMSO-d$_6$)δ(ppm): 2.39-2.40(2H, m), 3.00-3.02(2H, m), 3.47-3.48(2H, m), 5.99(1H, s), 6.97-7.35(4H, m).

Starting Material Synthetic Example 86

By a similar operation as in Starting Material Synthetic Example 50, 4-(3-methyl-2-thienyl)-1,2,3,6-tetrahydropyridine hydrochloride (731 mg, yield 34%) was obtained from a 3-methyl-2-thienylmagnesiumbromide-tetrahydrofuran solution (Aldrich Co., 0.5 M, 22 ml).

$^1$H-NMR(400 MHz, DMSO-d$_6$)δ(ppm): 2.25(3H, s), 2.60-2.62(2H, m), 3.25-3.26(2H, m), 3.40-3.42(2H, m), 3.71-3.72(2H, m), 5.87(1H, s), 6.91(1H, d, J=3.7 Hz), 7.39(1H, d, J=3.7 Hz).

Starting Material Synthetic Example 87

By a similar operation as in Starting Material Synthetic Example 39, 4-(2-thienyl)-1,2,3,6-tetrahydropyridine (342 mg, yield 56%) was obtained from 2-thienylboric acid (Aldrich Co., 576 mg).

$^1$H-NMR(400 MHz, DMSO-d$_6$)δ(ppm): 2.37-2.38(2H, m), 2.92-2.94(2H, m), 3.82-3.83(2H, m), 6.10(1H, s), 6.92-7.37(3H, m).

Starting Material Synthetic Example 88

4-[3-(Trifluoromethyl)phenyl]-4-hydroxypiperidine (Aldrich Co., 2.2 g) was suspended in trifluoromethylacetic acid (10 ml) and the mixture was stirred with heating at 80° C. for 5 hr. After completion of the reaction, the reaction mixture was cooled to room temperature, neutralized with saturated aqueous sodium hydrogencarbonate solution and extracted with ethyl acetate. The organic layer was dried and the solvent was evaporated under reduced pressure to give 4-[3-(trifluoromethyl)phenyl]-1,2,3,6-tetrahydropyridine (791 mg, yield 67%).

$^1$H-NMR(300 MHz, DMSO-d$_6$)δ(ppm): 2.45-2.57(2H, m), 3.12-3.16(2H, m), 3.58-3.60(2H, m), 6.34-6.36(1H, m), 7.58-7.66(2H, m), 7.76-7.78(2H, m).

Starting Material Synthetic Example 89

By a similar operation as in Starting Material Synthetic Example 50, 3-(3-fluorophenyl)piperidin-3-ol hydrochloride (450 mg, yield 38%) was obtained from 1-(tert-butoxycarbonyl)-3-piperidone (Aldrich Co., 1.03 g) and 3-fluorophenylmagnesiumbromide (Tokyo Chemical Industry CO., LTD., 1 M, 6 ml).

$^1$H-NMR(300 MHz, DMSO-d$_6$)δ(ppm): 1.69-1.75(2H, m), 1.95-2.09(2H, m), 2.95-3.00(2H, m), 3.16-3.30(4H, m), 5.99(1H, s), 7.10-7.16(1H, m), 7.37-7.45(3H, m), 8.33(1H, s), 9.51(1H, s).

Starting Material Synthetic Example 90 Missing Number

Starting Material Synthetic Example 91

By a similar operation as in Starting Material Synthetic Example 59, 4-(2-methylphenyl)piperidin-4-ol (1.3 g, yield 28%) was obtained from 2-iodotoluene (Tokyo Chemical Industry CO., LTD., 5.0 g).

$^1$H-NMR(300 MHz, DMSO-d$_6$)δ(ppm): 1.71(2H, d, J=12.0 Hz), 1.80-1.90(2H, m), 2.55(3H, s), 2.73(2H, d, J=12.0 Hz), 4.64(1H, s), 7.09-7.15(2H, m), 7.36-7.38(1H, m).

Starting Material Synthetic Example 92

By a similar operation as in Starting Material Synthetic Example 59, 4-(2-fluoro-5-methylphenyl)piperidin-4-ol (1.2 g, yield 21%) was obtained from 3-bromo-4-fluorotoluene (Tokyo Chemical Industry CO., LTD., 5.2 g).

¹H-NMR(300 MHz, DMSO-d₆)δ(ppm): 1.43-1.47 (2H, m), 1.99-2.08(2H, m), 2.28(3H, s), 2.68-2.72(2H, m), 2.89-2.97(2H, m), 4.94(1H, s), 6.92-7.04(2H, m), 7.40-7.43(1H, m).

Starting Material Synthetic Example 93

By a similar operation as in Starting Material Synthetic Example 59, 4-(3-chloro-2-methylphenyl)piperidin-4-ol (355 mg, yield 19%) was obtained from 2-chloro-6-iodotoluene (Tokyo Chemical Industry CO., LTD., 2.1 g).
¹H-NMR(300 MHz, DMSO-d₆)δ(ppm): 1.76-1.93(4H, m), 2.60(3H, s), 2.76-2.80(2H, m), 2.95-3.04(2H, m), 4.94 (1H, s), 7.14-7.19(1H, m), 7.32-7.39(2H, m).

Starting Material Synthetic Example 94

By a similar operation as in Starting Material Synthetic Example 59, 4-(3-chloro-4-methylphenyl)piperidin-4-ol (86 mg, yield 2%) was obtained from 2-chloro-4-iodotoluene (Tokyo Chemical Industry CO., LTD., 5.0 g).
¹H-NMR(300 MHz, DMSO-d₆)δ(ppm): 1.68-1.72(2H, m), 2.06-2.17(2H, m), 2.31(3H, s), 3.08-3.15(4H, m), 5.47 (1H, s), 7.27(1H, d, J=8.0 Hz), 7.35(1H, d, J=8.0 Hz), 7.46 (1H, s).

Starting Material Synthetic Example 95

By a similar operation as in Starting Material Synthetic Example 59, 4-(3-fluoro-4-methylphenyl)piperidin-4-ol (1.5 g, yield 34%) was obtained from 2-fluoro-4-iodotoluene (LANCASTER CO., 5.2 g).
¹H-NMR(300 MHz, DMSO-d₆)δ(ppm): 1.45-1.49(2H, m), 1.71-1.80(2H, m), 2.19(3H, s), 2.70-2.74(2H, m), 2.86-2.94(2H, m), 4.85(1H, s), 7.13-7.23(3H, m).

Starting Material Synthetic Example 96

By a similar operation as in Starting Material Synthetic Example 43, 4-(3-fluoro-2-methylphenyl)piperidin-4-ol (970 mg, yield 41%) was obtained from 2-bromo-6-fluorotoluene (LANCASTER CO., 2.1 g).
¹H-NMR(300 MHz, DMSO-d₆)δ(ppm): 1.72-1.89(4H, m), 2.45(3H, m), 2.73-2.77(2H, m), 2.93-3.02(2H, m), 4.85 (1H, s), 6.99-7.04(1H, m), 7.12-7.24(2H, m).

Starting Material Synthetic Example 97

By a similar operation as in Starting Material Synthetic Example 59, 4-(5-fluoro-2-methylphenyl)piperidin-4-ol (1.2 g, yield 27%) was obtained from 4-fluoro-2-iodotoluene (LANCASTER CO., 5.1 g).
¹H-NMR(300 MHz, DMSO-d₆)δ(ppm): 1.62-1.66(2H, m), 1.83-1.93(2H, m), 2.51(3H, s), 2.72-2.75(2H, m), 2.91-2.99(2H, m), 4.80(1H, s), 6.90-6.96(1H, m), 7.10-7.21(2H, m).

Starting Material Synthetic Example 98

By a similar operation as in Starting Material Synthetic Example 59, 4-(4-fluoro-3-methylphenyl)piperidin-4-ol (935 mg, yield 21%) was obtained from 2-fluoro-5-iodotoluene (LANCASTER CO., 5.0 g).
¹H-NMR(300 MHz, DMSO-d₆)δ(ppm): 1.47-1.51(2H, m), 1.72-1.78(2H, m), 2.22(3H, s), 2.71-2.75(2H, m), 2.87-2.95(2H, m), 4.79(1H, s), 7.01-7.07(1H, m), 7.25-7.30(1H, m), 7.33-7.36(1H, m).

Starting Material Synthetic Example 99

By a similar operation as in Starting Material Synthetic Example 59, 4-(4-methylphenyl)piperidin-4-ol (1.3 g, yield 29%) was obtained from 4-iodotoluene (Tokyo Chemical Industry CO., LTD., 5.0 g).
¹H-NMR(300 MHz, DMSO-d₆)δ(ppm): 1.48(2H, d, J=12.3 Hz), 1.72-1.80(2H, m), 2.26(3H, s), 2.72(2H, d, J=12.3 Hz), 2.88-2.96(2H, m), 4.70(s, 1H),7.11(2H, d, J=8.1 Hz), 7.33(2H, d, J=8.1 Hz).

Starting Material Synthetic Example 100

By a similar operation as in Starting Material Synthetic Example 43, 4-(3-fluoro-5-methylphenyl)piperidin-4-ol (962 mg, yield 19%) was obtained from 3-bromo-5-fluorotoluene (APOLLO CO., 4.9 g).
¹H-NMR(300 MHz, DMSO-d₆)δ(ppm): 1.48-1.52(2H, m), 1.74-1.88(2H, m), 2.32(3H, s), 2.76-2.80(2H, m), 2.89-2.93(2H, m), 4.95(1H, s), 6.83-6.87(1H, m), 7.01-7.04(1H, m), 7.09(1H, s).

Starting Material Synthetic Example 101

By a similar operation as in Starting Material Synthetic Example 43, 4-(2,5-dimethylphenyl)piperidin-4-ol (3.12 g, yield 58%) was obtained from 2-bromo-β-xylene (Tokyo Chemical Industry CO., LTD., 5.0 g).
¹H-NMR(400 MHz, DMSO-d₆)δ(ppm): 1.68(2H, d, J=12.5 Hz), 1.79-1.88(2H, m), 2.24(3H, s), 2.70(2H, d, J=12.5 Hz), 2.91-3.00(2H, m), 4.54(1H, s), 6.90(1H, d, J=7.8 Hz), 6.97(1H, d, J=7.8 Hz), 7.20(1H, s).

Starting Material Synthetic Example 102

3-Amino-2-methylbenzotrifluoride (Aldrich Co., 5.25 g) was added to a mixture of concentrated hydrochloric acid (20 ml) and water (20 ml) and, under ice-cooling, sodium nitrite (3.31 g) dissolved in water (10 ml) was added dropwise thereto. The mixture was stirred at 0° C. for 1 hr. Potassium iodide (9.95 g) dissolved in water (20 ml) was added to the reaction mixture. The mixture was stirred at −4° C. for 2 hr. The mixture was adjusted to pH 11 or above with a 6N aqueous sodium hydroxide solution, and an aqueous thiosodium sulfate solution was added thereto. The mixture was extracted with ethyl acetate. The extract was washed with saturated brine and dried. The solvent was evaporated under reduced pressure to give a brown oil. The oil was purified by silica gel column chromatography (elution solvent: hexane) to give 3-iodo-2-methylbenzotrifluoride (6.28 g, yield 73%).
¹H-NMR(400 MHz, DMSO-d₆)δ(ppm): 2.52(3H, s), 7.16 (1H, t, J=7.8 Hz), 7.73(1H, d, J=7.8 Hz), 8.18(1H, d, J=7.8 Hz).

By a similar operation as in Starting Material Synthetic Example 59, 4-[2-methyl-3-(trifluoromethyl)phenyl]piperidin-4-ol (2.18 g, yield 32%) was obtained from 3-iodo-2-methylbenzotrifluoride (6.28 g).
¹H-NMR(400 MHz, DMSO-d₆)δ(ppm): 1.76-1.91(4H, m), 2.69-2.78(2H, m), 2.71(3H, s), 2.94-3.04(2H, m), 4.91 (1H, s), 7.34(1H, t, J=7.8 Hz), 7.57(1H, d, J=7.8 Hz), 7.70 (1H, d, J=7.8 Hz).

Starting Material Synthetic Example 103

By a similar operation as in Starting Material Synthetic Example 102, 3-iodo-4-methylbenzotrifluoride (7.46 g, yield 77%) was obtained from 3-amino-4-methylbenzotrifluoride (Aldrich Co., 5.90 g).

$^1$H-NMR(400 MHz, DMSO-$d_6$)δ(ppm): 2.45(3H, s), 7.55 (1H, d, J=7.8 Hz), 7.68(1H, d, J=7.8 Hz), 8.11(1H, s).

By a similar operation as in Starting Material Synthetic Example 59, 4-[2-methyl-5-(trifluoromethyl)phenyl]piperidin-4-ol (2.79 g, yield 41%) was obtained from 3-iodo-4-methylbenzotrifluoride (7.46 g).

$^1$H-NMR(400 MHz, DMSO-$d_6$)δ(ppm): 1.62-1.70(2H, m), 1.87-1.97(2H, m), 2.63(3H, s), 2.70-2.78(2H, m), 2.91-3.01(2H, m), 4.90(1H, s), 7.34(1H, d, J=7.8 Hz), 7.47(1H, d, J=7.8 Hz), 7.73(1H, s).

Starting Material Synthetic Example 104

By synthesizing in the same manner as in Starting Material Synthetic Example 59, 4-(3,4-dimethylphenyl)piperidin-4-ol (2.42 g, yield 66%) was obtained from 4-iodo-o-xylene (Tokyo Chemical Industry CO., LTD., 5 g).

$^1$H-NMR(400 MHz, DMSO-$d_6$)δ(ppm): 1.45-1.48(2H, m), 1.71-1.79(2H, m), 2.17(3H, s), 2.18(3H, s), 2.68-2.71 (2H, m), 2.87-2.94(2H, m), 5.74(1H, s), 7.03-7.21(3H, m).

Starting Material Synthetic Example 105

By synthesizing in the same manner as in Starting Material Synthetic Example 59, 4-(3,5-dimethylphenyl)piperidin-4-ol (1.78 g, yield 48%) was obtained from 5-iodo-m-xylene (Tokyo Chemical Industry CO., LTD., 5 g).

$^1$H-NMR(400 MHz, DMSO-$d_6$)δ(ppm): 1.46-1.49(2H, m), 1.73-1.80(2H, m), 2.25(6H, m), 2.71-2.74(2H, m), 2.88-2.95(2H, m), 5.73(1H, s), 6.81(1H, s), 7.06(2H, m).

Starting Material Synthetic Example 106

By synthesizing in the same manner as in Starting Material Synthetic Example 59, 4-(2,3-dimethylphenyl)piperidin-4-ol (1.46 g, yield 39%) was obtained from 3-iodo-o-xylene (Tokyo Chemical Industry CO., LTD., 5 g).

$^1$H-NMR(400 MHz, DMSO-$d_6$)δ(ppm): 1.75-1.98(4H, m), 2.20(3H, s), 2.45(3H, s), 2.72-2.75(2H, m), 2.92-2.99 (2H, m), 5.75(1H, s), 6.98-7.25(3H, m).

The structural formulas of the compounds of respective Starting Material Synthetic Examples are shown in the following.

[Formulas 12]

| | |
|---|---|
| Starting Material Synthetic Example 1 | 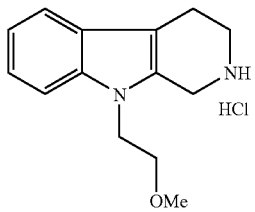 |
| Starting Material Synthetic Example 2 | 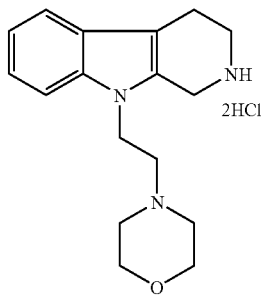 |
| Starting Material Synthetic Example 3 | 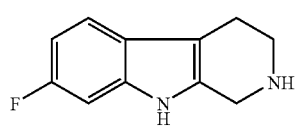 |
| Starting Material Synthetic Example 4 | 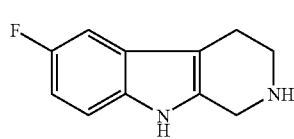 |
| Starting Material Synthetic Example 5 | 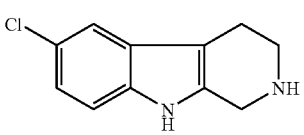 |
| Starting Material Synthetic Example 6 | 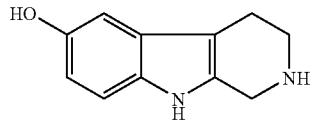 |
| Starting Material Synthetic Example 7 | 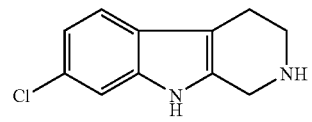 |
| Starting Material Synthetic Example 8 | 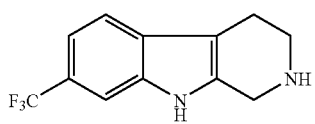 |
| Starting Material Synthetic Example 9 | 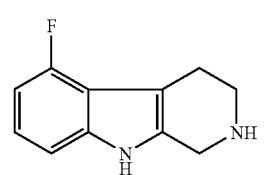 |
| Starting Material Synthetic Example 10 | 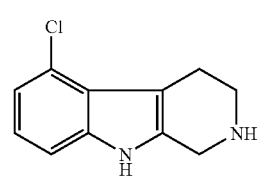 |
| Starting Material Synthetic Example 11 | 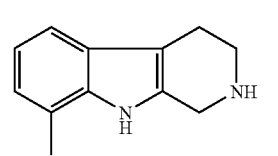 |

-continued

[Formulas 13]

| | |
|---|---|
| Starting Material Synthetic Example 12 | 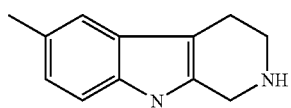 |
| Starting Material Synthetic Example 13 | 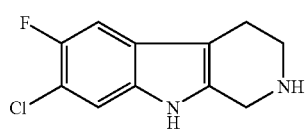 |
| Starting Material Synthetic Example 14 | 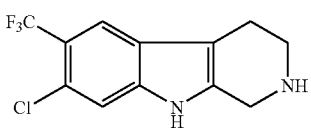 |
| Starting Material Synthetic Example 15 | 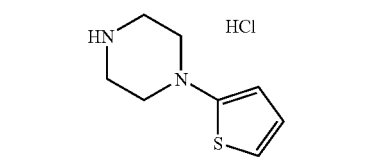 |
| Starting Material Synthetic Example 16 | 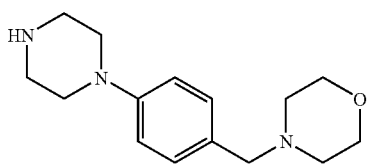 |
| Starting Material Synthetic Example 17 | 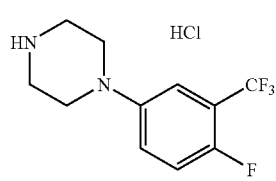 |
| Starting Material Synthetic Example 18 | 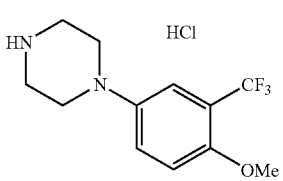 |
| Starting Material Synthetic Example 19 |  |
| Starting Material Synthetic Example 20 | 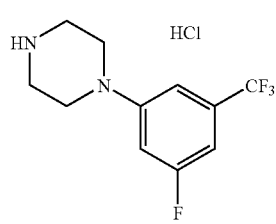 |
| Starting Material Synthetic Example 21 | 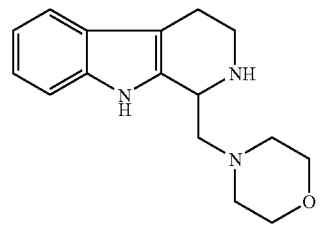 |
| Starting Material Synthetic Example 22 | 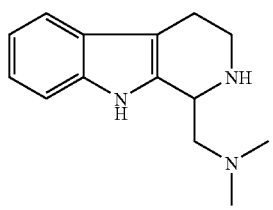 |
| Starting Material Synthetic Example 23 | 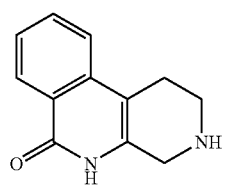 |
| Starting Material Synthetic Example 24 | 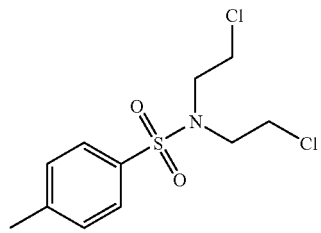 |
| Starting Material Synthetic Example 25 | 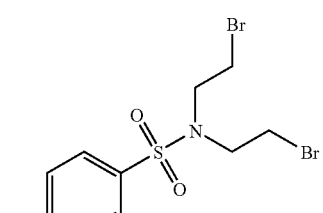 |
| Starting Material Synthetic Example 26 | 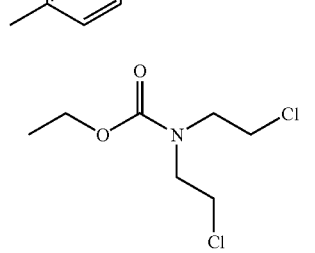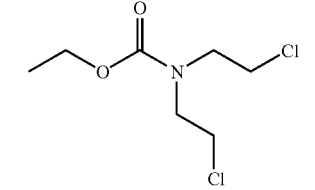 |
| Starting Material Synthetic Example 27 | 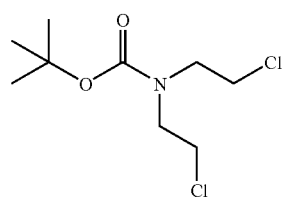 |

| | | | | |
|---|---|---|---|---|
| Starting Material Synthetic Example 28 | 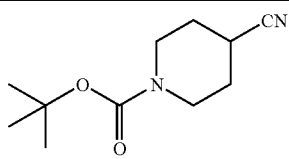 | | Starting Material Synthetic Example 38 | 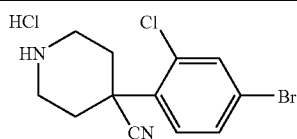 |
| Starting Material Synthetic Example 29 | 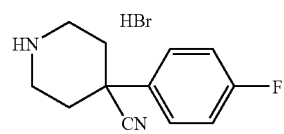 | | Starting Material Synthetic Example 39 | 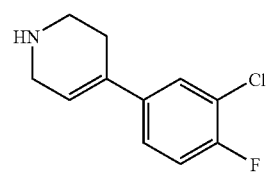 |
| Starting Material Synthetic Example 30 | 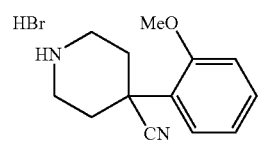 | | Starting Material Synthetic Example 40 | 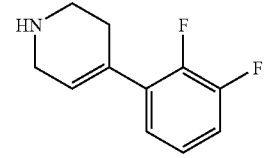 |
| Starting Material Synthetic Example 31 | 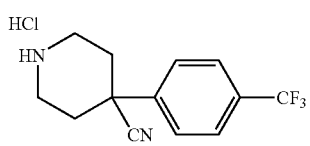 | | Starting Material Synthetic Example 41 |  |
| Starting Material Synthetic Example 32 | 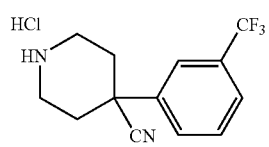 | | Starting Material Synthetic Example 42 | 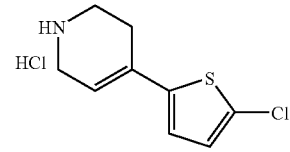 |
| Starting Material Synthetic Example 33 | 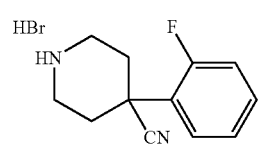 | | | |

[Formulas 14]

| | |
|---|---|
| Starting Material Synthetic Example 34 | 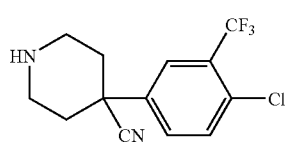 |
| Starting Material Synthetic Example 43 | 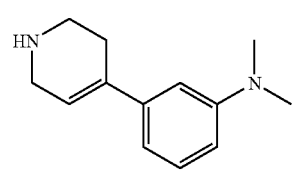 |
| Starting Material Synthetic Example 35 | 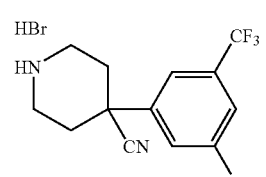 |
| Starting Material Synthetic Example 44 | 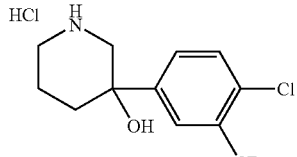 |
| Starting Material Synthetic Example 36 | 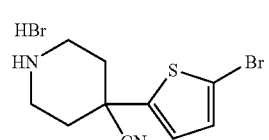 |
| Starting Material Synthetic Example 45 | 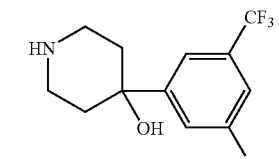 |
| Starting Material Synthetic Example 37 | 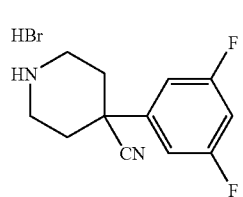 |
| Starting Material Synthetic Example 46 | 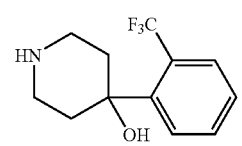 |

-continued

| | | |
|---|---|---|
| Starting Material Synthetic Example 47 | 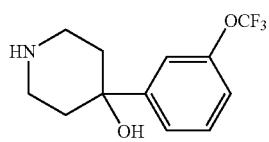 | |
| Starting Material Synthetic Example 48 | 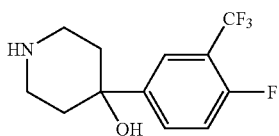 | |
| Starting Material Synthetic Example 49 | 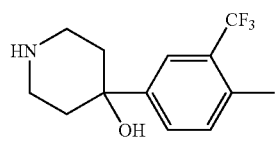 | |
| Starting Material Synthetic Example 50 | 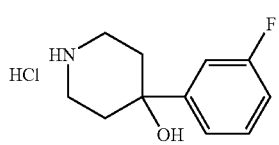 | |
| Starting Material Synthetic Example 51 | 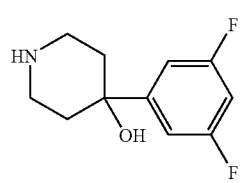 | |
| Starting Material Synthetic Example 52 | 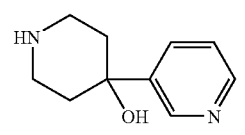 | |
| Starting Material Synthetic Example 53 | 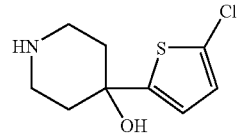 | |
| Starting Material Synthetic Example 54 | 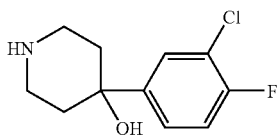 | |
| Starting Material Synthetic Example 55 | 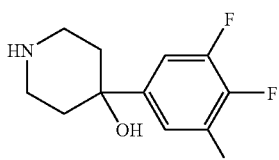 | |
| Starting Material Synthetic Example 56 | 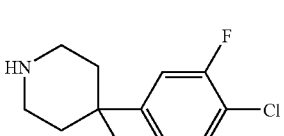 | |

-continued

| | | |
|---|---|---|
| Starting Material Synthetic Example 57 | 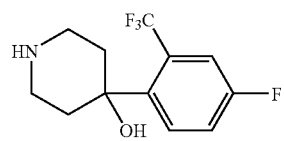 | |
| Starting Material Synthetic Example 58 | 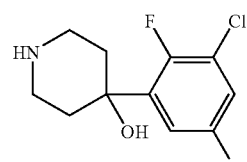 | |
| Starting Material Synthetic Example 59 | 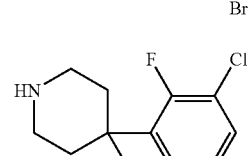 | |
| Starting Material Synthetic Example 60 | 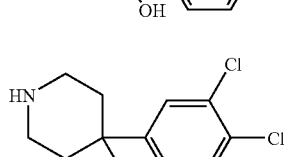 | |
| Starting Material Synthetic Example 61 | 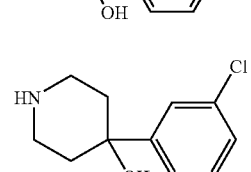 | |
| Starting Material Synthetic Example 62 | 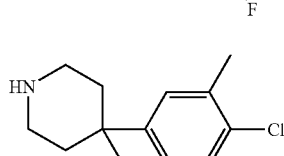 | |
| Starting Material Synthetic Example 63 | 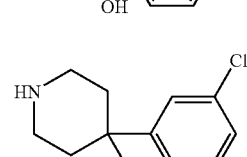 | |
| Starting Material Synthetic Example 64 | 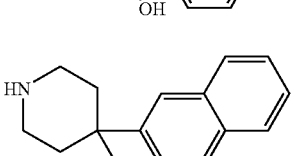 | |
| Starting Material Synthetic Example 65 | 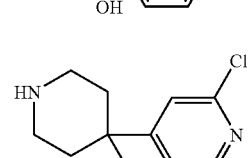 | |
| Starting Material Synthetic Example 66 | 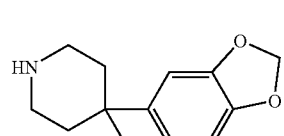 | |

[Formulas 15]

| | |
|---|---|
| Starting Material Synthetic Example 67 | 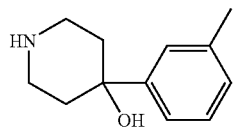 |
| Starting Material Synthetic Example 68 | 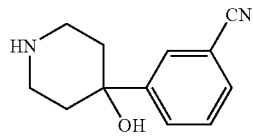 |
| Starting Material Synthetic Example 69 | 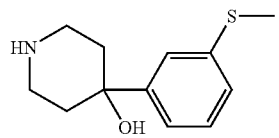 |
| Starting Material Synthetic Example 70 | 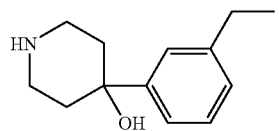 |
| Starting Material Synthetic Example 71 | 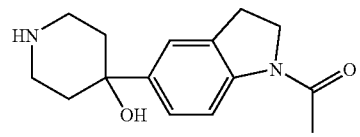 |
| Starting Material Synthetic Example 72 | 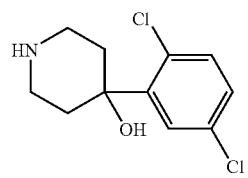 |
| Starting Material Synthetic Example 73 | 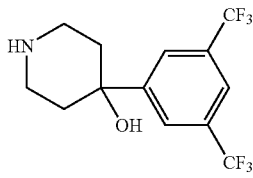 |
| Starting Material Synthetic Example 74 | 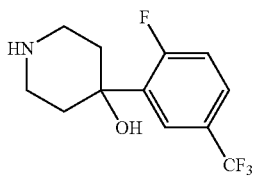 |
| Starting Material Synthetic Example 75 | 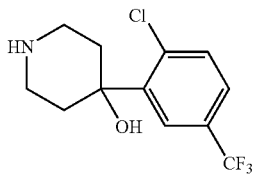 |
| Starting Material Synthetic Example 76 | 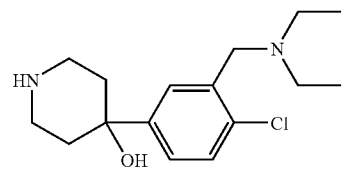 |
| Starting Material Synthetic Example 77 | 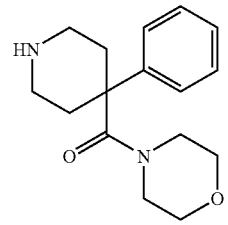 |
| Starting Material Synthetic Example 78 | 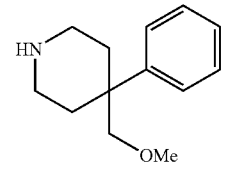 |
| Starting Material Synthetic Example 79 | 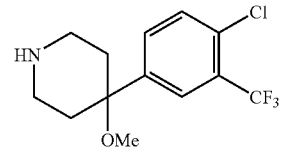 |
| Starting Material Synthetic Example 80 | 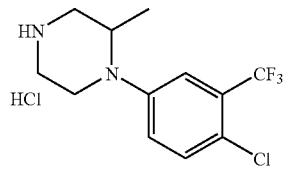 |
| Starting Material Synthetic Example 81 | 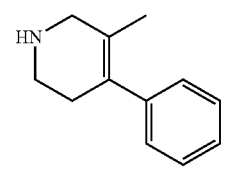 |
| Starting Material Synthetic Example 82 | 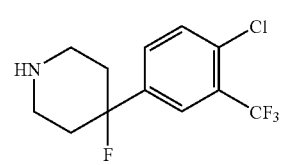 |
| Starting Material Synthetic Example 83 | 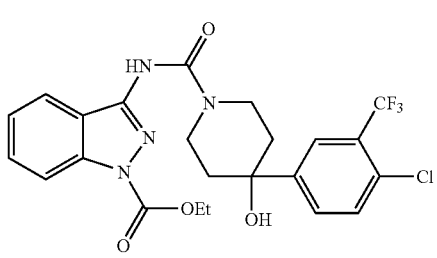 |

-continued

| | |
|---|---|
| Starting Material Synthetic Example 84 | (indazole-carboxamide with tetrahydropyridine-4-fluorophenyl and N-CO-OEt) |
| Starting Material Synthetic Example 85 | 4-(3-fluorophenyl)-1,2,3,6-tetrahydropyridine |
| Starting Material Synthetic Example 86 | 4-(3-methylthiophen-2-yl)-1,2,3,6-tetrahydropyridine·HCl |
| Starting Material Synthetic Example 87 | 4-(thiophen-2-yl)-1,2,3,6-tetrahydropyridine |
| Starting Material Synthetic Example 88 | 4-(3-trifluoromethylphenyl)-1,2,3,6-tetrahydropyridine |

[Formulas 16]

| | |
|---|---|
| Starting Material Synthetic Example 89 | 4-(3-fluorophenyl)-4-hydroxypiperidine·HCl |
| Starting Material Synthetic Example 90 | missing number |
| Starting Material Synthetic Example 91 | 4-hydroxy-4-(2-methylphenyl)piperidine |
| Starting Material Synthetic Example 92 | 4-(2-fluoro-5-methylphenyl)-4-hydroxypiperidine |
| Starting Material Synthetic Example 93 | 4-(3-chloro-2-methylphenyl)-4-hydroxypiperidine |
| Starting Material Synthetic Example 94 | 4-(3-chloro-4-methylphenyl)-4-hydroxypiperidine |
| Starting Material Synthetic Example 95 | 4-(3-fluoro-4-methylphenyl)-4-hydroxypiperidine |
| Starting Material Synthetic Example 96 | 4-(3-fluoro-2-methylphenyl)-4-hydroxypiperidine |
| Starting Material Synthetic Example 97 | 4-(5-fluoro-2-methylphenyl)-4-hydroxypiperidine |
| Starting Material Synthetic Example 98 | 4-(4-fluoro-3-methylphenyl)-4-hydroxypiperidine |
| Starting Material Synthetic Example 99 | 4-hydroxy-4-(4-methylphenyl)piperidine |
| Starting Material Synthetic Example 100 | 4-(3-fluoro-5-methylphenyl)-4-hydroxypiperidine |
| Starting Material Synthetic Example 101 | 4-(2,5-dimethylphenyl)-4-hydroxypiperidine |
| Starting Material Synthetic Example 102 | 4-hydroxy-4-(2-methyl-3-trifluoromethylphenyl)piperidine |

| | |
|---|---|
| Starting Material Synthetic Example 103 | 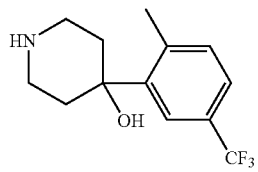 |
| Starting Material Synthetic Example 104 | 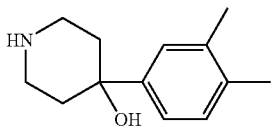 |
| Starting Material Synthetic Example 105 | 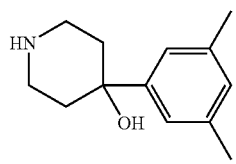 |
| Starting Material Synthetic Example 106 | 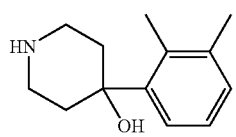 |

Example 1

Ethyl 1H-indazol-3-ylcarbamate (synthesized according to the method described in Tetrahedron, 1976, 32(4), 493) (200 mg) and 4-[4-chloro-3-(trifluoromethyl)phenyl]-4-hydroxypiperidine (ACROS CO., 272 mg) were dissolved in dimethyl sulfoxide (2 ml). Potassium fluoride-alumina (Aldrich Co., 40 wt %, 200 mg) was added to the solution, and the mixture was stirred with heating at 100° C. for 2 hr. After completion of the reaction, the solid was collected by filtration and washed with methanol. The filtrate was concentrated, and 1N aqueous hydrochloric acid was added. The precipitated solid was collected by filtration and vacuum dried. The obtained solid was washed with diethyl ether and dried to give 4-[4-chloro-3-(trifluoromethyl)phenyl]-4-hydroxy-1-piperidinecarboxylic acid (1H-indazol-3-yl)amide (280 mg, yield 66%).

$^1$H-NMR(400 MHz, DMSO-$d_6$)δ(ppm): 1.61(2H, d, J=12.5 Hz), 1.59-1.63(2H, m), 3.18-3.26(2H, m), 4.09(2H, d, J=12.5 Hz), 5.45(1H, s), 6.97-7.99(7H, m), 8.96(1H, s), 12.43 (1H, s). MS(ESI)m/z:439[M+H]$^+$.

Example 2

By a similar operation as in Example 1, 4-hydroxy-4-phenyl-1-piperidinecarboxylic acid (1H-indazol-3-yl)amide (331 mg, yield 10%) was obtained from Ethyl 1H-indazol-3-ylcarbamate (202 mg) and 4-hydroxy-4-phenylpiperidine (Tokyo Chemical Industry CO., LTD., 175 mg).

$^1$H-NMR(300 MHz, DMSO-$d_6$)δ(ppm): 1.62-1.64(2H, m), 1.89-1.96(2H, m), 3.23-3.31(2H, m), 4.06-4.10(2H, m), 5.11(1H, s), 7.02-7.63(9H, m), 8.97(1H, s), 12.46(1H, s). MS(ESI)m/z:337[M+H]$^+$.

Example 3

By a similar operation as in Example 1, 4-hydroxy-4-[3-(trifluoromethyl)phenyl]-1-piperidinecarboxylic acid (1H-indazol-3-yl)amide (197 mg, yield 50%) was obtained from ethyl 1H-indazol-3-ylcarbamate (200 mg) and 4-hydroxy-4-[3-(trifluoromethyl)phenyl]piperidine (ACROS CO., 238 mg).

$^1$H-NMR(400 MHz, DMSO-$d_6$)δ(ppm): 1.62(1H, d, J=12.5 Hz), 1.94-1.96(2H, m), 3.24-3.31(2H, m), 4.09(2H, d, J=12.5 Hz), 5.36(1H, s), 7.00-7.85(8H, m), 8.96(1H, s), 12.43 (1H, s). MS(ESI)m/z:405[M+H]$^+$.

Example 4

By a similar operation as in Example 1, 4-(4-chlorophenyl)-4-hydroxy-1-piperidinecarboxylic acid (1H-indazol-3-yl)amide (360 mg, yield 78%) was obtained from ethyl 1H-indazol-3-ylcarbamate (199 mg) and 4-(chlorophenyl)-4-hydroxypiperidine (Tokyo Chemical Industry CO., LTD., 205 mg).

$^1$H-NMR(300 MHz, DMSO-$d_6$)δ(ppm): 1.60-1.64(2H, m), 1.89(2H, m), 3.25-3.39(2H, m), 4.04-4.09(2H, m), 5.27 (1H, s), 7.02-7.62(8H, m), 9.56(1H, s), 12.46(1H, s). MS(ESI)m/z:371[M+H]$^+$.

Example 5

By a similar operation as in Example 1, 4-(4-fluorophenyl)-4-hydroxy-1-piperidinecarboxylic acid (1H-indazol-3-yl)amide (340 mg, yield 21%) was obtained from ethyl 1H-indazol-3-ylcarbamate (226 mg) and 4-(fluorophenyl)-4-hydroxypiperidine (Oakwood Co., 220 mg).

$^1$H-NMR(300 MHz, DMSO-$d_6$)δ(ppm): 1.62-1.66(2H, m), 1.88-1.95(2H, m), 3.22-3.25(2H, m), 4.10-4.15(2H, m), 5.51(1H, s), 7.02-7.73(8H, m), 8.94(1H, s), 12.43(1H, s). MS(ESI)m/z:355[M+H]$^+$.

Example 6

By a similar operation as in Example 1, 4-[3-fluoro-5-(trifluoromethyl)phenyl]-4-hydroxy-1-piperidinecarboxylic acid (1H-indazol-3-yl)amide (2.8 g, yield 7%) was obtained from ethyl 1H-indazol-3-ylcarbamate (3.6 g) and the compound (5.6 g) of Starting Material Synthetic Example 45.

$^1$H-NMR(300 MHz, DMSO-$d_6$)δ(ppm): 1.61-1.66(2H, m), 1.89-1.98(2H, m), 3.21-3.30(2H, m), 4.07-4.11(2H, m), 5.24(1H, s), 6.99-7.64(7H, m), 8.95(1H, s), 12.43(1H, s). MS(ESI)m/z:423[M+H]$^+$.

Example 7

By a similar operation as in Example 1, 4-hydroxy-4-[2-(trifluoromethyl)phenyl]-1-piperidinecarboxylic acid (1H-indazol-3-yl)amide (276 mg, yield 47%) was obtained from ethyl 1H-indazol-3-ylcarbamate (300 mg) and the compound (494 mg) of Starting Material Synthetic Example 46.

$^1$H-NMR(400 MHz, DMSO-$d_6$)δ(ppm): 1.80(2H, d, J=13.2 Hz), 2.07-2.09(2H, m), 4.11(2H, d, J=13.2 Hz), 5.18 (1H, s), 7.00-7.79(8H, m), 8.96(1H, s), 12.45(1H, s). MS(ESI)m/z:405[M+H]$^+$.

Example 8

By a similar operation as in Example 1, 4-hydroxy-4-[3-(trifluoromethoxy)phenyl]-1-piperidinecarboxylic acid (1H-indazol-3-yl)amide (113 mg, yield 27%) was obtained from ethyl 1H-indazol-3-ylcarbamate (205 mg) and the compound (380 mg) of Starting Material Synthetic Example 47.

$^1$H-NMR(400 MHz, DMSO-$d_6$)δ(ppm): 1.63(2H, d, J=12.8 Hz), 1.62-1.66(2H, m), 3.25-3.26(2H, m), 4.12(2H, d, J=12.8 Hz), 5.33(1H, s), 7.01-7.64(8H, m), 8.96(1H, s), 12.44 (1H, s). MS(ESI)m/z:421[M+H]⁺.

Example 9

By a similar operation as in Example 1, 4-[4-fluoro-3-(trifluoromethyl)phenyl]-4-hydroxy-1-piperidinecarboxylic acid (1H-indazol-3-yl)amide (278 mg, yield 45%) was obtained from ethyl 1H-indazol-3-ylcarbamate (300 mg) and the compound (460 mg) of Starting Material Synthetic Example 48.
$^1$H-NMR(400 MHz, DMSO-$d_6$)δ(ppm): 1.64(2H, d, J=12.6 Hz), 1.94-1.97(2H, m), 3.22-3.24(2H, m), 4.11(2H, d, J=12.6 Hz), 5.43(1H, s), 7.00-7.89(7H, m), 8.97(1H, s), 12.44 (1H, s). MS(ESI)m/z:423[M+H]⁺.

Example 10

By a similar operation as in Example 1, 4-hydroxy-4-[4-methyl-3-(trifluoromethyl)phenyl]-1-piperidinecarboxylic acid (1H-indazol-3-yl)amide (164 mg, yield 27%) was obtained from ethyl 1H-indazol-3-ylcarbamate (300 mg) and the compound (518 mg) of Starting Material Synthetic Example 49.
$^1$H-NMR(400 MHz, DMSO-$d_6$)δ(ppm): 1.65(2H, d, J=13.2 Hz), 1.93-1.95(2H, m), 2.54(3H, s), 3.16-3.19(2H, m), 4.11(2H, d, J=13.2 Hz), 5.40(1H, s), 7.00-7.71(7H, m), 8.98(1H, s), 12.46(1H, s). MS(ESI)m/z:419[M+H]⁺.

Example 11

By a similar operation as in Example 1, 4-(3-fluorophenyl)-4-hydroxy-1-piperidinecarboxylic acid (1H-indazol-3-yl)amide (185 mg, yield 45%) was obtained from ethyl 1H-indazol-3-ylcarbamate (239 mg) and the compound (270 mg) of Starting Material Synthetic Example 50.
$^1$H-NMR(400 MHz, DMSO-$d_6$)δ(ppm): 1.61-1.66(2H, m) 1.89-1.98(2H, m), 3.21-3.30(2H, m), 4.07-4.11(2H, m), 5.24 (1H, s), 6.99-7.64(8H, m), 8.94(1H, s), 12.43(1H, s). MS(ESI)m/z:355[M+H]⁺.

Example 12

Ethyl 1H-indazol-3-ylcarbamate (5.3 g), the compound (6.6 g) of Starting Material Synthetic Example 51 and 1,8-diazabicyclo[5,4,0]-7-undecene (hereinafter DBU, 5.9 ml) were dissolved in dioxane (100 ml), and the mixture was heated under reflux for 8 hr. After completion of the reaction, the reaction mixture was concentrated. Water was added to the residue and the precipitated solid was collected by filtration. The solid was recrystallized from methanol-water (10:1) to give 4-(3,5-difluorophenyl)-4-hydroxy-1-piperidinecarboxylic acid (1H-indazol-3-yl)amide (6.8 g, yield 70%).
$^1$H-NMR(400 MHz, DMSO-$d_6$)δ(ppm): 1.61(2H, d, J=12.4 Hz), 1.93-1.94(2H, m), 3.19-3.23(2H, m), 4.10(2H, d, J=12.4 Hz), 5.39(1H, s), 6.99-7.65(7H, m), 8.95(1H, s), 12.45 (1H, s). MS(ESI)m/z:373[M+H]⁺.

Example 13

By a similar operation as in Example 1, 4-hydroxy-4-(3-pyridyl)-1-piperidinecarboxylic acid (1H-indazol-3-yl)amide (307 mg, yield 65%) was obtained from ethyl 1H-indazol-3-ylcarbamate (287 mg) and the compound (356 mg) of Starting Material Synthetic Example 52.
$^1$H-NMR(400 MHz, DMSO-$d_6$)δ(ppm): 1.68(2H, d, J=13.2 Hz), 1.92-1.93(2H, m), 3.24-3.25(2H, m), 4.09(2H, d, J=13.2 Hz), 5.32(1H, s), 7.00-8.97(8H, m), 9.00(1H, s), 12.44 (1H, s). MS(ESI)m/z:338[M+H]⁺.

Example 14

By a similar operation as in Example 1, 4-(5-chloro-2-thienyl)-4-hydroxy-1-piperidinecarboxylic acid (1H-indazol-3-yl)amide (93 mg, yield 25%) was obtained from ethyl 1H-indazol-3-ylcarbamate (205 mg) and the compound (259 mg) of Starting Material Synthetic Example 53.
$^1$H-NMR(400 MHz, DMSO-$d_6$)δ(ppm): 1.78(2H, d, J=13.2 Hz), 1.88-1.89(2H, m), 3.22-3.33(2H, m), 4.02(2H, d, J=13.2 Hz), 5.80(1H, s), 6.86-7.61(6H, m), 8.98(1H, s), 12.45 (1H, s). MS(ESI)m/z:377[M+H]⁺.

Example 15

By a similar operation as in Example 1, 4-(3-chloro-4-fluorophenyl)-4-hydroxy-1-piperidinecarboxylic acid (1H-indazol-3-yl)amide (148 mg, yield 20%) was obtained from ethyl 1H-indazol-3-ylcarbamate (385 mg) and the compound (516 mg) of Starting Material Synthetic Example 54.
$^1$H-NMR(400 MHz, DMSO-$d_6$)δ(ppm): 1.62(2H, d, J=12.8 Hz), 1.92-1.93(2H, m), 3.23-3.33(2H, m), 4.09(2H, d, J=12.8 Hz), 5.32(1H, s), 7.00-7.70(7H, m), 8.96(1H, s), 12.45 (1H, s). MS(ESI)m/z:389[M+H]⁺.

Example 16

By a similar operation as in Example 1, 4-hydroxy-4-(3,4,5-trifluorophenyl)-1-piperidinecarboxylic acid (1H-indazol-3-yl)amide (184 mg, yield 34%) was obtained from ethyl 1H-indazol-3-ylcarbamate (290 mg) and the compound (398 mg) of Starting Material Synthetic Example 55.
$^1$H-NMR(400 MHz, DMSO-$d_6$)δ(ppm): 1.60(2H, d, J=13.2 Hz), 1.91-1.93(2H, m), 3.18-3.24(2H, m), 4.10(2H, d, J=13.2 Hz), 5.48(1H, s), 6.99-7.65(6H, m), 8.96(1H, s), 12.46 (1H, s). MS(ESI)m/z:391[M+H]⁺.

Example 17

By a similar operation as in Example 1, 4-(4-chloro-3-fluorophenyl)-4-hydroxy-1-piperidinecarboxylic acid (1H-indazol-3-yl)amide (490 mg, yield 86%) was obtained from ethyl 1H-indazol-3-ylcarbamate (300 mg) and the compound (402 mg) of Starting Material Synthetic Example 56.
$^1$H-NMR(400 MHz, DMSO-$d_6$)δ(ppm): 1.62(2H, d, J=12.8 Hz), 1.92-1.93(2H, m), 3.21-3.23(2H, m), 4.08(2H, d, J=12.8 Hz), 5.35(1H, s), 7.01-7.64(7H, m), 8.96(1H, s), 12.44 (1H, s). MS(ESI)m/z:389[M+H]⁺.

Example 18

By a similar operation as in Example 12, 4-[4-fluoro-2-(trifluoromethyl)phenyl]-4-hydroxy-1-piperidinecarboxylic acid (1H-indazol-3-yl)amide (137 mg, yield 46%) was obtained from ethyl 1H-indazol-3-ylcarbamate (210 mg) and the compound (120 mg) of Starting Material Synthetic Example 57.
$^1$H-NMR(400 MHz, DMSO-$d_6$)δ(ppm): 1.79(2H, d, J=12.8 Hz), 2.02-2.07(2H, m), 3.28-3.29(2H, m), 4.09(2H, d, J=12.8 Hz), 5.66(1H, s), 7.00-7.83(7H, m), 8.94(1H, s), 12.44 (1H, s). MS(ESI)m/z:423[M+H]⁺.

Example 19

By a similar operation as in Example 1, 4-(5-bromo-3-chloro-2-fluorophenyl)-4-hydroxy-1-piperidinecarboxylic acid (1H-indazol-3-yl)amide (100 mg, yield 10%) was obtained from ethyl 1H-indazol-3-ylcarbamate (300 mg) and the compound (400 mg) of Starting Material Synthetic Example 58.
$^1$H-NMR(400 MHz, DMSO-$d_6$)δ(ppm): 1.61(2H, d, J=13.2 Hz), 2.06-2.18(1H, s), 3.16-3.27(2H, m), 4.09(2H, d, J=13.2 Hz), 5.67(1H, s), 6.99-7.81(6H, m), 9.00(1H, s), 12.43 (1H, s). MS(ESI)m/z:468[M+H]$^+$.

Example 20

By a similar operation as in Example 1, 4-(3-chloro-2-fluorophenyl)-4-hydroxy-1-piperidinecarboxylic acid (1H-indazol-3-yl)amide (635 mg, yield 45%) was obtained from ethyl 1H-indazol-3-ylcarbamate (750 mg) and the compound (1.0 g) of Starting Material Synthetic Example 59.
$^1$H-NMR(400 MHz, DMSO-$d_6$)δ(ppm): 1.65(2H, d, J=12.4 Hz), 2.03-2.09(2H, m), 3.24-3.33(2H, m), 4.09(2H, d, J=12.4 Hz), 5.51(1H, s).7.00-7.68(7H, m), 8.99(1H, s), 12.43 (1H, s). MS(ESI)m/z:489[M+H]$^+$.

Example 21

By a similar operation as in Example 1, 4-(3,4-dichlorophenyl)-4-hydroxy-1-piperidinecarboxylic acid (1H-indazol-3-yl)amide (703 mg, yield 36%) was obtained from ethyl 1H-indazol-3-ylcarbamate (840 mg) and the compound (1.2 g) of Starting Material Synthetic Example 60.
$^1$H-NMR(400 MHz, DMSO-$d_6$)δ(ppm): 1.63(2H, d, J=13.2 Hz), 1.90-1.96(2H, m), 3.20-3.26(2H, m), 4.09(2H, d, J=13.2 Hz), 5.34(1H, s), 6.99-7.74(7H, m), 8.93(1H, s), 12.42 (1H, s). MS(ESI)m/z:405[M+H]$^+$.

Example 22

By a similar operation as in Example 1, 4-(3-chloro-5-fluorophenyl)-4-hydroxy-1-piperidinecarboxylic acid (1H-indazol-3-yl)amide (836 mg, yield 46%) was obtained from ethyl 1H-indazol-3-ylcarbamate (950 mg) and the compound (1.27 g) of Starting Material Synthetic Example 61.
$^1$H-NMR(400 MHz, DMSO-$d_6$)δ(ppm): 1.62(2H, d, J=13.2 Hz), 1.91-1.94(2H, m), 3.20-3.26(2H, m), 4.10(2H, d, J=13.2 Hz), 5.38(1H, s), 6.99-7.65(7H, m), 8.93(1H, s), 12.42 (1H, s). MS(ESI)m/z:389[M+H]$^+$.

Example 23

By a similar operation as in Example 1, 4-(4-chloro-3-methylphenyl)-4-hydroxy-1-piperidinecarboxylic acid (1H-indazol-3-yl)amide (912 mg, yield 55%) was obtained from ethyl 1H-indazol-3-ylcarbamate (888 mg) and the compound (1.36 g) of Starting Material Synthetic Example 62.
$^1$H-NMR(400 MHz, DMSO-$d_6$)δ(ppm): 1.61(2H, d, J=12.8 Hz), 1.86-1.89(2H, m), 2.31(3H, s), 3.21-3.24(2H, m), 4.07(2H, d, J=12.8 Hz), 5.19(1H, s), 6.99-7.64(7H, m), 8.93(1H, s), 12.42(1H, s). MS(ESI) m/z:385[M+H]$^+$.

Example 24

By a similar operation as in Example 1, 4-(3-chlorophenyl)-4-hydroxy-1-piperidinecarboxylic acid (1H-indazol-3-yl)amide (130 mg, yield 64%) was obtained from ethyl 1H-indazol-3-ylcarbamate (114 mg) and the compound (130 mg) of Starting Material Synthetic Example 63.
$^1$H-NMR(400 MHz, DMSO-$d_6$)δ(ppm): 1.63(2H, d, J=12.8 Hz), 1.92-1.96(2H, m), 3.22-3.23(2H, m), 4.09(2H, d, J=12.8 Hz), 5.25(1H, s), 6.99-7.64(8H, m), 8.93(1H, s), 12.42 (1H, s). MS(ESI)m/z:371[M+H]$^+$.

Example 25

By a similar operation as in Example 1, 4-hydroxy-4-(2-naphthyl)-1-piperidinecarboxylic acid (1H-indazol-3-yl)amide (618 mg, yield 40%) was obtained from ethyl 1H-indazol-3-ylcarbamate (821 mg) and the compound (1.0 g) of Starting Material Synthetic Example 64.
$^1$H-NMR(400 MHz, DMSO-$d_6$)δ(ppm): 1.75(2H, d, J=12.9 Hz), 2.03-2.08(2H, m), 3.33-3.36(2H, m), 4.13(2H, d, J=12.9 Hz), 7.01-8.01(11H, m), 8.97(1H, s), 12.40(1H, s). MS(ESI)m/z:387[M+H]$^+$.

Example 26

By a similar operation as in Example 12, 4-(2-chloropyridin-4-yl)-4-hydroxy-1-piperidinecarboxylic acid (1H-indazol-3-yl)amide (737 mg, yield 66%) was obtained from ethyl 1H-indazol-3-ylcarbamate (630 mg) and the compound (717 mg) of Starting Material Synthetic Example 65.
$^1$H-NMR(400 MHz, DMSO-$d_6$)δ(ppm): 1.62(2H, d, J=12.4 Hz), 1.92-1.95(2H, m), 3.23-3.26(2H, m), 4.12(2H, d, J=12.4 Hz), 5.51(1H, s), 7.00-7.65(6H, m), 8.36-8.37(1H, m), 8.95(1H, s), 12.47(1H, s). MS(ESI)m/z:372[M+H]$^+$.

Example 27

By a similar operation as in Example 12, 4-(1,3-benzodioxol-5-yl)-4-hydroxy-1-piperidinecarboxylic acid (1H-indazol-3-yl)amide (936 mg, yield 65%) was obtained from ethyl 1H-indazol-3-ylcarbamate (714 mg) and the compound (1.0 g) of Starting Material Synthetic Example 66.
$^1$H-NMR(400 MHz, DMSO-$d_6$)δ(ppm): 1.62(2H, d, J=12.8 Hz), 1.87-1.91(2H, m), 3.21-3.27(2H, m), 4.05(2H, d, J=12.8 Hz), 5.03(1H, s), 5.98(2H, s), 6.84-7.63(7H, m), 8.91 (1H, s), 12.41(1H, s). MS(ESI)m/z:381[M+H]$^+$.

Example 28

By a similar operation as in Example 12, 4-hydroxy-4-(3-methylphenyl)-1-piperidinecarboxylic acid (1H-indazol-3-yl)amide (992 mg, yield 64%) was obtained from ethyl 1H-indazol-3-ylcarbamate (904 mg) and the compound (1.0 g) of Starting Material Synthetic Example 67.
$^1$H-NMR(400 MHz, DMSO-$d_6$)δ(ppm): 1.63(2H, d, J=12.8 Hz), 1.88-1.9.4(2H, m), 2.32(3H, s), 3.23-3.33(2H, m), 4.06(2H, d, J=12.8 Hz), 5.02(1H, s), 7.00-7.64 (8H, m), 8.92(1H, s), 12.42(1H, s). MS(ESI)m/z:351[M+H]$^+$.

Example 29

By a similar operation as in Example 12, 4-(3-cyanophenyl)-4-hydroxy-1-piperidinecarboxylic acid (1H-indazol-3-yl)amide (607 mg, yield 79%) was obtained from ethyl 1H-indazol-3-ylcarbamate (448 mg) and the compound (484 mg) of Starting Material Synthetic Example 68.
$^1$H-NMR(400 MHz, DMSO-$d_6$)δ(ppm): 1.64(2H, d, J=12.4 Hz), 1.96-1.97(2H, m), 3.23-3.24(2H, m), 4.11(2H, d, J=12.4 Hz), 5.35(1H, s), 7.00-7.95(8H, m), 8.94(1H, s), 12.42 (1H, s). MS(ESI)m/z:362[M+H]$^+$.

Example 30

By a similar operation as in Example 12, 4-hydroxy-4-[3-(methylthio)phenyl]-1-piperidinecarboxylic acid (1H-indazol-3-yl)amide (1.19 g, yield 69%) was obtained from ethyl 1H-indazol-3-ylcarbamate (924 mg) and the compound (1.21 g) of Starting Material Synthetic Example 69.
$^1$H-NMR(400 MHz, DMSO-$d_6$)δ(ppm): 1.63(2H, d, J=12.8 Hz), 1.88-1.96(2H, m), 3.22-3.23(2H, m), 4.08(2H, d, J=12.8 Hz), 5.11(1H, s), 6.99-7.64(8H, m), 8.91(1H, s), 12.40 (1H, s). MS(ESI)m/z:383[M+H]$^+$.

Example 31

By a similar operation as in Example 12, 4-(3-ethylphenyl)-4-hydroxy-1-piperidinecarboxylic acid (1H-indazol-3-yl)amide (1.64 g, yield 76%) was obtained from ethyl 1H-indazol-3-ylcarbamate (1.20 g) and the compound (1.46 g) of Starting Material Synthetic Example 70.
$^1$H-NMR(400 MHz, DMSO-$d_6$)δ(ppm): 1.17-1.21(3H, m), 1.63(2H, d, J=12.8 Hz), 1.91-1.95(2H, m), 3.23-3.25(2H, m), 4.07(2H, d, J=12.8 Hz), 5.03(1H, s), 6.99-7.64(8H, m), 8.93(1H, s), 12.42(1H, s). MS(ESI)m/z:365[M+H]$^+$.

Example 32

By a similar operation as in Example 12, 4-(1-acetyl-2,3-dihydroindol-5-yl)-4-hydroxy-1-piperidinecarboxylic acid (1H-indazol-3-yl)amide (521 mg, yield 69%) was obtained from ethyl 1H-indazol-3-ylcarbamate (377 mg) and the compound (576 mg) of Starting Material Synthetic Example 71.
$^1$H-NMR(400 MHz, DMSO-$d_6$)δ(ppm): 1.63-1.79(4H, m), 3.12-3.14(2H, m), 3.81-3.82(2H, m), 4.19-4.23(2H, m), 4.84(1H, s), 6.98-8.06(7H, m), 8.89(1H, s), 12.40(1H, s). MS(ESI)m/z:420[M+H]$^+$.

Example 33

By a similar operation as in Example 12, 4-(2,5-dichlorophenyl)-4-hydroxy-1-piperidinecarboxylic acid (1H-indazol-3-yl)amide (491 mg, yield 85%) was obtained from ethyl 1H-indazol-3-ylcarbamate (291 mg) and the compound (423 mg) of Starting Material Synthetic Example 72.
$^1$H-NMR(400 MHz, DMSO-$d_6$)δ(ppm): 1.47(2H, d, J=12.8 Hz), 2.65-2.66(2H, m), 3.24-3.25(2H, m), 4.10(2H, d, J=12.8 Hz), 5.54(1H, s), 6.99-7.87(7H, m), 9.02(1H, s), 12.43 (1H, s). MS(ESI)m/z:405[M+H]$^+$.

Example 34

By a similar operation as in Example 12, 4-[3,5-bis(trifluoromethyl)phenyl]-4-hydroxy-1-piperidinecarboxylic acid (1H-indazol-3-yl)amide (304 mg, yield 91%) was obtained from ethyl 1H-indazol-3-ylcarbamate (146 mg) and the compound (247 mg) of Starting Material Synthetic Example 73.
$^1$H-NMR(300 MHz, DMSO-$d_6$)δ(ppm): 1.64-1.68(2H, m), 2.05-2.13(2H, m), 3.22-3.30(2H, m), 4.13-4.17(2H, m), 5.63(1H, s), 7.02-8.20(7H, m), 8.98(1H, s), 12.45(1H, s). MS(ESI)m/z:473[M+H]$^+$.

Example 35

By a similar operation as in Example 12, 4-[2-fluoro-5-(trifluoromethyl)phenyl]-4-hydroxy-1-piperidinecarboxylic acid (1H-indazol-3-yl)amide (227 mg, yield 90%) was obtained from ethyl 1H-indazol-3-ylcarbamate (145 mg) and the compound (204 mg) of Starting Material Synthetic Example 74.
$^1$H-NMR(300 MHz, DMSO-$d_6$)δ(ppm): 1.58-1.62(2H, m), 2.19-2.26(2H, m), 3.23-3.27(2H, m), 4.08-4.12(2H, m), 5.69(1H, s), 7.03-8.03(7H, m), 9.04(1H, s), 12.46(1H, s). MS(ESI)m/z:423[M+H]$^+$.

Example 36

By a similar operation as in Example 12, 4-[2-chloro-5-(trifluoromethyl)phenyl]-4-hydroxy-1-piperidinecarboxylic acid (1H-indazol-3-yl)amide (101 mg, yield 37%) was obtained from ethyl 1H-indazol-3-ylcarbamate (145 mg) and the compound (128 mg) of Starting Material Synthetic Example 75.
$^1$H-NMR(300 MHz, DMSO-$d_6$)δ(ppm): 1.51-1.52(2H, m), 2.72(2H, m), 3.23-3.30(2H, m), 4.12-4.16(2H, m), 5.72 (1H, s), 7.03-8.22(6H, m), 9.07(1H, s), 12.47(1H, s). MS(ESI)m/z:439[M+H]$^+$.

Example 37

By a similar operation as in Example 1, 4-{4-chloro-3-[(dimethylamino)methyl]phenyl}-4-hydroxy-1-piperidinecarboxylic acid (1H-indazol-3-yl)amide (508 mg, yield 56%) was obtained from ethyl 1H-indazol-3-ylcarbamate (422 mg) and the compound (610 mg) of Starting Material Synthetic Example 76.
$^1$H-NMR(400 MHz, DMSO-$d_6$)δ(ppm): 0.97-1.01(6H, m), 1.63(2H, d, J=9.6 Hz), 2.52-2.54(2H, m), 3.22-3.25(2H, m), 3.60(2H, s), 4.07(2H, d, J=9.6 Hz), 5.22(1H, s), 6.99-7.67 (7H, m), 9.00(1H, s), 12.46(1H, s). MS(ESI)m/z:456[M+H]$^+$.

Example 38

4-Cyano-4-phenylpiperidine hydrochloride (Aldrich Co., 217 mg) was dissolved in dimethyl sulfoxide (3 ml) and DBU (0.16 ml) was added thereto. The mixture was stirred at room temperature for 30 min, and ethyl 1H-indazol-3-ylcarbamate (200 mg) and potassium fluoride-alumina (40 wt %, 200 mg) were added to the mixture. By the following operation as in Example 1, 4-cyano-4-phenyl-1-piperidinecarboxylic acid (1H-indazol-3-yl)amide (253 mg, yield 75%) was obtained.
$^1$H-NMR(300 MHz, DMSO-$d_6$)δ(ppm): 1.93-2.07(2H, m), 2.21(2H, d, J=12.9 Hz), 3.11-3.20(2H, m), 4.40(2H, d, J=12.9 Hz), 7.02(1H, m), 7.30-7.65(8H, m), 9.17(1H, s), 12.50(1H, s). MS(ESI)m/z:346[M+H]$^+$.

Example 39

By a similar operation as in Example 1, 4-cyano-4-(4-fluorophenyl)-1-piperidinecarboxylic acid (1H-indazol-3-yl)amide (179 mg, yield 49%) was obtained from ethyl 1H-indazol-3-ylcarbamate (142 mg) and the compound (198 mg) of Starting Material Synthetic Example 29.
$^1$H-NMR(300 MHz, DMSO-$d_6$)δ(ppm): 1.98-2.07(2H, m), 2.20-2.24(2H, m), 3.10-3.18(2H, m), 4.37-4.41(2H, m), 7.00-7.04(1H, m), 7.28-7.34(3H, m), 7.40-7.42(1H, m), 7.63-7.67(3H, m), 9.15(1H, s), 12.49(1H, s). MS(ESI)m/z:364 [M+H]$^+$.

Example 40

By a similar operation as in Example 1, 4-cyano-4-(2-methoxyphenyl)-1-piperidinecarboxylic acid (1H-indazol-3- yl)amide (83 mg, yield 25%) was obtained from ethyl 1H-indazol-3-ylcarbamate (181 mg) and the compound (262 mg) of Starting Material Synthetic Example 30.

$^1$H-NMR(300 MHz, DMSO-d$_6$)δ(ppm): 1.98-2.03(2H, m), 2.36(2H, d, J=13.7 Hz), 3.14-3.22(2H, m), 4.36(2H, d, J=13.7 Hz), 7.00-7.06(2H, m), 7.17(1H, d, J=8.0 Hz), 7.29-7.42(3H, m), 7.62(1H, d, J=8.0 Hz), 9.14(1H, s), 12.49(1H, s). MS(ESI)m/z:376[M+H]$^+$.

Example 41

By a similar operation as in Example 1, 4-cyano-4-[4-(trifluoromethyl)phenyl]-1-piperidinecarboxylic acid (1H-indazol-3-yl)amide (195 mg, yield 43%) was obtained from ethyl 1H-indazol-3-ylcarbamate (225 mg) and the compound (320 mg) of Starting Material Synthetic Example 31.

$^1$H-NMR(300 MHz, DMSO-d$_6$)δ(ppm): 2.05-2.14(2H, m), 2.25(2H, d, J=13.5 Hz), 3.12-3.21(2H, m), 4.42(2H, d, J=13.5 Hz), 7.02(1H, t, J=7.5 Hz), 7.31(1H, t, J=7.5 Hz), 7.41(1H, d, J=8.4 Hz), 7.65(1H, d, J=8.4 Hz), 7.85(4H, m), 9.17(1H, s), 12.49(1H, s). MS(ESI)m/z:414[M+H]$^+$.

Example 42

By a similar operation as in Example 1, 4-cyano-4-[3-(trifluoromethyl)phenyl]-1-piperidinecarboxylic acid (1H-indazol-3-yl)amide (20 mg, yield 6%) was obtained from ethyl 1H-indazol-3-ylcarbamate (180 mg) and the compound (260 mg) of Starting Material Synthetic Example 32.

$^1$H-NMR(300 MHz, DMSO-d$_6$)δ(ppm): 2.11-2.15(2H, m), 2.26-2.30(2H, m), 3.09-3.29(2H, m), 4.40-4.45(2H, m), 7.00-7.04(1H, m), 7.28-7.33(1H, m), 7.41(1H, d, J=8.4 Hz), 7.65(1H, d, J=8.4 Hz), 7.73-7.78(2H, m), 7.92-7.97(2H, m), 9.15(1H, s), 12.49(1H, s). MS(ESI)m/z:414[M+H]$^+$.

Example 43

By a similar operation as in Example 1, 4-cyano-4-(2-fluorophenyl)-1-piperidinecarboxylic acid (1H-indazol-3-yl)amide (0.14 g, yield 44%) was obtained from ethyl 1H-indazol-3-ylcarbamate (180 mg) and the compound (260 mg) of Starting Material Synthetic Example 33.

$^1$H-NMR(300 MHz, DMSO-d$_6$)δ(ppm): 2.04-2.13(2H, m), 2.31(2H, d, J=13.7 Hz), 3.15-3.24(2H, m), 4.39(2H, d, J=13.7 Hz), 7.01-7.02(1H, m), 7.04-7.64(7H, m), 9.17(1H, s), 12.50(1H, s). MS(ESI)m/z:364[M+H]$^+$.

Example 44

By a similar operation as in Example 1, 4-[4-chloro-3-(trifluoromethyl)phenyl]-4-cyano-1-piperidinecarboxylic acid (1H-indazol-3-yl)amide (40 mg, yield 35%) was obtained from ethyl 1H-indazol-3-ylcarbamate (52 mg) and the compound (74 mg) of Starting Material Synthetic Example 34.

$^1$H-NMR(300 MHz, DMSO-d$_6$)δ(ppm): 2.11(2H, t, J=12.5 Hz), 2.28(2H, d, J=13.5 Hz), 3.14(2H, t, J=12.5 Hz), 4.42(2H, d, J=13.5 Hz), 7.02(1H, t, J=7.5 Hz), 7.30(1H, t, J=7.5 Hz), 7.41(1H, d, J=8.3 Hz), 7.65(1H, d, J=8.3 Hz), 7.83-7.87(1H, m), 7.94-7.99(2H, m), 9.15(1H, s), 12.50(1H, s). MS(ESI)m/z:448[M+H]$^+$.

Example 45

By a similar operation as in Example 1, 4-cyano-4-[3-fluoro-5-(trifluoromethyl)phenyl]-1-piperidinecarboxylic acid (1H-indazol-3-yl)amide (110 mg, yield 22%) was obtained from ethyl 1H-indazol-3-ylcarbamate (230 mg) and the compound (400 mg) of Starting Material Synthetic Example 35.

$^1$H-NMR(300 MHz, DMSO-d$_6$)δ(ppm): 2.13(2H, t, J=12.9 Hz), 2.32(2H, d, J=13.8 Hz), 3.14(2H, t, J=13.8 Hz), 4.42(2H, d, J=13.8 Hz), 7.02(1H, t, J=7.5 Hz), 7.30(1H, t, J=7.5 Hz), 7.41(1H, d, J=8.3 Hz), 7.65(1H, d, J=8.3 Hz), 7.76-7.89(3H, m), 9.14(1H, s), 12.48(1H, s). MS(ESI)m/z:432[M+H]$^+$.

Example 46

By a similar operation as in Example 1, 4-(5-bromo-2-thienyl)-4-cyano-1-piperidinecarboxylic acid (1H-indazol-3-yl)amide (161 mg, yield 29%) was obtained from ethyl 1H-indazol-3-ylcarbamate (266 mg) and the compound (250 mg) of Starting Material Synthetic Example 36.

$^1$H-NMR(300 MHz, DMSO-d$_6$)δ(ppm): 1.96-2.04(2H, m), 3.56(2H, d, J=13.8 Hz), 3.11-3.19(2H, m), 4.29(2H, d, J=13.8 Hz), 6.99-7.04(1H, m), 7.16-7.42(4H, m), 7.60-7.63(1H, m), 9.17(1H, s), 12.49(1H, s). MS(ESI)m/z:431[M+H]$^+$.

Example 47

By a similar operation as in Example 1, 4-cyano-4-(3,5-difluorophenyl)-1-piperidinecarboxylic acid (1H-indazol-3-yl)amide (0.24 g, yield 63%) was obtained from ethyl 1H-indazol-3-ylcarbamate (200 mg) and the compound (320 mg) of Starting Material Synthetic Example 37.

$^1$H-NMR(300 MHz, DMSO-d$_6$)δ(ppm): 2.05(2H, t, J=12.9 Hz), 2.27(2H, d, J=13.5 Hz), 3.13(2H, t, J=12.9 Hz), 4.39(2H, d, J=13.5 Hz), 6.99-7.04(1H, m), 7.28-7.42(5H, m), 7.63-7.66(1H, m), 9.14(1H, s), 12.48(1H, s). MS(ESI)m/z: 382[M+H]$^+$.

Example 48

Ethyl 1H-indazol-3-ylcarbamate (192 mg), the compound (314 mg) of Starting Material Synthetic Example 38 and DBU (0.31 ml) were added to dimethyl sulfoxide (3 ml), and the mixture was stirred at 95° C. for 4 hr. The reaction mixture was diluted with methanol (4 ml), and 1N aqueous hydrochloric acid and water were added to the mixture at room temperature. The mixture was stirred for 1 hr and the precipitated solid was collected by filtration. The obtained solid was washed in a suspension state with acetonitrile to give 4-(4-bromo-2-chlorophenyl)-4-cyano-1-piperidinecarboxylic acid (1H-indazol-3-yl)amide (205 mg, yield 48%).

$^1$H-NMR(300 MHz, DMSO-d$_6$)δ(ppm): 2.04(2H, t, J=9.3 Hz), 2.47-2.60(2H, m), 3.19(2H, t, J=9.3 Hz), 4.38-4.43(2H, m), 7.01(1H, t, J=7.5 Hz), 7.30(1H, t, J=7.5 Hz), 7.41(1H, d, J=7.5 Hz), 7.52(1H, d, J=7.5 Hz), 7.61-7.70(2H, m), 7.90(1H, s), 9.18(1H, s), 12.50(1H, s). MS(ESI)m/z:459[M+H]$^+$.

Example 49

By a similar operation as in Example 1, 4-phenyl-1,2,3,6-tetrahydropyridine-1-carboxylic acid (1H-indazol-3-yl)amide (152 mg, yield 66%) was obtained from ethyl 1H-indazol-3-ylcarbamate (148 mg) and 4-phenyl-1,2,3,6-tetrahydropyridine hydrochloride (Tokyo Chemical Industry CO., LTD., 197 mg).

$^1$H-NMR(300 MHz, DMSO-d$_6$)δ(ppm): 2.54-2.57(2H, m), 3.71-3.75(2H, m), 4.19-4.20(2H, m), 6.24(1H, s), 6.99-

7.03(1H, m), 7.28-7.42(5H, m), 7.48-7.50(2H, m), 7.60-7.63 (1H, m), 9.03(1H, s), 12.49(1H, s). MS(ESI)m/z:319[M+ H]⁺.

Example 50

By a similar operation as in Example 1, 4-(4-fluorophenyl)-1,2,3,6-tetrahydropyridine-1-carboxylic acid (1H-indazol-3-yl)amide (256 mg, yield 78%) was obtained from ethyl 1H-indazol-3-ylcarbamate (200 mg) and 4-(4-fluorophenyl)-1,2,3,6-tetrahydropyridine hydrochloride (ACROS CO., 208 mg).
¹H-NMR(300 MHz, DMSO-d₆)δ(ppm): 2.51-2.54(2H, m), 3.70-3.74(2H, m), 4.18-4.19(2H, m), 6.22(1H, s), 6.99-7.03(1H, m), 7.16-7.22(2H, m), 7.27-7.32(1H, m), 7.40-7.42 (1H, m), 7.51-7.56(2H, m), 7.60-7.63(1H, m), 9.03(1H, s), 12.49(1H, s). MS(ESI)m/z:337[M+H]⁺.

Example 51

By a similar operation as in Example 1, 4-(4-chlorophenyl)-1,2,3,6-tetrahydropyridine-1-carboxylic acid (1H-indazol-3-yl)amide (274 mg, yield 76%) was obtained from ethyl 1H-indazol-3-ylcarbamate (209 mg) and 4-(4-chlorophenyl)-1,2,3,6-tetrahydropyridine hydrochloride (ACROS CO., 242 mg).
¹H-NMR(300 MHz, DMSO-d₆)δ(ppm): 2.50-2.54(2H, m), 3.14-3.79(2H, m), 4.13-4.20(2H, m), 6.29(1H, s), 6.98-7.03(1H, m), 7.27-7.32(1H, m), 7.39-7.43(3H, m), 7.51-7.54 (2H, m), 7.60-7.63(1H, m), 9.04(1H, s), 12.49(1H, s). MS(ESI)m/z:353[M+H]⁺.

Example 52

By a similar operation as in Example 1, 4-(2-fluorophenyl)-1,2,3,6-tetrahydropyridine-1-carboxylic acid (1H-indazol-3-yl)amide (100 mg, yield 30%) was obtained from ethyl 1H-indazol-3-ylcarbamate (205 mg) and 4-(2-fluorophenyl)-1,2,3,6-tetrahydropyridine (synthesized according to the method described in J. Med. Chem., 35, 22, 1992, 4020-4026., 266 mg).
¹H-NMR(300 MHz, DMSO-d₆)δ(ppm): 2.54-2.55(2H, m), 3.70-3.73(2H, m), 4.19-4.20(2H, m), 6.34(1H, s), 6.99-7.62(8H, m), 9.04(1H, s), 12.49(1H, s). MS(ESI)m/z:337 [M+H]⁺.

Example 53

By a similar operation as in Example 1, 4-(3-chloro-4-fluorophenyl)-1,2,3,6-tetrahydropyridine-1-carboxylic acid (1H-indazol-3-yl)amide (81 mg, yield 15%) was obtained from ethyl 1H-indazol-3-ylcarbamate (205 mg) and the compound (254 mg) of Starting Material Synthetic Example 39.
¹H-NMR(300 MHz, DMSO-d₆)δ(ppm): 2.51-2.54(2H, m), 3.69-3.72(2H, m), 4.19-4.20(2H, m), 6.31(1H, s), 6.99-7.70(7H, m), 9.04(1H, s), 12.49(1H, s). MS(ESI)m/z:371 [M+H]⁺.

Example 54

By a similar operation as in Example 1, 4-(4-methoxyphenyl)-1,2,3,6-tetrahydropyridine-1-carboxylic acid (1H-indazol-3-yl)amide (71 mg, yield 20%) was obtained from ethyl 1H-indazol-3-ylcarbamate (205 mg) and 4-(4-methoxyphenyl)-1,2,3,6-tetrahydropyridine (synthesized according to the method described in J. Med. Chem., 35, 22, 1992, 4020-4026., 266 mg).
¹H-NMR(300 MHz, DMSO-d₆)δ(ppm): 2.53-2.54(2H, m), 3.70-3.75(2H, m), 4.10-4.20(8H, m), 6.14(1H, s), 6.99-7.75(8H, m), 9.00(1H, s), 12.46(1H, s). MS(ESI)m/z:349 [M+H]⁺.

Example 55

By a similar operation as in Example 1, 4-(3-fluorophenyl)-1,2,3,6-tetrahydropyridine-1-carboxylic acid (1H-indazol-3-yl)amide (8 mg, yield 3%) was obtained from ethyl 1H-indazol-3-ylcarbamate (160 mg) and the compound (238 mg) of Starting Material Synthetic Example 85.
¹H-NMR(300 MHz, DMSO-d₆)δ(ppm): 2.52-2.54(2H, m), 3.70-3.74(2H, m), 4.19-4.20(2H, m), 6.32(1H, s), 6.92-7.59(8H, m), 9.03(1H, s), 12.42(1H, s). MS(ESI)m/z:337 [M+H]⁺.

Example 56

By a similar operation as in Example 1, 4-(2,3-difluorophenyl)-1,2,3,6-tetrahydropyridine-1-carboxylic acid (1H-indazol-3-yl)amide (68 mg, yield 19%) was obtained from ethyl 1H-indazol-3-ylcarbamate (205 mg) and the compound (261 mg) of Starting Material Synthetic Example 40.
¹H-NMR(300 MHz, DMSO-d₆)δ(ppm): 2.50-2.53(2H, m), 3.70-3.73(2H, m), 4.20-4.21(2H, m), 6.13(1H, s), 7.00-7.63(7H, m), 9.05(1H, s), 12.49(1H, s). MS(ESI)m/z:355 [M+H]⁺.

Example 57

By a similar operation as in Example 1, 4-(2,4-fluorophenyl)-1,2,3,6-tetrahydropyridine-1-carboxylic acid (1H-indazol-3-yl)amide (7 mg, yield 2%) was obtained from ethyl 1H-indazol-3-ylcarbamate (205 mg) and the compound (224 mg) of Starting Material Synthetic Example 41.
¹H-NMR(300 MHz, DMSO-d₆)δ(ppm): 3.66-3.69(2H, m), 4.15-4.16(2H, m), 6.01(1H, s), 6.96-7.61(7H, m), 9.01 (1H, s), 12.47(1H, s). MS(ESI)m/z:355[M+H]⁺.

Example 58

By a similar operation as in Example 1, 4-(5-chloro-2-thienyl)-1,2,3,6-tetrahydropyridine-1-carboxylic acid (1H-indazol-3-yl)amide (14 mg, yield 3%) was obtained from ethyl 1H-indazol-3-ylcarbamate (300 mg) and the compound (526 mg) of Starting Material Synthetic Example 42.
¹H-NMR(400 MHz, DMSO-d₆)δ(ppm): 3.68-3.70(2H, m), 4.14-4.15(2H, m), 6.11(1H, s), 6.98-7.60(6H, m), 9.06 (1H, s), 12.49(1H, s). MS(ESI)m/z:359[M+H]⁺.

Example 59

By a similar operation as in Example 1, 4-(3-methyl-2-thienyl)-1,2,3,6-tetrahydropyridine-1-carboxylic acid (1H-indazol-3-yl)amide (221 mg, yield 45%) was obtained from ethyl 1H-indazol-3-ylcarbamate (300 mg) and the compound (378 mg) of Starting Material Synthetic Example 86.
¹H-NMR(400 MHz, DMSO-d₆)δ(ppm): 2.24(3H, s), 3.66-3.70(2H, m), 4.16-4.17(2H, m), 5.91(1H, s), 6.87-7.61(6H, m), 9.00(1H, s), 12.46(1H, s). MS(ESI)m/z:339[M+H]⁺.

Example 60

By a similar operation as in Example 1, 4-(2-thienyl)-1,2,3,6-tetrahydropyridine-1-carboxylic acid (1H-indazol-3-yl) amide (89 mg, yield 14%) was obtained from ethyl 1H-indazol-3-ylcarbamate (400 mg) and the compound (485 mg) of Starting Material Synthetic Example 87.

$^1$H-NMR(400 MHz, DMSO-d$_6$)δ(ppm): 2.53-2.54(2H, m), 3.67-3.70(2H, m), 4.14-4.15(2H, m), 6.14(1H, s), 6.96-7.59(7H, m), 9.02(1H, s), 12.46(1H, s). MS(ESI)m/z:325 [M+H]$^+$.

Example 61

By a similar operation as in Example 1, 4-[3-(trifluoromethyl)phenyl]-1,2,3,6-tetrahydropyridine-1-carboxylic acid (1H-indazol-3-yl)amide (22 mg, yield 6%) was obtained from ethyl 1H-indazol-3-ylcarbamate (300 mg) and the compound (416 mg) of Starting Material Synthetic Example 88.

$^1$H-NMR(300 MHz, DMSO-d$_6$)δ(ppm): 2.53-2.66(2H, m), 3.72-3.76(2H, m), 4.22-4.23(2H, m), 6.41(1H, s), 7.01-7.04(1H, m), 7.30-7.33(1H, m), 7.40-7.43(1H, m), 7.61-7.63 (3H, m), 7.75-7.82(2H, m), 9.05(1H, s), 12.49(1H, s). MS(ESI)m/z:387[M+H]$^+$.

Example 62

By a similar operation as in Example 1, 4-(3,4-dimethoxyphenyl)-1,2,3,6-tetrahydropyridine-1-carboxylic acid (1H-indazol-3-yl)amide (63 mg, yield 21%) was obtained from ethyl 1H-indazol-3-ylcarbamate (160 mg) and 4-hydroxy-4-(3,4-dimethoxyphenyl)piperidine (synthesized according to the method described in J. Med. Chem., 28, 3, 1985, 311-317., 238 mg).

$^1$H-NMR(400 MHz, DMSO-d$_6$)δ(ppm): 2.50-2.52(2H, m), 3.67-3.72(2H, m), 4.15-4.17(8H, m), 6.16(1H, s), 6.96-7.59(7H, m), 9.00(1H, s), 12.46(1H, s). MS(ESI)m/z:379 [M+H]$^+$.

Example 63

By a similar operation as in Example 1, 4-[3-(dimethylamino)phenyl]-1,2,3,6-tetrahydropyridine-1-carboxylic acid (1H-indazol-3-yl)amide (37 mg, yield 20%) was obtained from ethyl 1H-indazol-3-ylcarbamate (198 mg) and the compound (118 mg) of Starting Material Synthetic Example 43.

$^1$H-NMR(300 MHz, DMSO-d$_6$)δ(ppm): 2.52-2.56(2H, m), 2.93(6H, s), 3.71-3.74(2H, m), 4.19-4.20(2H, m), 6.18 (1H, s), 6.65-6.69(1H, m), 6.76-6.78(2H, m), 7.02-7.05(1H, m), 7.15-7.17(1H, m), 7.31-7.34(1H, m), 7.41-7.44(1H, m), 7.62-7.64(1H, m), 9.01(1H, s), 12.48(1H, s). MS(ESI)m/z: 362[M+H]$^+$.

Example 64

By a similar operation as in Example 1, 1,3,4,9-tetrahydro-β-carboline-2-carboxylic acid (1H-indazol-3-yl)amide (3.16 g, yield 76%) was obtained from ethyl 1H-indazol-3-ylcarbamate (2.57 g) and 1,2,3,4-tetrahydro-β-carboline (Aldrich Co., 2.16 g).

$^1$H-NMR(300 MHz, DMSO-d$_6$)δ(ppm): 2.76-2.84(2H, m), 3.84-3.91(2H, m), 4.73(2H, s), 6.94-7.09(3H, m), 7.25-7.34(2H, m), 7.38-7.46(2H, m), 7.56-7.61(1H, m), 9.21(1H, s), 10.91(1H, s), 12.51(1H, s). MS(ESI)m/z:332[M+H]$^+$.

Example 65

By a similar operation as in Example 1, 9-methyl-1,3,4,9-tetrahydro-β-carboline-2-carboxylic acid (1H-indazol-3-yl) amide (63 mg, yield 15%) was obtained from ethyl 1H-indazol-3-ylcarbamate (250 mg) and 9-methyl-2,3,4,9-tetrahydro-1H-β-carboline (synthesized according to the method described in J. Med. Chem., 45, 11, 2002, 2197-2206, 250 mg).

$^1$H-NMR(300 MHz, DMSO-d$_6$)δ(ppm): 2.80(2H, s), 3.68 (3H, s), 4.03(2H, m), 4.81(2H, s), 7.01-7.05(2H, m), 7.13(1H, t, J=6.9 Hz), 7.30(1H, t, J=6.9 Hz), 7.40-7.47(3H, m), 7.62 (1H, d, J=8.1 Hz), 9.19(1H, s), 12.50(1H, s). MS(ESI)m/z: 346[M+H]$^+$.

Example 66

By a similar operation as in Example 38, 9-(2-methoxyethyl)-1,3,4,9-tetrahydro-β-carboline-2-carboxylic acid (1H-indazol-3-yl)amide (322 mg, yield 68%) was obtained from ethyl 1H-indazol-3-ylcarbamate (250 mg) and the compound (357 mg) of Starting Material Synthetic Example 1.

$^1$H-NMR(300 MHz, DMSO-d$_6$)δ(ppm): 2.80(2H, s), 3.20 (3H, s), 3.57-3.64(2H, m), 3.86(2H, t, J=5.4 Hz), 4.27(2H, t, J=5.4 Hz), 4.81(2H, s), 7.00-7.11(3H, m), 7.30-7.47(4H, m), 7.62(1H, d, J=8.1 Hz), 9.18(1H, s), 12.50(1H, s). MS(ESI)m/ z:390[M+H]$^+$.

Example 67

By a similar operation as in Example 38, 9-(2-morpholin-4-ylethyl)-1,3,4,9-tetrahydro-β-carboline-2-carboxylic acid (1H-indazol-3-yl)amide (146 mg, yield 37%) was obtained from ethyl 1H-indazol-3-ylcarbamate (182 mg) and the compound (350 mg) of Starting Material Synthetic Example 2.

$^1$H-NMR(300 MHz, DMSO-d$_6$)δ(ppm): 2.41(4H, m), 2.51 (2H, m), 2.80(2H, s), 3.53(4H, m), 3.86(2H, t, J=6.0 Hz), 4.20(2H, t, J=6.0 Hz), 4.85(2H, s), 6.98-7.12(3H, m), 7.30-7.47(4H, m), 7.60(1H, d, J=8.4 Hz), 9.22(1H, s), 12.50(1H, s). MS(ESI)m/z:445[M+H]$^+$.

Example 68

By a similar operation as in Example 1, 1,3,4,5-tetrahydro-2H-pyrido[4,3-b]indole-2-carboxylic acid (1H-indazol-3-yl) amide (178 mg, yield 57%) was obtained from ethyl 1H-indazol-3-ylcarbamate (195 mg) and 2,3,4,5-tetrahydro-1H-pyrido[4,3-b]indole (synthesized according to the method described in J. Med. Chem., 30, 10, 1987, 1818-1823., 180 mg).

$^1$H-NMR(300 MHz, DMSO-d$_6$)δ(ppm): 2.86-2.92(2H, m), 3.86-3.93(2H, m), 4.73(2H, s), 6.93-7.09(3H, m), 7.26-7.44(3H, m), 7.41(1H, d, J=8.1 Hz), 7.62(1H, d, J=8.1 Hz), 9.14(1H, s), 10.92(1H, s). MS(ESI)m/z:332[M+H]$^+$.

Example 69

By a similar operation as in Example 1, 6-(trifluoromethyl)-1,3,4,9-tetrahydro-β-carboline-2-carboxylic acid (1H-indazol-3-yl)amide (184 mg, yield 47%) was obtained from ethyl 1H-indazol-3-ylcarbamate (200 mg) and 6-(trifluoromethyl)-2,3,4,9-tetrahydro-1H-β-carboline (synthesized according to the method described in Bioorg. Med. Chem. Lett., 13, 14, 2003, 2419-2422., 246 mg).

$^1$H-NMR(400 MHz, DMSO-d$_6$)δ(ppm): 2.86(2H, t, J=5.5 Hz), 3.89(2H, t, J=5.5 Hz), 4.77(2H, s), 6.96(6H, m), 7.83 (1H, s), 9.25(1H, s), 11.43(1H, s), 12.51(1H, s). MS(ESI)m/ z:400[M+H]$^+$.

Example 70

By a similar operation as in Example 1, 6-fluoro-1,3,4,9-tetrahydro-β-carboline-2-carboxylic acid (1H-indazol-3-yl)

amide (186 mg, yield 48%) was obtained from ethyl 1H-indazol-3-ylcarbamate (230 mg) and the compound (224 mg) of Starting Material Synthetic Example 4.

$^1$H-NMR(400 MHz, DMSO-d$_6$)δ(ppm): 2.77(2H, t, J=5.5 Hz), 3.87(2H, t, J=5.5 Hz), 4.72(2H, s), 6.83-7.61(7H, m), 9.21(1H, s), 11.01(1H, s), 12.50(1H, s). MS(ESI)m/z:350 [M+H]$^+$.

Example 71

By a similar operation as in Example 1, 7-fluoro-1,3,4,9-tetrahydro-β-carboline-2-carboxylic acid (1H-indazol-3-yl)amide (205 mg, yield 52%) was obtained from ethyl 1H-indazol-3-ylcarbamate (230 mg) and the compound (224 mg) of Starting Material Synthetic Example 3.

$^1$H-NMR(400 MHz, DMSO-d$_6$)δ(ppm): 2.78(2H, t, J=5.5 Hz), 3.86(2H, t, J=5.5 Hz), 4.71(2H, s), 6.80-7.61(7H, m), 9.20(1H, s), 11.01(1H, s), 12.50(1H, s). MS(ESI)m/z:350 [M+H]$^+$.

Example 72

By a similar operation as in Example 1, 6-chloro-1,3,4,9-tetrahydro-β-carboline-2-carboxylic acid (1H-indazol-3-yl)amide (186 mg, yield 45%) was obtained from ethyl 1H-indazol-3-ylcarbamate (230 mg) and the compound (243 mg) of Starting Material Synthetic Example 5.

$^1$H-NMR(400 MHz, DMSO-d$_6$)δ(ppm): 2.78(2H, t, J=5.5 Hz), 3.87(2H, t, J=5.5 Hz), 4.73(2H, s), 6.97-7.03(1H, m), 7.05(1H, dd, J=8.6 Hz, 2.4 Hz), 7.26-7.31(1H, m), 7.33(1H, d, J=8.6 Hz), 7.39-7.43(1H, m), 7.48.(1H, d, J=2.4 Hz), 7.58 (1H, m), 9.22(1H, s), 11.13(1H, s), 12.50(1H, s). MS(ESI)m/z:366[M+H]$^+$.

Example 73

By a similar operation as in Example 1, 6-methoxy-1,3,4,9-tetrahydro-β-carboline-2-carboxylic acid (1H-indazol-3-yl)amide (165 mg, yield 41%) was obtained from ethyl 1H-indazol-3-ylcarbamate (230 mg) and 6-methoxy-2,3,4,9-tetrahydro-1H-β-carboline (Aldrich Co., 238 mg).

$^1$H-NMR(400 MHz, DMSO-d$_6$)δ(ppm): 2.77(2H, t, J=5.5 Hz), 3.76(3H, s), 3.86(2H, t, J=5.5 Hz), 4.70(2H, s), 6.69(1H, dd, J=8.6 Hz, 2.4 Hz), 6.93(1H, d, J=2.4 Hz), 7.00(1H, m), 7.20(1H, d, J=8.6 Hz), 7.26-7.61(3H, m), 9.19(1H, s), 10.72 (1H, s), 12.50(1H, s). MS(ESI)m/z:362[M+H]$^+$.

Example 74

By a similar operation as in Example 1, 6-hydroxy-1,3,4,9-tetrahydro-β-carboline-2-carboxylic acid (1H-indazol-3-yl)amide (112 mg, yield 29%) was obtained from ethyl 1H-indazol-3-ylcarbamate (230 mg) and the compound (222 mg) of Starting Material Synthetic Example 6.

$^1$H-NMR(400 MHz, DMSO-d$_6$)δ(ppm): 2.68-2.74(2H, m), 3.81-3.88(2H, m), 4.67(2H, s), 6.55(1H, dd, J=8.6 Hz, 2.4 Hz), 6.73(1H, d, J=2.4 Hz), 6.96-7.03(1H, m), 7.09(1H, d, J=8.6 Hz), 7.26-7.60(3H, m), 8.58(1H, s), 9.17(1H, s), 10.55 (1H, s), 12.49(1H, s). MS(ESI)m/z:348[M+H]$^+$.

Example 75

By a similar operation as in Example 1, 7-chloro-1,3,4,9-tetrahydro-β-carboline-2-carboxylic acid (1H-indazol-3-yl)amide (141 mg, yield 34%) was obtained from ethyl 1H-indazol-3-ylcarbamate (230 mg) and the compound (243 mg) of Starting Material Synthetic Example 7.

$^1$H-NMR(400 MHz, DMSO-d$_6$)δ(ppm): 2.79(2H, t, J=5.5 Hz), 3.87(2H, t, J=5.5 Hz), 4.72(2H, s), 6.96-7.60(7H, m), 9.22(1H, s), 11.10(1H, s), 12.51(1H, s). MS(ESI)m/z:366 [M+H]$^+$.

Example 76

By a similar operation as in Example 1, 7-(trifluoromethyl)-1,3,4,9-tetrahydro-β-carboline-2-carboxylic acid (1H-indazol-3-yl)amide (130 mg, yield 46%) was obtained from ethyl 1H-indazol-3-ylcarbamate (146 mg) and the compound (180 mg) of Starting Material Synthetic Example 8.

$^1$H-NMR(400 MHz, DMSO-d$_6$)δ(ppm): 2.84(2H, t, J=5.5 Hz), 3.90(2H, t, J=5.5 Hz), 4.79(2H, s), 6.97-7.68(7H, m), 9.25(1H, s), 11.42(1H, s), 12.51(1H, s). MS(ESI)m/z:400 [M+H]$^+$.

Example 77

By a similar operation as in Example 1, 5-fluoro-1,3,4,9-tetrahydro-β-carboline-2-carboxylic acid (1H-indazol-3-yl)amide (380 mg, yield 58%) was obtained from ethyl 1H-indazol-3-ylcarbamate (383 mg) and the compound (373 mg) of Starting Material Synthetic Example 9.

$^1$H-NMR(400 MHz, DMSO-d$_6$)δ(ppm): 2.94(2H, t, J=5.5 Hz), 3.87(2H, t, J=5.5 Hz), 4.73(2H, s), 6.68-7.61(7H, m), 9.22(1H, s), 11.23(1H, s), 12.51(1H, s). MS(ESI)m/z:350 [M+H]$^+$.

Example 78

By a similar operation as in Example 12, 5-chloro-1,3,4,9-tetrahydro-β-carboline-2-carboxylic acid (1H-indazol-3-yl)amide (140 mg, yield 35%) was obtained from ethyl 1H-indazol-3-ylcarbamate (223 mg) and the compound (236 mg) of Starting Material Synthetic Example 10.

$^1$H-NMR(400 MHz, DMSO-d$_6$)δ(ppm): 3.09(2H, t, J=5.5 Hz), 3.87(2H, t, J=5.5 Hz), 4.73(2H, s), 6.95-7.62(7H, m), 9.19(1H, s), 11.26(1H, s), 12.48(1H, s). MS(ESI)m/z:366 [M+H]$^+$.

Example 79

By a similar operation as in Example 12, 8-methyl-1,3,4,9-tetrahydro-β-carboline-2-carboxylic acid (1H-indazol-3-yl)amide (223 mg, yield 53%) was obtained from ethyl 1H-indazol-3-ylcarbamate (250 mg) and the compound (238 mg) of Starting Material Synthetic Example 11.

$^1$H-NMR(400 MHz, DMSO-d$_6$)δ(ppm): 2.43(3H, s), 2.79 (2H, t, J=5.5 Hz), 3.88(2H, t, J=5.5 Hz), 4.74(2H, s), 6.82-7.61(7H, m), 9.18(1H, s), 10.78(1H, s), 12.47(1H, s). MS(ESI)m/z:346[M+H]$^+$.

Example 80

By a similar operation as in Example 12, 3,4-dihydro[1]benzothieno[2,3-c]pyridine-2-carboxylic acid (1H-indazol-3-yl)amide (88 mg, yield 35%) was obtained from ethyl 1H-indazol-3-ylcarbamate (148 mg) and 1,2,3,4-tetrahydrobenzo[4,5]thieno[2,3-c]pyridine (synthesized according to the method described in J. Heterocycl. Chem., 16, 1979, 1321-1324, 150 mg).

$^1$H-NMR(300 MHz, DMSO-d$_6$):δ=2.92(2H, t, J=5.4 Hz), 3.94(2H, t, J=5.4 Hz), 4.85(2H, s), 7.00(1H, t, J=7.5 Hz), 7.44-7.30(4H, m), 7.59(1H, d, J=8.1 Hz), 7.73(1H, d, J=7.5 Hz), 7.96(1H, d, J=8.1 Hz), 9.25(1H, s), 12.5(1H, s). MS(ESI)m/z:349[M+H]$^+$.

Example 81

By a similar operation as in Example 12, 6-methyl-1,3,4,9-tetrahydro-β-carboline-2-carboxylic acid (1H-indazol-3-yl)amide (304 mg, yield 72%) was obtained from ethyl 1H-indazol-3-ylcarbamate (250 mg) and the compound (250 mg) of Starting Material Synthetic Example 12.

$^1$H-NMR(400 MHz, DMSO-$d_6$)δ(ppm): 2.37(3H, s), 2.77 (2H, t, J=5.5 Hz), 3.86(2H, t, J=5.5 Hz), 4.71(2H, s), 6.87-7.61(7H, m), 9.14(1H, s), 10.70(1H, s), 12.45(1H, s). MS(ESI)m/z:346[M+H]$^+$.

Example 82

By a similar operation as in Example 12, 7-chloro-6-fluoro-1,3,4,9-tetrahydro-β-carboline-2-carboxylic acid (1H-indazol-3-yl)amide (312 mg, yield 67%) was obtained from ethyl 1H-indazol-3-ylcarbamate (250 mg) and the compound (287 mg) of Starting Material Synthetic Example 13.

$^1$H-NMR(400 MHz, DMSO-$d_6$)δ(ppm): 2.74-2.79(2H, m), 3.84-3.89(2H, m), 4.72(2H, s), 6.96-7.60(6H, m), 9.20 (1H, s), 11.14(1H, s), 12.48(1H, s). MS(ESI)m/z:384[M+H]$^+$.

Example. 83

By a similar operation as in Example 12, 7-chloro-6-(trifluoromethyl)-1,3,4,9-tetrahydro-β-carboline-2-carboxylic acid (1H-indazol-3-yl)amide (470 mg, yield 74%) was obtained from ethyl 1H-indazol-3-ylcarbamate (300 mg) and the compound (442 mg) of Starting Material Synthetic Example 14.

$^1$H-NMR(400 MHz, DMSO-$d_6$)δ(ppm): 2.85(2H, t, J=5.5 Hz), 3.88(2H, t, J=5.5 Hz), 4.76(2H, s), 6.96-7.61(4H, m), 7.62(1H, s), 7.95(1H, s), 9.23(1H, s), 11.55(1H, s), 12.49(1H, s). MS(ESI)m/z:434[M+H]$^+$.

Example 84

1H-Indazole-3-carbonylazide (synthesized according to the method described in Tetrahedron, 32, 4, 1976, 493-497, 200 mg) was dissolved in dimethylformamide (4 ml), and the mixture was stirred with heating at 100° C. for 30 min. 1-(4-Fluorophenyl)piperazine (Aldrich Co., 211 mg) was dissolved in dimethylformamide (1 ml) and added thereto, and the mixture was stirred with heating at 100° C. for 1 hr. After allowing to cool, water was added to the reaction mixture and the precipitated solid was collected by filtration and dried. The solid was washed in a suspension state with methanol to give 4-(4-fluorophenyl)-1-piperazinecarboxylic acid (1H-indazol-3-yl)amide (64 mg, yield 18%).

$^1$H-NMR(300 MHz, DMSO-$d_6$)δ(ppm): 3.08-3.16(4H, m), 3.60-3.69(4H, m), 6.96-7.14(5H, m), 7.26-7.34(1H, m), 7.41(1H, d, J=8.1 Hz), 7.61(1H, d, J=8.1 Hz), 9.10(1H, s), 12.49(1H, s). MS(ESI)m/z:340[M+H]$^+$.

Example 85

Ethyl 1H-indazol-3-ylcarbamate (81 mg) and 1-(2-fluorophenyl)piperazine (Aldrich Co., 47 mg) were dissolved in dimethylformamide (2 ml), and the mixture was stirred with heating at 100° C. for 11 hr. After allowing to cool, water was added to the reaction mixture, and the precipitated solid was collected by filtration and dried to give 4-(2-fluorophenyl)-1-piperazinecarboxylic acid (1H-indazol-3-yl)amide (48 mg, yield 57%).

$^1$H-NMR(300 MHz, DMSO-$d_6$)δ(ppm): 3.01-3.08(4H, m), 3.63-3.69(4H, m), 6.97-7.22(5H, m), 7.25-7.34(1H, m), 7.41(1H, d, J=8.1 Hz), 7.62(1H, d, J=8.1 Hz), 9.09(1H, s), 12.49(1H, s). MS(ESI)m/z:340[M+H]$^+$.

Example 86

By a similar operation as in Example 1, 4-(2,4-difluorophenyl)-1-piperazinecarboxylic acid (1H-indazol-3-yl)amide (338 mg, yield 65%) was obtained from ethyl 1H-indazol-3-ylcarbamate (300 mg) and 1-(2,4-difluorophenyl)piperazine (ACROS CO., 290 mg).

$^1$H-NMR(300 MHz, DMSO-$d_6$)δ(ppm): 2.96-3.04(4H, m), 3.62-3.69(4H, m), 6.96-7.34(5H, m), 7.41(1H, d, J=8.1 Hz), 7.62(1H, d, J=8.1 Hz), 9.07(1H, s), 12.47(1H, s). MS(ESI)m/z:358[M+H]$^+$.

Example 87

By a similar operation as in Example 38, 4-(2-thienyl)-1-piperazinecarboxylic acid (1H-indazol-3-yl)amide (166 mg, yield 42%) was obtained from ethyl 1H-indazol-3-ylcarbamate (250 mg) and the compound (250 mg) of Starting Material Synthetic Example 15.

$^1$H-NMR(400 MHz, DMSO-$d_6$)δ(ppm): 3.03-3.16(4H, m), 3.60-3.69(4H, m), 6.24-6.28(1H, m), 6.77-6.80(1H, m), 6.97-7.05(1H, m), 7.26-7.33(1H, m), 7.41(1H, d, J=8.4 Hz), 7.60(1H, d, J=8.4 Hz), 9.15(1H, s), 12.51(1H, s). MS(ESI)m/z:328[M+H]$^+$.

Example 88

By a similar operation as in Example 38, 4-[5-(trifluoromethyl)pyridin-2-yl]-1-piperazinecarboxylic acid (1H-indazol-3-yl)amide (28 mg, yield 7%) was obtained from ethyl 1H-indazol-3-ylcarbamate (200 mg) and 1-[5-(trifluoromethyl)pyridin-2-yl]piperazine (ACROS CO., 295 mg).

$^1$H-NMR(300 MHz, DMSO-$d_6$)δ(ppm): 3.60(4H, t, J=3.3 Hz), 3.71(4H, t, J=3.3 Hz), 6.95-7.03(2H, m), 7.24-7.32(1H, m), 7.39(1H, d, J=8.4 Hz), 7.60(1H, d, J=8.4 Hz), 7.78-7.85 (1H, m), 8.42(1H, s), 9.09(1H, s), 12.48(1H, s). MS(ESI)m/z:391[M+H]$^+$.

Example 89

By a similar operation as in Example 1, 4-[3-(trifluoromethyl)pyridin-2-yl]-1-piperazinecarboxylic acid (1H-indazol-3-yl)amide (41 mg, yield 11%) was obtained from ethyl 1H-indazol-3-ylcarbamate (200 mg) and 1-[3-(trifluoromethyl)pyridin-2-yl]piperazine (ACROS CO., 224 mg).

$^1$H-NMR(300 MHz, DMSO-$d_6$)δ(ppm): 3.21(4H, t, J=4.5),3.62(4H, t, J=4.5 Hz), 6.97-7.04(1H, m), 7.21-7.32 (2H, m), 7.36-7.42(1H, m), 7.57-7.63(1H, m), 8.06-8.12(1H, m), 8.53-8.58(1H, m), 9.06(1H, s), 12.47(1H, s). MS(ESI)m/z:391[M+H]$^+$.

Example 90

By a similar operation as in Example 1, 4-(5-fluoropyrimidin-2-yl)-1-piperazinecarboxylic acid (1H-indazol-3-yl)amide (4 mg, yield 1%) was obtained from the compound (11)(200 mg) of the above-mentioned formula and 5-fluoro-2-piperazin-1-ylpyrimidine (synthesized according to the method described in Chem. Pharm. Bull., 39, 1991, 2288-2300, 177 mg).

¹H-NMR(400 MHz, DMSO-d₆)δ(ppm): 3.52-3.63(4H, m), 3.68-3.79(4H, m), 6.95-7.03(1H, m), 7.23-7.42(3H, m), 7.57-7.62(1H, m), 8.48(2H, s), 9.08(1H, s), 12.47(1H, s). MS(ESI)m/z:342[M+H]⁺.

Example 91

By a similar operation as in Example 1, 4-[4-(morpholine-4-ylmethyl)phenyl]-1-piperazinecarboxylic acid (1H-indazol-3-yl)amide (151 mg, yield 37%) was obtained from ethyl 1H-indazol-3-ylcarbamate (200 mg) and the compound (261 mg) of Starting Material Synthetic Example 16.

¹H-NMR(300 MHz, DMSO-d₆)δ(ppm): 2.25-2.34(4H, m), 3.11-3.18(4H, m), 3.47-3.67(8H, m), 6.93(2H, d, J=8.4 Hz), 6.95-7.02(1H, m), 7.14(2H, d, J=8.4 Hz), 7.24-7.31(1H, m), 7.39(1H, d, J=8.4 Hz), 7.59(1H, d, J=8.4 Hz), 9.07(1H, s), 12.47(1H, s).

Example 92

By a similar operation as in Example 1, 4-(3-chloro-4-fluorophenyl)-1-piperazinecarboxylic acid (1H-indazol-3-yl)amide (59 mg, yield 16%) was obtained from ethyl 1H-indazol-3-ylcarbamate (200 mg) and 1-(3-chloro-4-fluorophenyl)piperazine (APOLLO CO., 215 mg).

¹H-NMR(300 MHz, DMSO-d₆)δ(ppm): 3.16(4H, t, J=4.8 Hz), 3.62(4H, t, J=4.8 Hz), 6.95-7.03(2H, m), 7.11-7.17(1H, m), 7.21-7.32(2H, m), 7.36-7.41(1H, m), 7.53-7.61(1H, m), 9.09(1H, s), 12.47(1H, s). MS(ESI)m/z:374[M+H]⁺.

Example 93

By a similar operation as in Example 38, 4-[4-chloro-3-(trifluoromethyl)phenyl]-1-piperazinecarboxylic acid (1H-indazol-3-yl)amide (140 mg, yield 27%) was obtained from ethyl 1H-indazol-3-ylcarbamate (250 mg) and 1-[4-chloro-3-(trifluoromethyl)phenyl]piperazine (APOLLO CO., 404 mg).

¹H-NMR(300 MHz, DMSO-d₆)δ(ppm): 3.26-3.54(4H, m), 3.61-3.69(4H, m), 6.96-7.06(1H, m), 7.24-7.34(3H, m), 7.38-7.43(1H, m), 7.49-7.54(1H, m), 7.60-7.64(1H, m), 9.10(1H, s), 12.48(1H, s). MS(ESI)m/z:424[M+H]⁺.

Example 94

By a similar operation as in Example 38, 4-[4-fluoro-3-(trifluoromethyl)phenyl]-1-piperazinecarboxylic acid (1H-indazol-3-yl)amide (265 mg, yield 53%) was obtained from ethyl 1H-indazol-3-ylcarbamate (250 mg) and the compound (382 mg) of Starting Material Synthetic Example 17.

¹H-NMR(300 MHz, DMSO-d₆)δ(ppm): 3.19-3.27(4H, m), 3.61-3.75(4H, m), 7.02(1H, t, J=7.8 Hz), 7.22-7.44(5H, m), 7.63(1H, d, J=7.8 Hz), 9.12(1H, s), 12.50(1H, brs). MS(ESI)m/z:408[M+H]⁺.

Example 95

By a similar operation as in Example 38, 4-[4-methoxy-3-(trifluoromethyl)phenyl]-1-piperazinecarboxylic acid (1H-indazol-3-yl)amide (331 mg, yield 65%) was obtained from ethyl 1H-indazol-3-ylcarbamate (250 mg) and the compound (398 mg) of Starting Material Synthetic Example 18.

¹H-NMR(300 MHz, DMSO-d₆)δ(ppm): 3.09-3.17(4H, m), 3.61-3.69(4H, m), 3.82(3H, s), 6.98-7.05(1H, m), 7.14-7.34(4H, m), 7.41(1H, d, J=8.1 Hz), 7.62(1H, d, J=8.1 Hz), 9.08(1H, s), 12.47(1H, s). MS(ESI)m/z:420[M+H]⁺.

Example 96

By a similar operation as in Example 38, 4-[4-(trifluoromethyl)-1,3-thiazol-2-yl]-1-piperazinecarboxylic acid (1H-indazol-3-yl)amide (65 mg, yield 26%) was obtained from ethyl 1H-indazol-3-ylcarbamate (130 mg) and the compound (190 mg) of Starting Material Synthetic Example 19.

¹H-NMR(300 MHz, DMSO-d₆)δ(ppm): 3.42-3.74(8H, m), 6.96-7.05(1H, m), 7.25-7.44(2H, m), 7.57-7.66(2H, m), 9.17(1H, s), 12.49(1H, s). MS(ESI)m/z:397[M+H]⁺.

Example 97

By a similar operation as in Example 38, 4-[3-fluoro-5-(trifluoromethyl)phenyl]-1-piperazinecarboxylic acid (1H-indazol-3-yl)amide (127 mg, yield 32%) was obtained from ethyl 1H-indazol-3-ylcarbamate (198 mg) and the compound (300 mg) of Starting Material Synthetic Example 20.

¹H-NMR(300 MHz, DMSO-d₆)δ(ppm): 3.30-3.42(4H, m), 3.61-3.69(4H, m), 6.93(1H, d, J=8.4 Hz), 6.98-7.05(1H, m), 7.10-7.17(2H, m), 7.26-7.34(1H, m), 7.41(1H, d, J=8.4 Hz), 7.60-7.64(1H, m), 9.13(1H, s), 12.50(1H, s). MS(ESI)m/z:408[M+H]⁺.

Example 98

Ethyl 1H-indazol-3-ylcarbamate (250 mg), 1-(3,4-dichlorophenyl)piperazine (KANTO CHEMICAL CO. INC., 310 mg) and DBU (200 μl) were dissolved in dimethyl sulfoxide (4 ml), and the mixture was stirred with heating at 100° C. for 1 hr. By the work-up following the method of Example 12, 4-(3,4-dichlorophenyl)-1-piperazinecarboxylic acid (1H-indazol-3-yl)amide (240 mg, yield 50%) was obtained.

¹H-NMR(300 MHz, DMSO-d₆)δ(ppm): 3.21-3.28(4H, m), 3.60-3.67(4H, m), 6.97-7.05(2H, m), 7.19-7.45(4H, m), 7.58-7.64(1H, m), 9.12(1H, s), 12.50(1H, s). MS(ESI)m/z:390[M+H]⁺.

Example 99

By a similar operation as in Example 12, 4-[2-chloro-5-(trifluoromethyl)phenyl]-1-piperazinecarboxylic acid (1H-indazol-3-yl)amide (45 mg, yield 11%) was obtained from ethyl 1H-indazol-3-ylcarbamate (200 mg) and 1-[2-chloro-5-(trifluoromethyl)phenyl]piperazine (synthesized according to the method described in Tetrahedron Lett., 35, 40, 1994, 7331-7334, 283 mg).

¹H-NMR(300 MHz, DMSO-d₆)δ(ppm): 3.07-3.14(4H, m), 3.65-3.71(4H, m), 6.98-7.06(1H, m), 7.26-7.34(1H, m), 7.38-7.48(3H, m), 7.63(1H, d, J=8.4 Hz), 7.70(1H, d, J=8.4 Hz), 9.11(1H, s), 12.50(1H, s). MS(ESI)m/z:424[M+H]⁺.

Example 100

By a similar operation as in Example 1, 4-[3-(trifluoromethyl)phenyl]-1-piperazinecarboxylic acid (1H-indazol-3-yl)amide (314 mg, yield 84%) was obtained from ethyl 1H-indazol-3-ylcarbamate (197 mg) and 1-[3-(trifluoromethyl)phenyl]piperazine (Aldrich Co., 221 mg).

¹H-NMR(300 MHz, DMSO-d₆)δ(ppm): 3.20-3.33(4H, m), 3.60-3.80(4H, m), 6.99-7.12(2H, m), 7.25-7.63(6H, m), 9.14(1H, s), 12.51(1H, s). MS(ESI)m/z:390[M+H]⁺.

Example 101

By a similar operation as in Example 1, 4-[2-(trifluoromethyl)phenyl]-1-piperazinecarboxylic acid (1H-indazol-3-yl)

amide (140 mg, yield 39%) was obtained from ethyl 1H-indazol-3-ylcarbamate (191 mg) and 1-[2-(trifluoromethyl)phenyl]piperazine (CHESS Co., 216 mg).

$^1$H-NMR(300 MHz, DMSO-d$_6$)δ(ppm): 2.88-2.94(4H, m), 3.60-3.67(4H, m), 7.03(1H, t, J=7.5 Hz), 7.32(1H, t, J=7.5 Hz), 7.38-7.43(2H, m), 7.62-7.72(4H, m), 9.09(1H, s), 12.51(1H, s). MS(ESI)m/z:390[M+H]$^+$.

Example 102

By a similar operation as in Example 1, 4-(2-cyanophenyl)-1-piperazinecarboxylic acid (1H-indazol-3-yl)amide (44 mg, yield 15%) was obtained from ethyl 1H-indazol-3-ylcarbamate (178 mg) and 1-(2-cyanophenyl)piperazine (Aldrich Co., 166 mg).

$^1$H-NMR(300 MHz, DMSO-d$_6$)δ(ppm): 3.17-3.23(4H, m), 3.66-3.73(4H, m), 7.03(1H, t, J=6.9 Hz), 7.14(1H, t, J=6.9 Hz), 7.23-7.43(3H, m), 7.61-7.76(3H, m), 9.12(1H, s), 12.51(1H, s). MS(ESI)m/z:347[M+H]$^+$.

Example 103

By a similar operation as in Example 12, 5-oxo-1,5-dihydro-2H-chromeno[3,4-c]pyridine-3-carboxylic acid (1H-indazol-3-yl)amide (180 mg, yield 52%) was obtained from ethyl 1H-indazol-3-ylcarbamate (196 mg) and 1,2,3,4-tetrahydro-5H-chromeno[3,4-c]pyridine-5-one (synthesized according to the method described in J. Heterocycl. Chem., 21, 1984, 1557-1559, 202 mg).

$^1$H-NMR(400 MHz, DMSO-d$_6$)δ(ppm): 3.01(2H, t, J=5.5 Hz), 3.8.5(2H, t, J=5.5 Hz), 4.46(2H, s), 6.97-7.84(8H, m), 9.33(1H, s), 12.52(1H, s). MS(ESI)m/z:361[M+H]$^+$.

Example 104

By a similar operation as in Example 12, 5-oxo-1,4,5,6-tetrahydrobenzo[c]-2,7-naphthyridine-3-carboxylic acid (1H-indazol-3-yl)amide (439 mg, yield 84%) was obtained from ethyl 1H-indazol-3-ylcarbamate (300 mg) and 2,3,4,6-tetrahydrobenzo[c]-2,7-naphthyridine-5(1H)-one (synthesized according to the method described in J. Heterocycl. Chem., 23, 1986, 941-944, 307 mg).

$^1$H-NMR(400 MHz, DMSO-d$_6$)δ(ppm): 3.01(2H, t, J=5.5 Hz), 3.83(2H, t, J=5.5 Hz), 4.47(2H, s), 6.97-7.78(8H, m), 9.26(1H, s), 11.85(1H, s), 12.50(1H, s). MS(ESI)m/z:360[M+H]$^+$.

Example 105

By a similar operation as in Example 12, 3,4-dihydropirazino[1,2-a]benzimidazole-2-carboxylic acid (1H-indazol-3-yl)amide (204 mg, yield 52%) was obtained from ethyl 1H-indazol-3-ylcarbamate (240 mg) and 1,2,3,4-tetrahydropirazino[1,2-a]benzimidazole (synthesized according to the method described in Bull. Chem. Soc. Chim. Fr., 1991, 255-259, 213 mg).

$^1$H-NMR(400 MHz, DMSO-d$_6$)δ(ppm): 4.08-4.30(4H, m), 4.99(2H, s), 6.98-7.64(8H, m), 9.45(1H, s), 12.57(1H, s). MS(ESI)m/z:333[M+H]$^+$.

Example 106

By a similar operation as in Example 12, 3,4-dihydropirazino[1,2-a]indole-2-carboxylic acid (1H-indazol-3-yl)amide (302 mg, yield 62%) was obtained from ethyl 1H-indazol-3-ylcarbamate (300 mg) and 1,2,3,4-tetrahydropirazino[1,2-a]indole (synthesized according to the method described in Bioorg. Med. Chem. Lett., 12, 2, 2002, 155-158, 264 mg).

$^1$H-NMR(400 MHz, DMSO-d$_6$)δ(ppm): 4.07(2H, t, J=5.5 Hz), 4.19(2H, t, J=5.5 Hz), 4.95(2H, s), 6.31(1H, s), 6.97-7.63(8H, m), 9.30(1H, s), 12.51(1H, s). MS(ESI)m/z:332[M+H]$^+$.

Example 107

By a similar operation as in Example 12, 1-(morpholine-4-ylmethyl)-1,3,4,9-tetrahydro-β-carboline-2-carboxylic acid (1H-indazol-3-yl)amide (252 mg, yield 50%) was obtained from ethyl 1H-indazol-3-ylcarbamate (239 mg) and the compound (347 mg) of Starting Material Synthetic Example 21.

$^1$H-NMR(400 MHz, DMSO-d$_6$)δ(ppm): 2.53-2.64(2H, m), 2.67-2.98(6H, m), 3.19-3.25(1H, m), 3.68-3.82(4H, m), 4.42-4.52(1H, m), 5.49(1H, brs), 6.93-7.66(8H, m), 10.16(1H, brs), 10.88(1H, s), 12.41(1H, s). MS(ESI)m/z:431[M+H]$^+$.

Example 108

By a similar operation as in Example 12, 1-[(dimethylamino)methyl]-1,3,4,9-tetrahydro-β-carboline-2-carboxylic acid (1H-indazol-3-yl)amide (187 mg, yield 40%) was obtained from ethyl 1H-indazol-3-ylcarbamate (244 mg) and the compound (300 mg) of Starting Material Synthetic Example 22.

$^1$H-NMR(400 MHz, DMSO-d$_6$)δ(ppm): 2.39(6H, s), 2.66-2.92(4H, m), 3.21-3.34(1H, m), 4.41-4.50(1H, m), 5.49(1H, brs), 6.94-7.64(8H, m), 9.85(1H, brs), 10.83(1H, s), 12.38(1H, s). MS(ESI)m/z:389[M+H]$^+$.

Example 109

By a similar operation as in Example 12, 6-oxo-1,4,5,6-tetrahydrobenzo[c]-1,7-naphthyridine-3-carboxylic acid (1H-indazol-3-yl)amide (435 mg, yield 67%) was obtained from ethyl 1H-indazol-3-ylcarbamate (370 mg) and the compound (448 mg) of Starting Material Synthetic Example 23.

$^1$H-NMR(400 MHz, DMSO-d$_6$)δ(ppm): 2.77-2.83(2H, m), 3.86-3.92(2H, m), 4.46(2H, s), 6.97-8.25(8H, m), 9.26(1H, s), 11.30(1H, s), 12.49(1H, s). MS(ESI)m/z:360[M+H]$^+$.

Example 110

By a similar operation as in Example 1, 4-phenyl-1-piperidinecarboxylic acid (1H-indazol-3-yl)amide (157 mg, yield 51%) was obtained from ethyl 1H-indazol-3-ylcarbamate (200 mg) and 4-phenylpiperidine (Chess Co., 161 mg).

$^1$H-NMR(300 MHz, DMSO-d$_6$)δ(ppm): 1.56-1.64(2H, m), 1.77-1.81(2H, m), 2.73-2.74(1H, m), 2.86-2.94(2H, m), 4.27-4.32(2H, m), 6.97-7.76(9H, m), 8.96(1H, s), 12.43(1H, s). MS(ESI)m/z:321[M+H]$^+$.

Example 111

By a similar operation as in Example 1, 4-(2-fluorophenyl)-1-piperidinecarboxylic acid (1H-indazol-3-yl)amide (11 mg, yield 3%) was obtained from ethyl 1H-indazol-3-ylcarbamate (200 mg) and 4-(2-fluorophenyl)piperidine hydrochloride (Arch Co., 216 mg).

¹H-NMR(300 MHz, DMSO-d₆)δ(ppm): 1.63-1.73(2H, m), 2.89-3.04(3H, m), 4.27-4.32(2H, m), 6.99-7.60(8H, m), 8.97(1H, s), 12.43(1H, s). MS(ESI)m/z:339[M+H]⁺.

Example 112

By a similar operation as in Example 1, 4-[3-(trifluoromethyl)phenyl]piperidine-1-carboxylic acid (1H-indazol-3-yl)amide (64 mg, yield 17%) was obtained from ethyl 1H-indazol-3-ylcarbamate (200 mg) and 4-[3-(trifluoromethyl)phenyl]piperidine hydrochloride (Arch Co., 266 mg).

¹H-NMR(300 MHz, DMSO-d₆)δ(ppm): 1.60-1.65(2H, m), 1.80-1.84(2H, m), 2.87-2.94(2H, m), 4.29-4.33(2H, m), 6.97-7.62(8H, m), 8.97(1H, s), 12.43(1H, s). MS(ESI)m/z: 389[M+H]⁺.

Example 113

By a similar operation as in Example 1, 3-phenyl-1-piperidinecarboxylic acid (1H-indazol-3-yl)amide (243 mg, yield 62%) was obtained from ethyl 1H-indazol-3-ylcarbamate (250 mg) and 3-phenylpiperidine (Chess Co., 216 mg).

¹H-NMR(300 MHz, DMSO-d₆)δ(ppm): 1.56-1.74(3H, m), 1.95-1.98(1H, m), 2.73-2.77(1H, m), 2.83-2.96(2H, m), 4.21-4.25(2H, m), 6.87-7.62(9H, m), 9.01(1H, s), 12.45(1H, s). MS(ESI)m/z:321[M+H]⁺.

Example 114

By a similar operation as in Example 1, 4-(morpholin-4-ylcarbonyl)-4-phenylpiperidine-1-carboxylic acid (1H-indazol-3-yl)amide (265 mg, yield 63%) was obtained from ethyl 1H-indazol-3-ylcarbamate (200 mg) and the compound (280 mg) of Starting Material Synthetic Example 77.

¹H-NMR(300 MHz, DMSO-d₆)δ(ppm): 1.87-1.94(2H, m), 2.24-2.29(2H, m), 3.20-3.46(10H, m), 4.02-4.07(2H, m), 6.99-7.83(9H, m), 8.98(1H, s), 12.44(1H, s). MS(ESI)m/z: 434[M+H]⁺.

Example 115

By a similar operation as in Example 1, 4-(methoxymethyl)-4-phenylpiperidine-1-carboxylic acid (1H-indazol-3-yl)amide (578 mg, yield 58%) was obtained from ethyl 1H-indazol-3-ylcarbamate (214 mg) and the compound (236 mg) of Starting Material Synthetic Example 78.

¹H-NMR(300 MHz, DMSO-d₆)δ(ppm): 1.86-1.92(2H, m), 2.09-2.13(2H, m), 3.08-3.35(5H, m), 3.78-3.81(2H, m), 6.97-7.58(9H, m), 8.93(1H, s), 12.45(1H, s). MS(ESI)m/z: 365[M+H]⁺.

Example 116

By a similar operation as in Example 1, 4-[4-chloro-3-(trifluoromethyl)phenyl]-4-methoxypiperidine-1-carboxylic acid (1H-indazol-3-yl)amide (1.20 g, yield 60%) was obtained from ethyl 1H-indazol-3-ylcarbamate (908 mg) and the compound (1.56 g) of Starting Material Synthetic Example 79.

¹H-NMR(400 MHz, DMSO-d₆)δ(ppm): 1.89-2.05(4H, m), 2.96(3H, s), 3.11-3.13(2H, m), 4.07-4.11(2H, m), 6.98-7.79(7H, m), 9.02(1H, s), 12.45(1H, s). MS(ESI)m/z:453 [M+H]⁺.

Example 117

By a similar operation as in Example 12, 4-[4-chloro-3-(trifluoromethyl)phenyl]-3-methylpiperazine-1-carboxylic acid (1H-indazol-3-yl)amide (564 mg, yield 72%) was obtained from ethyl 1H-indazol-3-ylcarbamate (380 mg) and the compound (693 mg) of Starting Material Synthetic Example 80.

¹H-NMR(400 MHz, DMSO-d₆)δ(ppm): 1.05-1.07(3H, m), 3.11-3.13(2H, m), 4.01-4.11(1H, m), 4.17-4.18(2H, m), 7.01-7.61(7H, m), 9.07(1H, s), 12.47(1H, s). MS(ESI)m/z: 438[M+H]⁺.

Example 118

By a similar operation as in Example 12, 5-methyl-4-phenyl-3,6-dihydropyridine-1(2H)-carboxylic acid (1H-indazol-3-yl)amide (101 mg, yield 7%) was obtained from ethyl 1H-indazol-3-ylcarbamate (892 mg) and the compound (1.13 g) of Starting Material Synthetic Example 81.

¹H-NMR(400 MHz, DMSO-d₆)δ(ppm): 1.45(3H, s), 2.23-2.24(2H, m), 3.51-3.54(2H, m), 3.84-3.85(2H, m), 6.84-7.48 (9H, m), 8.78(1H, s), 12.27(1H, s). MS(ESI)m/z:333[M+H]⁺.

Example 119

The compound (500 mg) of Starting Material Synthetic Example 83, cesium carbonate (958 mg) and tetrabutylammoniumiodide (1.10 g) were dissolved in dimethylformamide (2 ml), and the mixture was stirred at room temperature for 30 min. Methyl iodide (0.18 ml) was added to the reaction mixture, and the mixture was stirred at room temperature for 30 min. After completion of the reaction, ethyl acetate was added thereto, and the insoluble material was filtered off. The filtrate was concentrated, ethanol (5 ml) and a 1N aqueous sodium hydroxide solution (5 ml) were added, and the mixture was stirred at room temperature for 1 hr. After completion of the reaction, the reaction mixture was neutralized with 1N aqueous hydrochloric acid. The precipitated solid was collected by filtration and dried to give 4-[4-chloro-3-(trifluoromethyl)phenyl]-4-hydroxypiperidine-1-carboxylic acid(1H-indazol-3-yl-N-methyl)amide (229 mg, yield 52%).

¹H-NMR(400 MHz, DMSO-d₆)δ(ppm): 1.32-1.54(4H, m), 2.84-3.01(2H, m), 3.24(3H, s), 3.74-3.88(2H, m), 5.32 (1H, s), 7.01-7.89(7H, m), 12.89(1H, s). MS(ESI)m/z:453 [M+H]⁺.

Example 120

The compound (520 mg) of Example 93, ethyl chloroformate (0.14 ml) and pyridine (0.12 ml) were dissolved in tetrahydrofuran (5 ml), and the mixture was heated under reflux for 2 hr. After completion of the reaction, the reaction mixture was concentrated. Water was added to the mixture and the precipitated solid was collected by filtration. The solid was dried and dissolved in dimethylformamide (1 ml). The mixture was cooled to 0° C. and sodium hydride (51 mg) was added thereto. The mixture was stirred for 1 hr and methyl iodide (182 mg) was added thereto. The mixture was stirred at 0° C. for 1 hr and then at room temperature for 1 hr. After completion of the reaction, water was added thereto, and the mixture was extracted three times with chloroform. The organic layer was dried and the solvent was evaporated under reduced pressure. Ethanol (5 ml) and a 1N aqueous sodium hydroxide solution (2 ml) were added to the obtained residue, and the mixture was stirred at room temperature for 1 hr. After completion of the reaction, the reaction mixture was neutralized with 1N aqueous hydrochloric acid, and the mixture was extracted three times with chloroform. The organic layer was dried and the solvent was evaporated under reduced pressure. The obtained residue was purified by silica gel column chromatography (elution solvent: hexane-ethyl acetate (1:1-1:2)) to give 4-[4-chloro-3-(trifluoromethyl)phenyl]-1-piperazinecarboxylic acid (1H-indazol-3-yl-N-methyl)amide (51 mg, yield 11%).

$^1$H-NMR(400 MHz, DMSO-d$_6$)δ(ppm): 2.97-2.99(4H, m), 3.25-3.29(4H, m), 7.05-7.51(7H, m), 12.71(1H, s). MS(ESI)m/z:438[M+H]$^+$.

Example 121

By a similar operation as in Example 119, 4-(4-fluorophenyl)-3,6-dihydropyridine-1(2H)-carboxylic acid(1H-indazol-3-yl-N-methyl)amide (93 mg, yield 22%) was obtained from compound (500 mg) of Starting Material Synthetic Example 84 and methyl iodide (0.22 ml).

$^1$H-NMR(400 MHz, DMSO-d$_6$)δ(ppm): 2.11-2.13(2H, m), 3.23(3H, s), 3.36-3.37(2H, m), 3.70-3.71(2H, m), 5.98 (1H, s), 7.05-7.50(8H, m), 12.71(1H, s). MS(ESI)m/z:351 [M+H]$^+$.

Example 122

By a similar operation as in Example 119, 4-(4-fluorophenyl)-3,6-dihydropyridine-1(2H)-carboxylic acid[1H-indazol-3-yl-N-(3-butene)-1-yl]amide (133 mg, yield 28%) was obtained from compound (500 mg) of Starting Material Synthetic Example 84 and 4-bromo-1-butene (0.31 ml).

$^1$H-NMR(400 MHz, DMSO-d$_6$)δ(ppm): 2.03-2.04(2H, m), 2.30-2.36(2H, m), 3.27-3.38(2H, m), 3.66-3.75(4H, m), 4.92-5.01(2H, m), 5.75-5.82(1H, m), 5.94(1H, s), 7.04-7.50 (8H, m), 12.74(1H, s). MS(ESI)m/z:391[M+H]$^+$.

Example 123

By a similar operation as in Example 12, 4-[4-chloro-3-(trifluoromethyl)phenyl]-4-fluoropiperidine-1-carboxylic acid (1H-indazol-3-yl)amide (501 mg, yield 60%) was obtained from ethyl 1H-indazol-3-ylcarbamate (398 mg) and the compound (655 mg) of Starting Material Synthetic Example 82.

$^1$H-NMR(400 MHz, DMSO-d$_6$)δ(ppm): 1.95-1.98(2H, m), 2.10-2.22(2H, m), 3.15-3.18(2H, m), 4.25-4.28(2H, m), 7.02-7.88(7H, m), 9.06(1H, s), 12.43(1H, s). MS(ESI)m/z: 441[M+H]$^+$.

Example 124 Missing Number

Example 125

By a similar operation as in Example 1, 4-pyridin-3-yl-1,4-diazepane-1-carboxylic acid (1H-indazol-3-yl)amide (202 mg, yield 62%) was obtained from ethyl 1H-indazol-3-ylcarbamate (200 mg) and 1-pyridin-2-yl-1,4-diazepane (synthesized according to the method described in Chem. Pharm. Bull., 49, 10, 2001, 1314-1320, 173 mg).

$^1$H-NMR(300 MHz, DMSO-d$_6$)δ(ppm): 1.86-1.99(2H, m), 3.43-3.47(2H, m), 3.60-3.64(2H, m), 3.66-3.73(4H, m), 6.90(1H, t, J=7.5 Hz), 7.15-7.18(3H, m), 7.26(1H, t, J=7.5 Hz), 7.35-7.38(1H, m), 7.84(1H, s), 8.17(1H, s), 8.80(1H, s), 12.42(1H, s). MS(ESI)m/z:337[M+H]$^+$.

Example 126

By a similar operation as in Example 1, 3-(3-fluorophenyl)-3-hydroxy-1-piperidinecarboxylic acid (1H-indazol-3-yl)amide (128 mg, yield 47%) was obtained from ethyl 1H-indazol-3-ylcarbamate (160 mg) and the compound (180 mg) of Starting Material Synthetic Example 89.

$^1$H-NMR(300 MHz, DMSO-d$_6$)δ(ppm): 3.75-3.82(2H, m), 3.86-3.92(2H, m), 4.30(2H, s), 7.01-7.06(1H, m), 7.23-7.34(3H, m), 7.41-7.46(3H, m), 7.61-7.67(1H, m), 9.18(1H, s), 12.54(1H, s). MS(ESI)m/z:354[M+H]$^+$.

Example 127

By a similar operation as in Example 1, 3-(4-fluorophenyl)-3-hydroxy-1-pyrrolidinecarboxylic acid (1H-indazol-3-yl)amide (2 mg, yield 2%) was obtained from ethyl 1H-indazol-3-ylcarbamate (50 mg) and 3-(4-fluorophenyl)pyrrolidine-3-ol hydrochloride (synthesized according to the method described in J. Med. Chem., 42, 22, 1999, 4680-4694, 50 mg).

$^1$H-NMR(300 MHz, DMSO-d$_6$)δ(ppm): 2.50-2.54(2H, m), 3.47-3.72(4H, m), 5.54(1H, s), 6.99-7.04(1H, m), 7.16-7.42(4H, m), 7.57-7.85(4H, m), 8.63(1H, s), 12.02(1H, s). MS(ESI)m/z:341[M+H]$^+$.

Example 128

By a similar operation as in Example 1, 3-[4-chloro-3-(trifluoromethyl)phenyl]-3-hydroxy-1-piperidinecarboxylic acid (1H-indazol-3-yl)amide (78 mg, yield 22%) was obtained from ethyl 1H-indazol-3-ylcarbamate (170 mg) and the compound (262 mg) of Starting Material Synthetic Example 44.

$^1$H-NMR(300 MHz, DMSO-d$_6$)δ(ppm): 1.51-1.56(1H, m), 1.68-1.72(1H, m), 1.98-2.02(1H, m), 2.65-2.78(1H, m), 2.94-3.07(1H, m), 3.84-3.89(1H, m), 3.98-4.02(1H, m), 4.12-4.16(1H, m), 5.64(1H, s), 7.00(1H, t, J=7.3 Hz), 7.29(1H, t, J=7.3 Hz), 7.39(1H, d, J=8.1 Hz), 7.64(1H, d, J=8.1 Hz), 7.70(2H, s), 8.22(1H, s), 8.83(1H, s), 12.40(1H, s). MS(ESI) m/z:439[M+H]$^+$.

Example 129

By a similar operation as in Example 1, 4-hydroxy-4-(2-methylphenyl)-1-piperidinecarboxylic acid (1H-indazol-3-yl)amide (1.1 g, yield 47%) was obtained from ethyl 1H-indazol-3-ylcarbamate (1.3 g) and the compound (1.2 g) of Starting Material Synthetic Example 91.

$^1$H-NMR(300 MHz, DMSO-d$_6$)δ(ppm): 1.82-1.86(2H, m), 1.95-2.04(2H, m), 2.58(3H, s), 3.26-3.35(2H, m), 4.04-4.08(2H, m), 4.99(1H, s), 6.98-7.03(1H, s), 7.14-7.17(3H, s), 7.27-7.32(1H, m), 7.39-7.45(2H, m), 7.59-7.62(1H, m), 8.97 (1H, s), 12.44(1H, s). MS(ESI)m/z:351[M+H]$^+$.

Example 130

By a similar operation as in Example 1, 4-(2-fluoro-5-methylphenyl)-4-hydroxy-1-piperidinecarboxylic acid (1H-indazol-3-yl)amide (1.2 g, yield 57%) was obtained from ethyl 1H-indazol-3-ylcarbamate (1.2 g) and the compound (1.2 g) of Starting Material Synthetic Example 92.

$^1$H-NMR(300 MHz, DMSO-d$_6$)δ(ppm): 1.55-1.60(2H, m), 2.15-2.20(2H, m), 2.31(3H, s), 3.22-3.31(2H, m), 4.04-4.08(2H, m), 5.31(1H, s), 7.00-7.09(3H, m), 7.30-7.50(3H, m), 7.59-7.63(1H, m), 9.00(1H, s), 12.45(1H, s). MS(ESI)m/z:369[M+H]$^+$.

Example 131

By a similar operation as in Example 1, 4-(3-chloro-2-methylphenyl)-4-hydroxy-1-piperidinecarboxylic acid (1H- indazol-3-yl)amide (400 mg, yield 67%) was obtained from ethyl 1H-indazol-3-ylcarbamate (320 mg) and the compound (350 mg) of Starting Material Synthetic Example 93.

$^1$H-NMR(300 MHz, DMSO-d$_6$)δ(ppm): 1.88-2.01(4H, m), 2.63(3H, s), 3.28-3.37(2H, m), 4.05-4.09(2H, m), 5.22 (1H, s), 6.98-7.03(1H, m), 7.17-7.44(5H, m), 7.58-7.62(1H, m), 8.99(1H, s), 12.45(1H, s). MS(ESI) m/z:385[M+H]$^+$.

Example 132

By a similar operation as in Example 1, 4-(3-chloro-4-methylphenyl)-4-hydroxy-1-piperidinecarboxylic acid (1H-indazol-3-yl)amide (84 mg, yield 57%) was obtained from ethyl 1H-indazol-3-ylcarbamate (78 mg) and the compound (86 mg) of Starting Material Synthetic Example 94.

$^1$H-NMR(300 MHz, DMSO-d$_6$)δ(ppm): 1.61(2H, d, J=13.2 Hz), 1.86-1.94(2H, m), 2.31(3H, s), 3.20-3.28(2H, m), 4.08(2H, d, J=13.2 Hz), 5.22(1H, s), 6.99-7.04(1H, m), 7.27-7.42(4H, m), 7.62-7.64(1H, m), 8.96(1H, s), 12.45(1H, s). MS(ESI)m/z:385[M+H]$^+$.

Example 133

By a similar operation as in Example 1, 4-(3-fluoro-4-methylphenyl)-4-hydroxy-1-piperidinecarboxylic acid (1H-indazol-3-yl)amide (1.5 g, yield 55%) was obtained from ethyl 1H-indazol-3-ylcarbamate (1.5 g) and the compound (1.5 g) of Starting Material Synthetic Example 95.

$^1$H-NMR(300 MHz, DMSO-d$_6$)δ(ppm): 1.61(2H, d, J=13.2 Hz), 1.86-1.93(2H, m), 2.21(3H, s), 3.20-3.28(2H, m), 4.07(2H, d, J=13.2 Hz), 5.18(1H, s), 6.99-7.04(1H, m), 7.19-7.32(4H, m), 7.39-7.42(1H, m), 7.61-7.64(1H, m), 8.96 (1H, s), 12.45(1H, s). MS(ESI)m/z:369[M+H]$^+$.

Example 134

By a similar operation as in Example 1, 4-(3-fluoro-2-methylphenyl)-4-hydroxy-1-piperidinecarboxylic acid (1H-indazol-3-yl)amide (993 mg, yield 59%) was obtained from ethyl 1H-indazol-3-ylcarbamate (940 mg) and the compound (960 mg) of Starting Material Synthetic Example 96.

$^1$H-NMR(300 MHz, DMSO-d$_6$)δ(ppm): 1.84-2.01(4H, m), 2.49(3H, s), 3.27-3.34(2H, m), 4.05-4.09(2H, m), 5.18 (1H, s), 6.99-7.09(2H, m), 7.16-7.41(4H, m), 7.59-7.62(1H, m), 8.98(1H, s), 12.45(1H, s). MS(ESI)m/z:369[M+H]$^+$.

Example 135

By a similar operation as in Example 1, 4-(5-fluoro-2-methylphenyl)-4-hydroxy-1-piperidinecarboxylic acid (1H-indazol-3-yl)amide (1.3 g, yield 63%) was obtained from ethyl 1H-indazol-3-ylcarbamate (1.1 g) and the compound (1.1 g) of Starting Material Synthetic Example 97.

$^1$H-NMR(300 MHz, DMSO-d$_6$)δ(ppm): 1.75-1.79(2H, m), 1.99-2.07(2H, m), 2.53(3H, s), 3.25-3.34(2H, m), 4.06-4.10(2H, m), 5.14(1H, s), 6.97-7.42(6H, m), 7.59-7.63(1H, m), 8.99(1H, s), 12.45(1H, s). MS(ESI)m/z:369[M+H]$^+$.

Example 136

By a similar operation as in Example 1, 4-(4-fluoro-3-methylphenyl)-4-hydroxy-1-piperidinecarboxylic acid (1H-indazol-3-yl)amide (1.0 g, yield 63%) was obtained from ethyl 1H-indazol-3-ylcarbamate (920 mg) and the compound (900 mg) of Starting Material Synthetic Example 98.

$^1$H-NMR(300 MHz, DMSO-d$_6$)δ(ppm): 1.62(2H, d, J=12.9 Hz), 1.86-1.94(2H, m), 2.25(3H, s), 3.20-3.27(2H, m), 4.07(2H, d, J=12.9 Hz), 5.11(1H, s), 6.99-7.11(2H, m), 7.27-7.42(4H, m), 7.62-7.64(1H, m), 8.96(1H, s), 12.45(1H, s). MS(ESI)m/z:369[M+H]$^+$.

Example 137

By a similar operation as in Example 1, 4-hydroxy-4-(4-methylphenyl)-1-piperidinecarboxylic acid (1H-indazol-3-yl)amide (1.4 g, yield 62%) was obtained from ethyl 1H-indazol-3-ylcarbamate (1.35 g) and the compound (1.3 g) of Starting Material Synthetic Example 99.

$^1$H-NMR(300 MHz, DMSO-d$_6$)δ(ppm): 1.62(2H, d, J=13.1 Hz), 1.84-1.94(2H, m), 2.28(3H, s), 3.22-3.26(2H, m), 4.06(2H, d, J=13.1 Hz), 5.02(1H, s), 6.99-7.04(1H, m), 7.13-7.16(2H, m), 7.27-7.41(4H, m), 7.61-7.64(1H, m), 8.95 (1H, s), 12.44(1H, s). MS(ESI)m/z:351[M+H]$^+$.

Example 138

By a similar operation as in Example 1, 4-(3-fluoro-5-methylphenyl)-4-hydroxy-1-piperidinecarboxylic acid (1H-indazol-3-yl)amide (878 mg, yield 55%) was obtained from ethyl 1H-indazol-3-ylcarbamate (890 mg) and the compound (960 mg) of Starting Material Synthetic Example 100.

$^1$H-NMR(300 MHz, DMSO-d$_6$)δ(ppm): 1.61(2H, d, J=12.8 Hz), 1.86-1.96(2H, m), 2.33(3H, s), 3.20-3.29(2H, m), 4.09(2H, d, J=12.8 Hz), 5.21(1H, s), 6.87-7.16(4H, m), 7.27-7.42(2H, m), 7.62-7.65(1H, m), 8.96(1H, s), 12.46(1H, s). MS(ESI)m/z:369[M+H]$^+$.

Example 139

By a similar operation as in Example 1, 4-(2,5-dimethylphenyl)-4-hydroxy-1-piperidinecarboxylic acid (1H-indazol-3-yl)amide (2.09 g, yield 40%) was obtained from ethyl 1H-indazol-3-ylcarbamate (2.96 g) and the compound (3.11 g) of Starting Material Synthetic Example 101.

$^1$H-NMR(400 MHz, DMSO-d$_6$)δ(ppm): 1.81(2H, d, J=12.5 Hz), 1.94-2.05(2H, m), 2.27(3H, s), 2.52(3H, s), 3.25-3.35(2H, m), 4.06(2H, d, J=12.5 Hz), 4.92(1H, s), 6.92-7.04 (3H, m), 7.23-7.32(2H, m), 7.40(1H, d, J=7.8 Hz), 7.61(1H, d, J=7.8 Hz), 8.94(1H, s), 12.42(1H, s). MS(ESI)m/z:365[M+H]$^+$.

Example 140

By a similar operation as in Example 1, 4-hydroxy-4-[2-methyl-3-(trifluoromethyl)phenyl]-1-piperidinecarboxylic acid (1H-indazol-3-yl)amide (1.14 g, yield 47%) was obtained from ethyl 1H-indazol-3-ylcarbamate (1.20 g) and the compound (2.17 g) of Starting Material Synthetic Example 102.

$^1$H-NMR(400 MHz, DMSO-d$_6$)δ(ppm): 1.92-2.06(4H, m), 2.74(3H, s), 3.28-3.39(2H, m), 4.08(2H, d, J=12.5 Hz), 5.26(1H, s), 6.98-7.03(1H, m), 7.26-7.32(1H, m), 7.34-7.42 (2H, m), 7.59-7.64(2H, m), 7.74(1H, d, J=7.8 Hz), 8.96(1H, s), 12.43(1H, s). MS(ESI)m/z:419[M+H]$^+$.

Example 141

By a similar operation as in Example 1, 4-hydroxy-4-[2-methyl-5-(trifluoromethyl)phenyl]-1-piperidinecarboxylic acid (1H-indazol-3-yl)amide (1.49 g, yield 37%) was obtained from ethyl 1H-indazol-3-ylcarbamate (2.00 g) and the compound (3.58 g) of Starting Material Synthetic Example 103.

$^1$H-NMR(400 MHz, DMSO-d$_6$)δ(ppm): 1.80(2H, d, J=12.5 Hz), 2.04-2.15(2H, m), 2.66(3H, s), 3.26-3.36(2H, m), 4.10(2H, d, J=12.5 Hz), 5.26(1H, s), 6.98-7.04(1H, m), 7.27-7.33(1H, m), 7.37-7.43(2H, m), 7.52(1H, d, J=7.8 Hz), 7.62(1H, d, J=7.8 Hz), 7.78(1H, s), 8.99(1H, s), 12.44(1H, s). MS(ESI)m/z:419[M+H]$^+$.

Example 142

By a similar operation as in Example 12, 4-(3,4-dimethylphenyl)-4-hydroxy-1-piperidinecarboxylic acid (1H-indazol-3-yl)amide (923 mg, yield 26%) was obtained from ethyl 1H-indazol-3-ylcarbamate (2.0 g) and the compound (2.42 g) of Starting Material Synthetic Example 104.

$^1$H-NMR(400 MHz, DMSO-d$_6$)δ(ppm): 1.53(2H, d, J=12.9 Hz), 1.80-1.81(2H, m), 2.11(3H, s), 2.14(3H, s), 3.17-3.23(2H, m), 3.96(2H, d, J=12.9 Hz), 4.87(1H, s), 6.93-7.55 (7H, m), 8.84(1H, s), 12.34(1H, s). MS(ESI)m/z:365[M+H]$^+$.

Example 143

By a similar operation as in Example 12, 4-(3,5-dimethylphenyl)-4-hydroxy-1-piperidinecarboxylic acid (1H-indazol-3-yl)amide (1.57 g, yield 50%) was obtained from ethyl 1H-indazol-3-ylcarbamate (1.8 g) and the compound (1.78 g) of Starting Material Synthetic Example 105.

$^1$H-NMR(400 MHz, DMSO-d$_6$)δ(ppm): 1.60(2H, d, J=12.9 Hz), 1.86-1.93(2H, m), 2.27(6H, m), 3.22-3.31(2H, m), 4.06(2H, d, J=12.9 Hz), 4.97(1H, s), 6.85-7.64(7H, m), 8.92(1H, s), 12.43(1H, s). MS(ESI)m/z:365[M+H]$^+$.

Example 144

Ethyl 1H-indazol-3-ylcarbamate (1.2 g) and the compound (1.46 g) of Starting Material Synthetic Example 106 were dissolved in dimethylformamide (10 ml), DBU (2.3 ml) was added thereto, and the mixture was stirred with heating at 120° C. for 2 hr. After completion of the reaction, the reaction mixture was diluted with methanol (3 ml) and 1N hydrochloric acid and water were added to the mixture. The precipitated solid was collected by filtration and vacuum dried to give 4-(2,3-dimethylphenyl)-4-hydroxy-1-piperidinecarboxylic acid (1H-indazol-3-yl)amide (1.02 g, yield 47%).

$^1$H-NMR(400 MHz, DMSO-d$_6$)δ(ppm): 1.88-2.03(4H, m), 2.24(3H, s), 2.49(3H, s), 3.32-3.36(2H, m), 4.04-4.08 (2H, m), 4.99(1H, s), 6.99-7.63(7H, m), 8.95(1H, s), 12.43 (1H, s). MS(ESI)m/z:365[M+H]$^+$.

The structural formulas of the compounds of respective Examples are shown in the following.

Formulas 17

Example 1

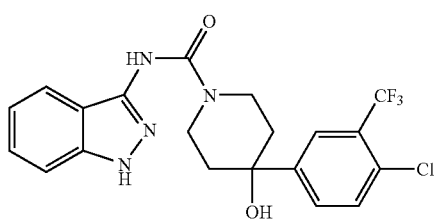

Example 2

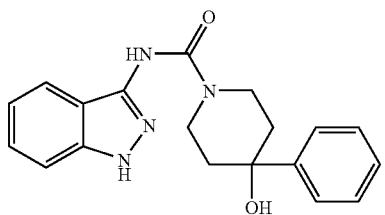

Example 3

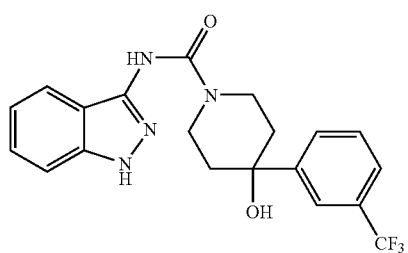

Example 4

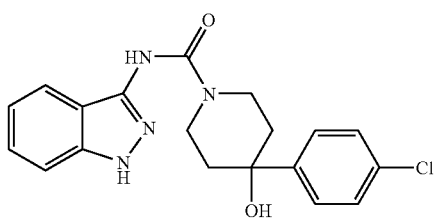

Example 5

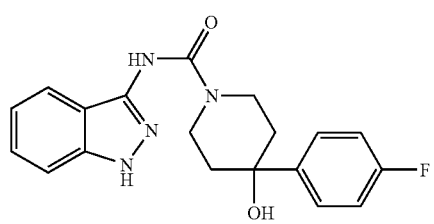

Example 6

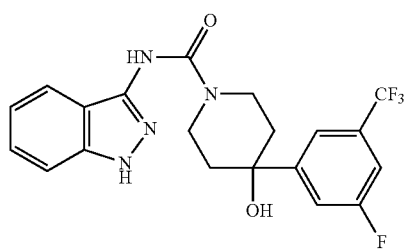

Example 7

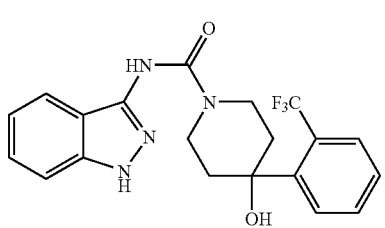

Example 8

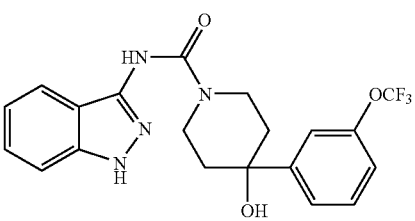

Example 9
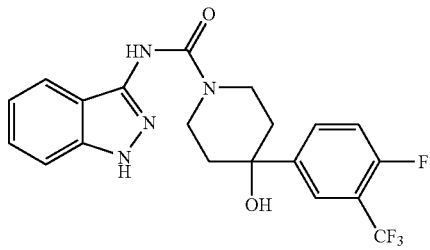
Example 10
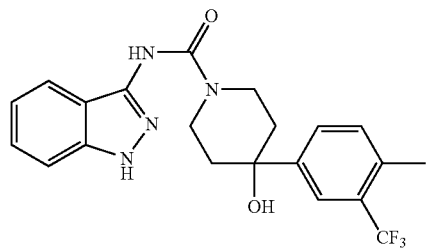
Example 11
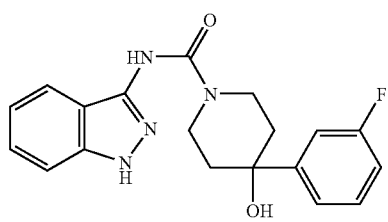
Example 12
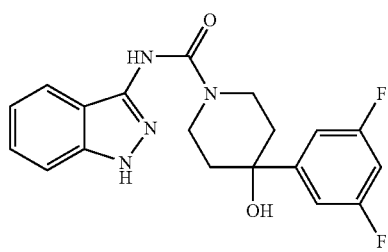
Example 13
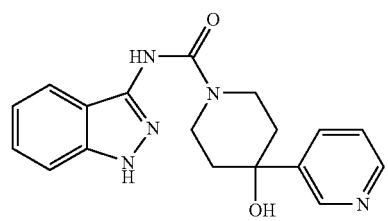
Example 14
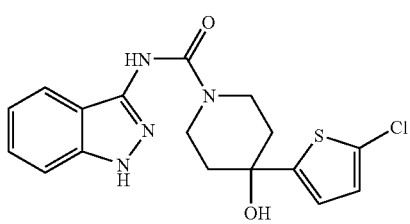
Example 15
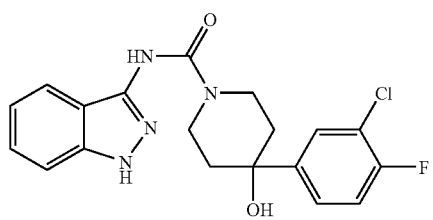
Example 16
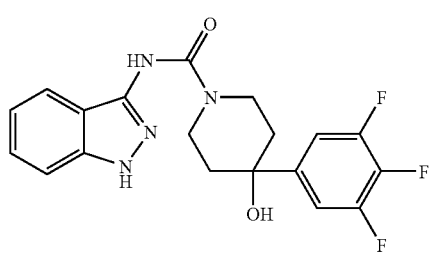
Formulas 18
Example 17
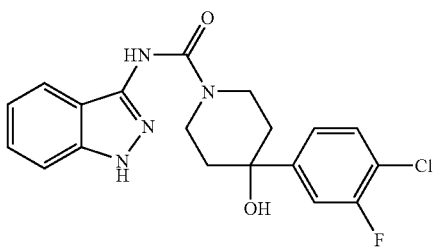
Example 18
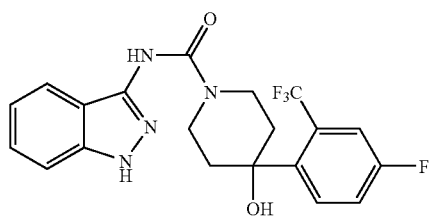
Example 19
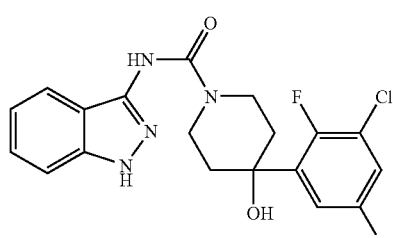
Example 20
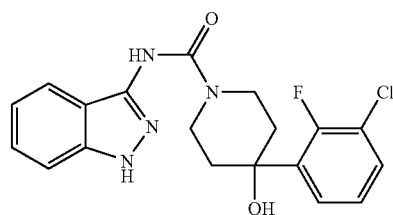

-continued

Example 21, Example 22, Example 23, Example 24, Example 25, Example 26, Example 27, Example 28, Example 29, Example 30, Example 31, Example 32, Example 33, Example 34

-continued

Formulas 19

Example 35

Example 36

Example 37

Example 38

Example 39

Example 40

-continued

Example 41

Example 42

Example 43

Example 44

Example 45

Example 46

Example 47

Example 48 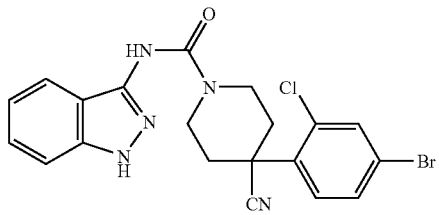
Example 49 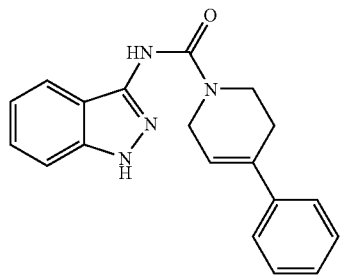
Example 50 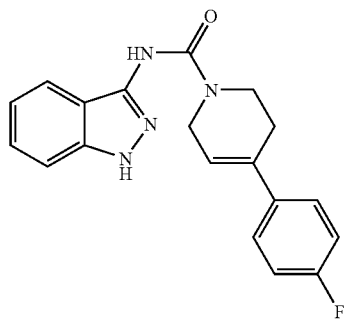
Formulas 20
Example 51 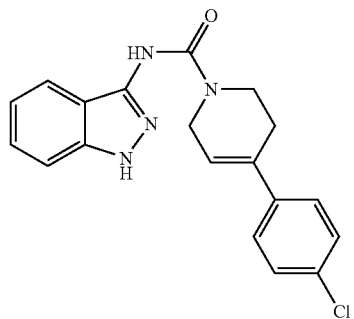
Example 52 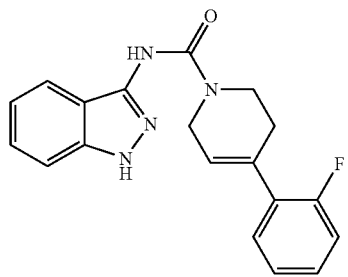
Example 53 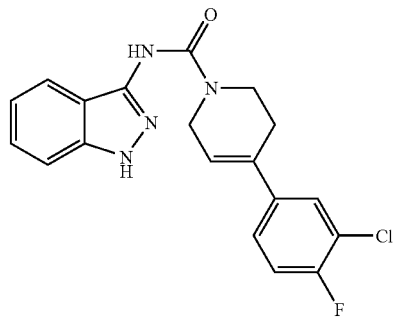
Example 54 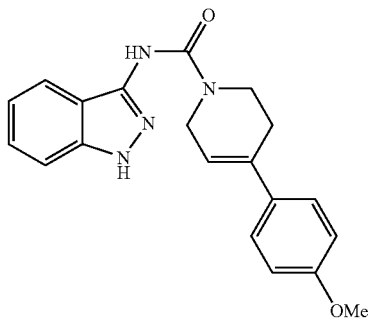
Example 55 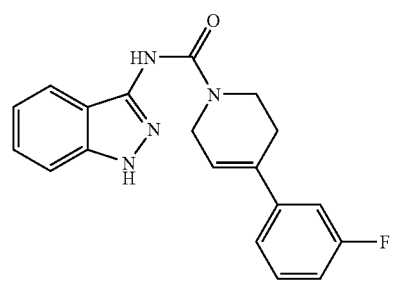
Example 56 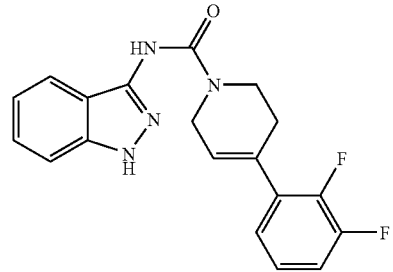
Example 57 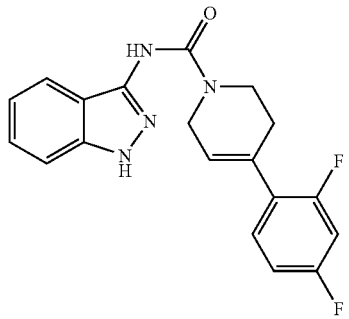

Example 58 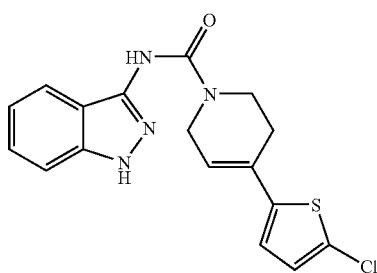
Example 59 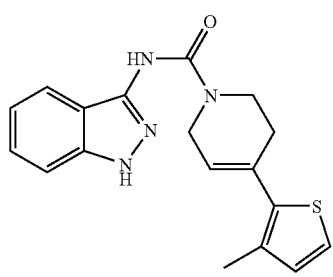
Example 60 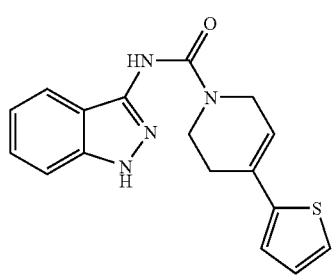
Example 61 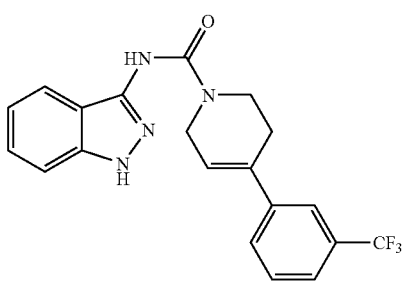
Example 62 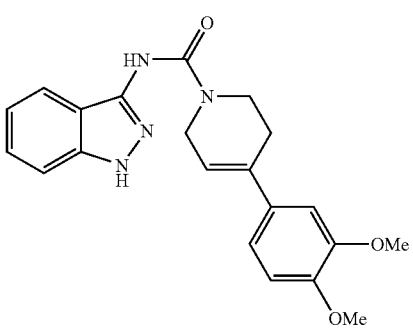
Example 63 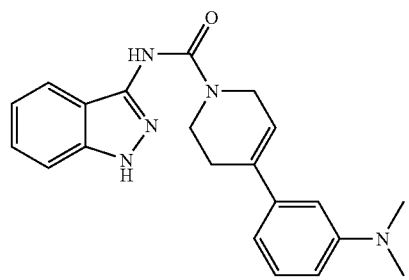
Example 64 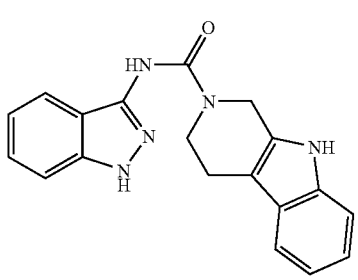
Example 65 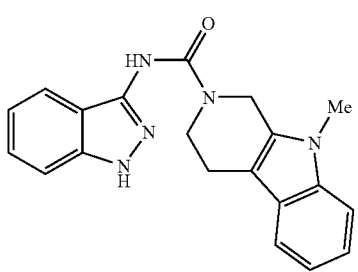
Example 66 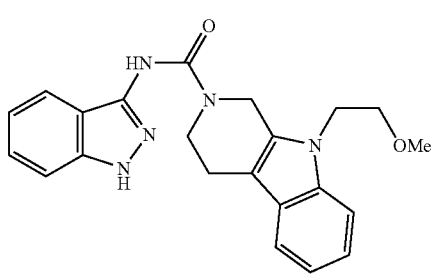
Formulas 21
Example 67 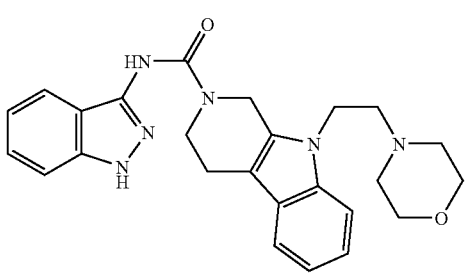
Example 68 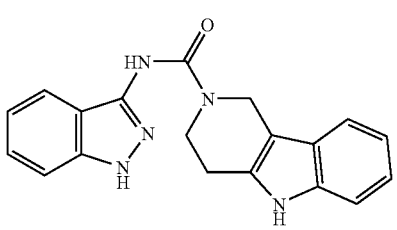

Example 69 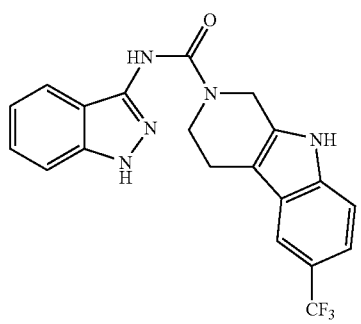
Example 70 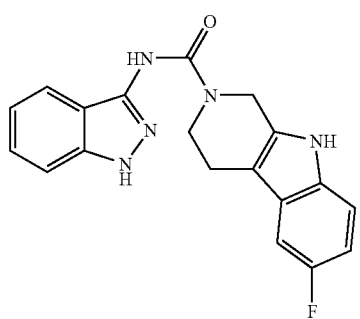
Example 71 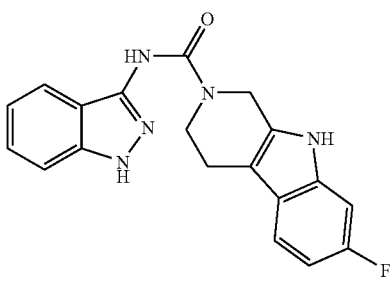
Example 72 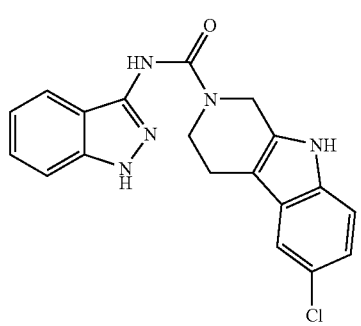
Example 73 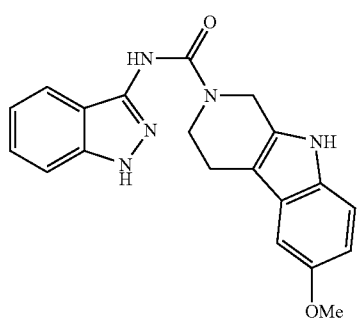
Example 74 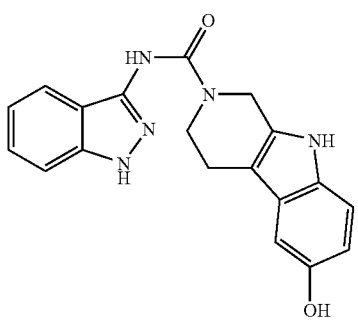
Example 75 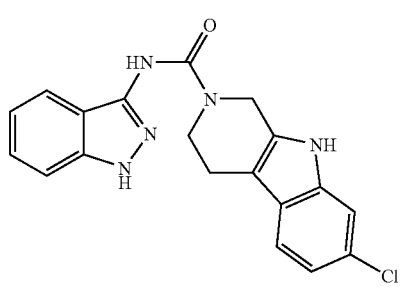
Example 76 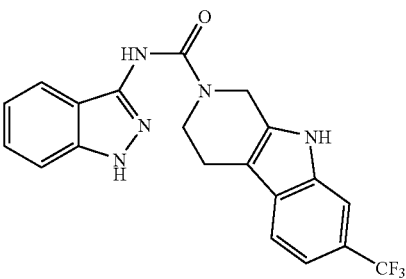
Example 77 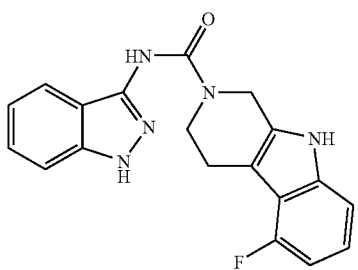
Example 78 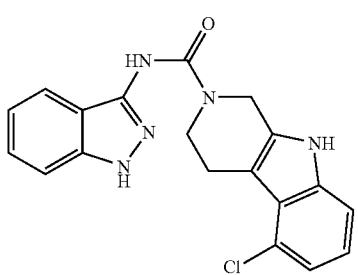

| | |
|---|---|
| Example 79 | 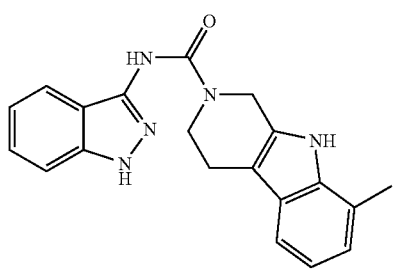 |
| Example 80 | 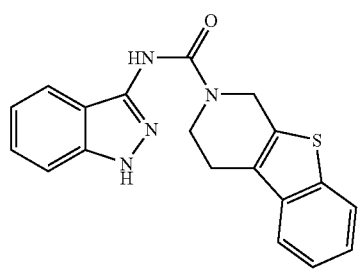 |
| Example 81 | 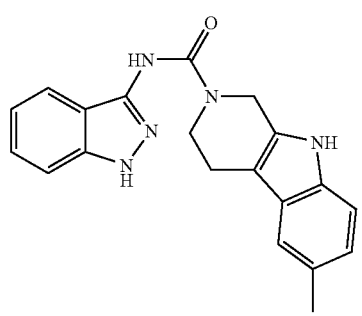 |
| Example 82 | 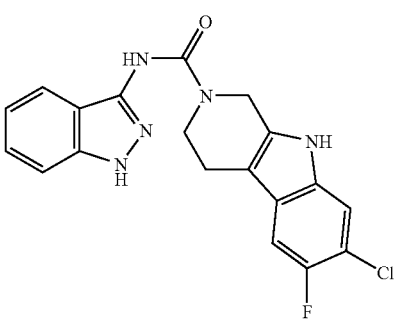 |
| Example 83 | 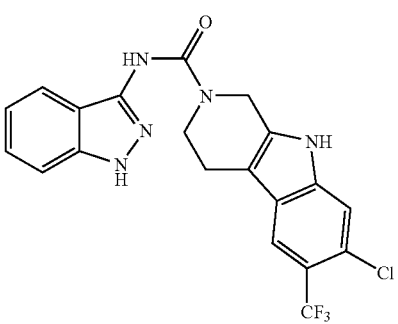 |
Formulas 22
| | |
|---|---|
| Example 84 | 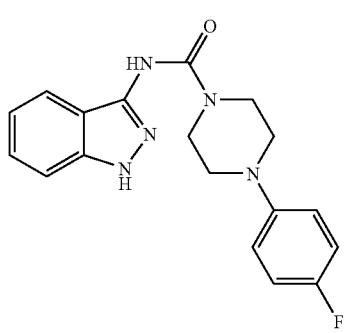 |
| Example 85 | 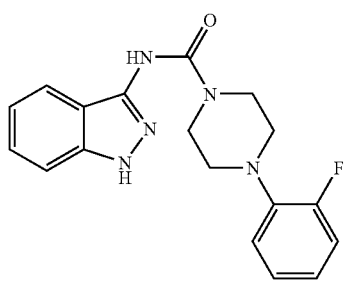 |
| Example 86 | 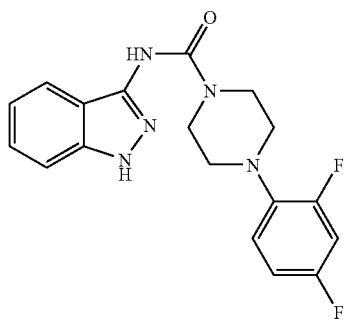 |
| Example 87 | 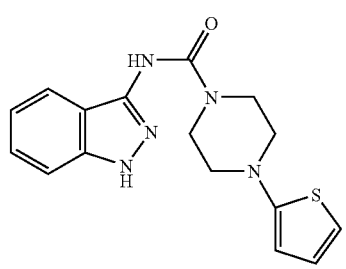 |
| Example 88 | 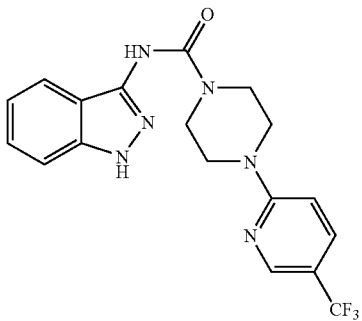 |

| | |
|---|---|
| Example 89 | 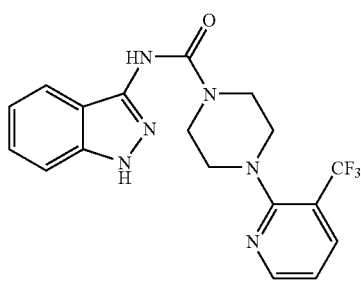 |
| Example 90 | 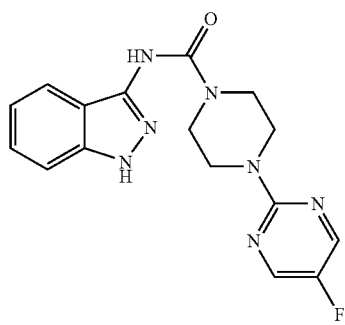 |
| Example 91 | 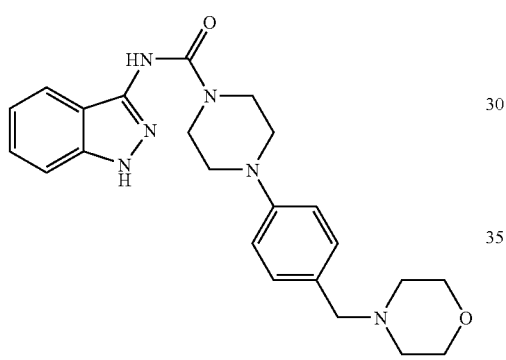 |
| Example 92 | 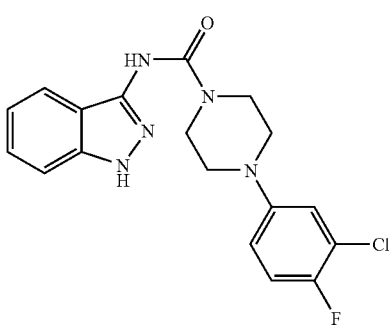 |
| Example 93 | 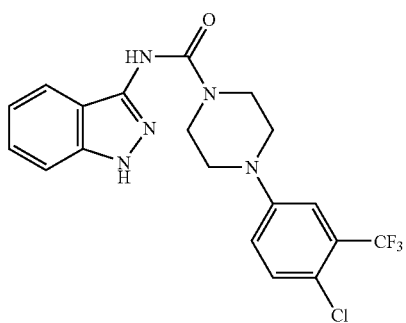 |
| Example 94 | 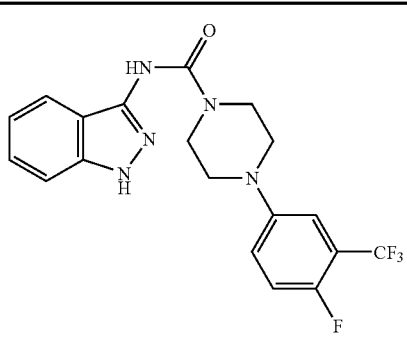 |
| Example 95 | 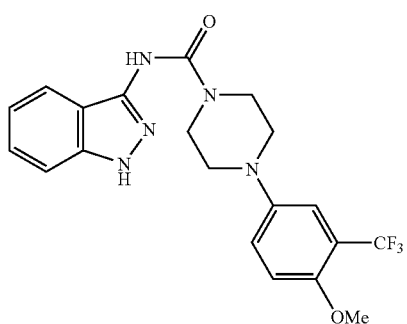 |
| Example 96 | 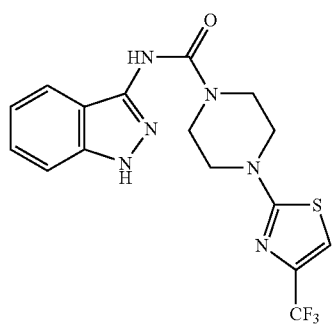 |
| Example 97 | 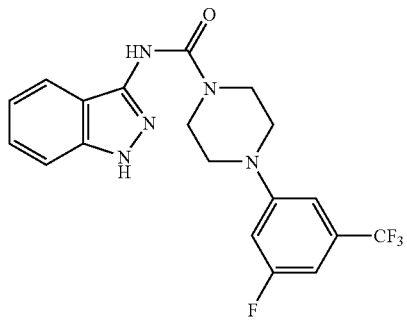 |
Formulas 23

Example 98 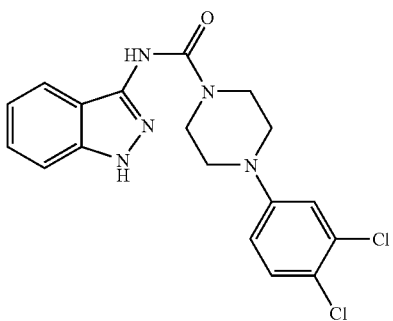
Example 103 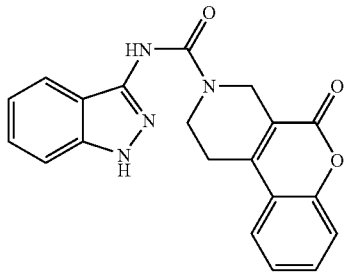
Example 99 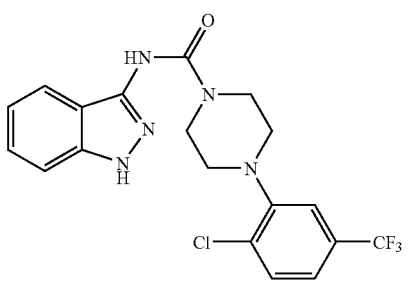
Example 104 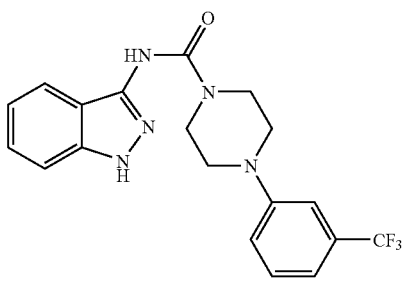
Example 100 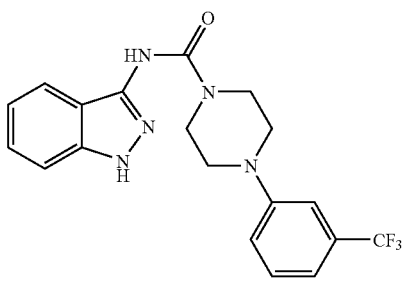
Example 105 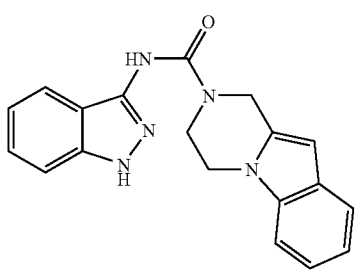
Example 101 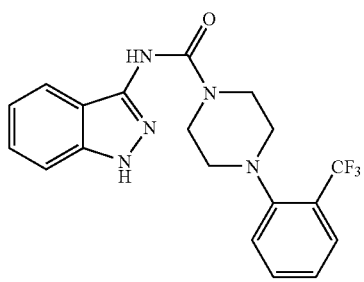
Example 106 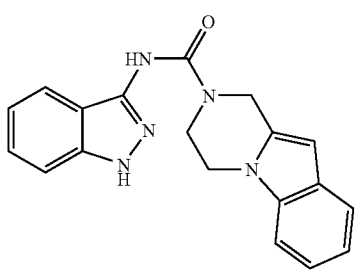
Example 102 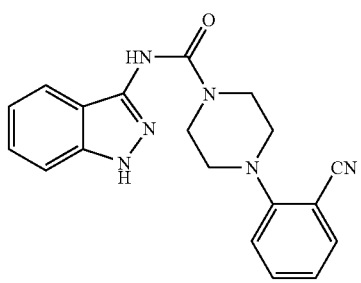
Example 107 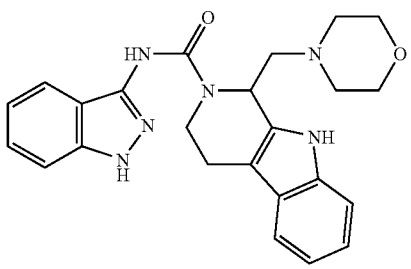

Example 108 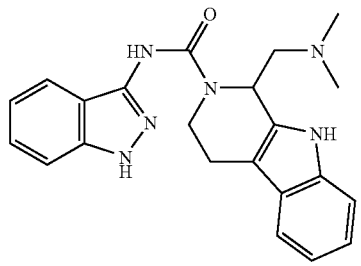
Example 109 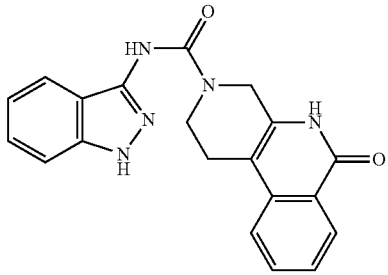
Example 110 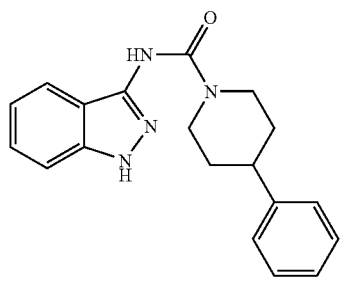
Example 111 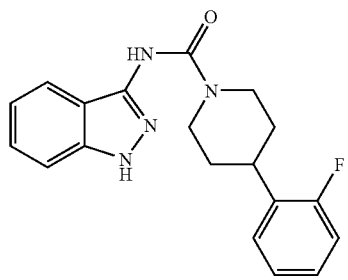
Example 112 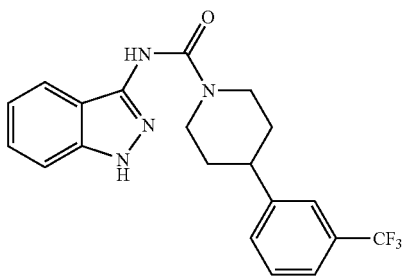
Formulas 24
Example 113 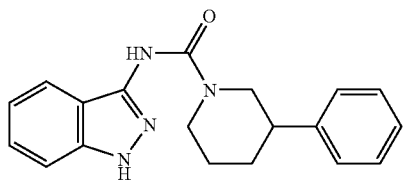
Example 114 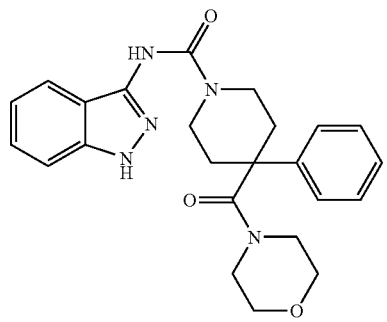
Example 115 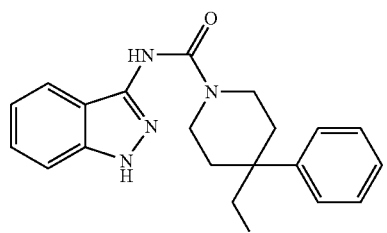
Example 116 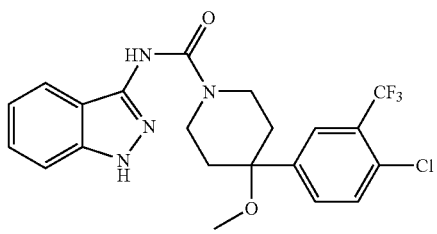
Example 117 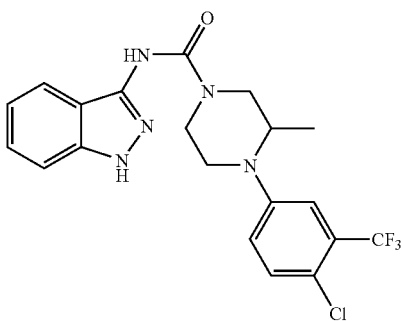
Example 118 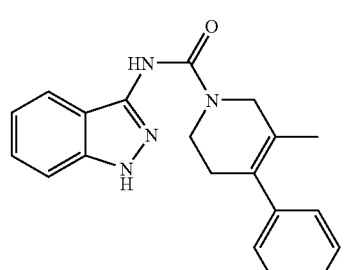

| | |
|---|---|
| Example 119 | (structure) |
| Example 120 | (structure) |
| Example 121 | (structure) |
| Example 122 | (structure) |
| Example 123 | (structure) |
| Example 124 | missing number |
| Example 125 | (structure) |
| Example 126 | (structure) |

Formulas 25

| | |
|---|---|
| Example 127 | (structure) |
| Example 128 | (structure) |
| Example 129 | (structure) |
| Example 130 | (structure) |

Example 131 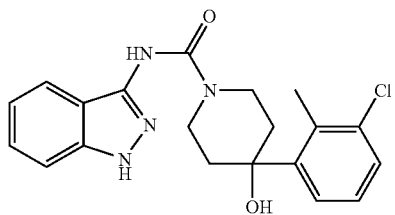
Example 132 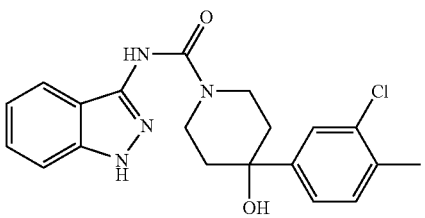
Example 133 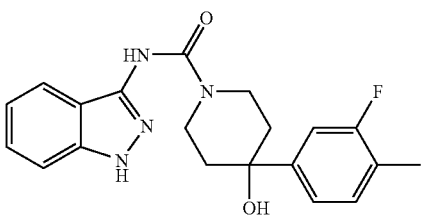
Example 134 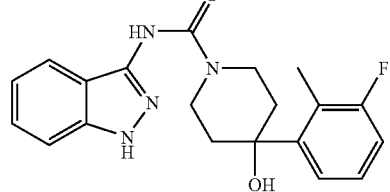
Example 135 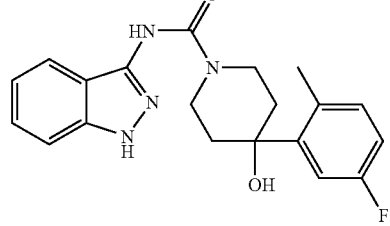
Example 136 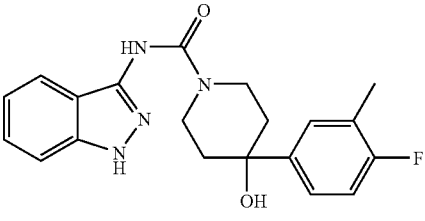
Example 137 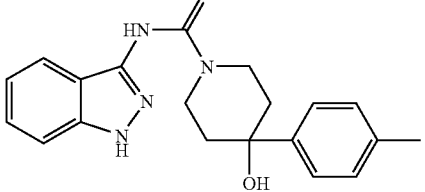
Example 138 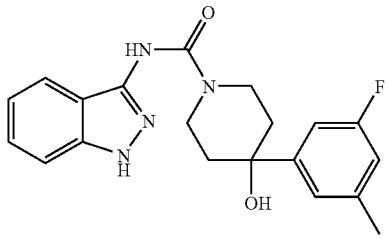
Example 139 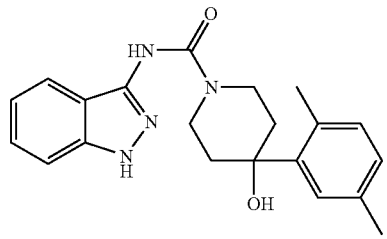
Example 140 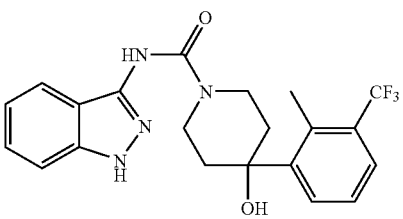
Example 141 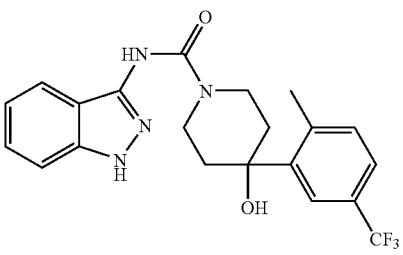
Example 142 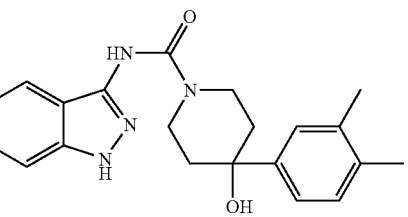
Example 143 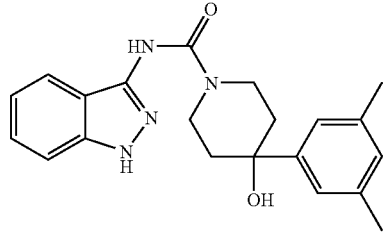

Example 144

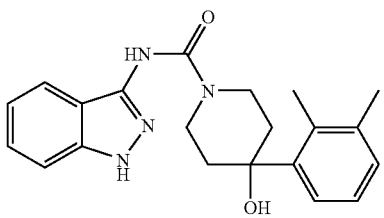

Pharmacological Experimental Example 1

Determination of MMP-9 Production Inhibitory Activity

Immortalized human vascular endothelial cells HEC3 (supplied by Prof. Iijima of Nagoya University) were subcultured in RPMI1640 medium (Sigma Ltd.) containing 10% fetal calf serum.

The HEC3 cells ($5 \times 10^4$ cells/well) were plated on a 24-well plate, and cultured in RPMI1640 medium containing 10% fetal calf serum for 24 hr. Each well was washed once with serum-free RPMI1640 medium. Then, RPMI1640 medium (250 μl/well) containing 0.05% fetal calf serum was added to each well, and the cells were further cultured for 2 hr.

The supernatant was removed, and the test substances (Example compounds shown in Table 1) diluted to various concentrations were added and incubated for 1 hr in 0.05% serum-containing RPMI1640 medium and the supernatant was removed again. A medium containing a test substance having the same concentration as in the pre-treatment and PMA ($10^{-7}$ M), which was a stimulant, was added at 250 μl/well, and the cells were further cultured for 24 hr.

After completion of the culture, water (50 μl) and 25 μl of SDS buffer (240 mM Tris-HCl (pH 6.8), 8% SDS, 40% glycerol) were added to the culture supernatant (25 μl), and the mixture (10 μl) was electrophoresed on a 7.5% polyacrylamide gel containing 0.1% gelatin.

After the electrophoresis, the gel was washed with Tris-HCl buffer (pH 7.5) containing 0.5% Triton X-100 (Sigma Ltd.) for 1 hr. The gel was immersed in an activation buffer (150 mM NaCl, 50 mM Tris-HCl (pH 7.5), 10 mM CaCl$_2$) at 37° C. for 18 hr to activate MMP-9, and then stained with CBB. The obtained MMP-9 band was converted to numerical values by a densitometer (ATTO. Ltd.).

The MMP-9 production inhibitory rate by the test substance was calculated by the following equation.

MMP-9 production inhibitory rate=100−100×{(test substance addition value−non-stimulation value)/(PMA stimulation value−non-stimulation value)}

The MMP-9 production inhibitory rates of the test substance at 10, 2, 0.4 and 0.08 μM were calculated, and IC$_{50}$ value of the each test substance was determined using an analysis soft (RegExcel).

The results are shown in the following.

TABLE 1

| test substance | IC$_{50}$ (μM) | test substance | IC$_{50}$ (μM) | test substance | IC$_{50}$ (μM) |
|---|---|---|---|---|---|
| Ex. 1 | 0.79 | Ex. 3 | 0.93 | Ex. 4 | 0.40 |
| Ex. 6 | 0.29 | Ex. 9 | 0.34 | Ex. 10 | 0.53 |
| Ex. 12 | 0.61 | Ex. 15 | 0.45 | Ex. 20 | 0.32 |
| Ex. 21 | 0.38 | Ex. 22 | 0.33 | Ex. 23 | 0.45 |
| Ex. 24 | 0.21 | Ex. 27 | 0.94 | Ex. 28 | 0.36 |
| Ex. 29 | 0.91 | Ex. 30 | 0.30 | Ex. 31 | 0.55 |
| Ex. 33 | 0.31 | Ex. 34 | 0.43 | Ex. 35 | 0.72 |
| Ex. 36 | 0.54 | Ex. 40 | 0.84 | Ex. 42 | 0.22 |
| Ex. 43 | 0.45 | Ex. 44 | 0.45 | Ex. 46 | 0.55 |
| Ex. 47 | 0.35 | Ex. 48 | 0.77 | Ex. 49 | 0.26 |
| Ex. 50 | 1.30 | Ex. 52 | 0.32 | Ex. 53 | 0.24 |
| Ex. 55 | 0.13 | Ex. 56 | 0.23 | Ex. 58 | 0.12 |
| Ex. 59 | 0.21 | Ex. 60 | 0.13 | Ex. 61 | 0.10 |
| Ex. 62 | 0.69 | Ex. 63 | 0.36 | Ex. 64 | 0.12 |
| Ex. 65 | 0.16 | Ex. 66 | 0.63 | Ex. 69 | 0.16 |
| Ex. 70 | 0.06 | Ex. 71 | 0.14 | Ex. 72 | 0.10 |
| Ex. 73 | 0.09 | Ex. 74 | 0.15 | Ex. 75 | 0.11 |
| Ex. 76 | 0.24 | Ex. 77 | 0.05 | Ex. 78 | 0.28 |
| Ex. 79 | 0.16 | Ex. 80 | 0.25 | Ex. 81 | 0.10 |
| Ex. 82 | 0.10 | Ex. 83 | 0.42 | Ex. 93 | 0.17 |
| Ex. 94 | 0.34 | Ex. 95 | 0.51 | Ex. 97 | 0.21 |
| Ex. 98 | 0.22 | Ex. 99 | 0.61 | Ex. 100 | 0.23 |
| Ex. 103 | 0.06 | Ex. 104 | 0.01 | Ex. 105 | 0.04 |
| Ex. 106 | 0.17 | Ex. 108 | 0.67 | Ex. 109 | 0.14 |
| Ex. 112 | 0.70 | Ex. 106 | 0.46 | Ex. 117 | 0.93 |
| Ex. 123 | 0.73 | Ex. 130 | 0.62 | Ex. 131 | 0.44 |
| Ex. 132 | 0.39 | Ex. 134 | 0.68 | Ex. 135 | 0.49 |
| Ex. 136 | 0.41 | Ex. 138 | 0.10 | Ex. 139 | 0.45 |
| Ex. 140 | 0.62 | Ex. 141 | 0.32 | Ex. 142 | 0.40 |
| Ex. 143 | 0.28 | Ex. 144 | 0.65 | | |

From the above results, it has been clarified that the compounds of the Examples of the present invention have an inhibitory effect of MMP-9 production and are assumed to show a superior antiangiogenic action.

INDUSTRIAL APPLICABILITY

According to the present invention, a novel indazole compound can be provided.

This application is based on a patent application No. 2004-35565 filed in Japan.

The invention claimed is:
1. An indazole compound represented by formula (I):

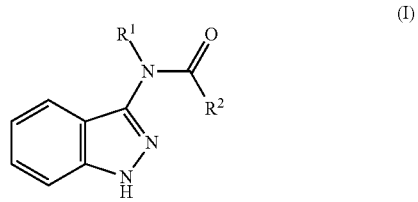

wherein
R$^1$ is a hydrogen atom, an optionally substituted alkyl, an optionally substituted phenyl or an optionally substituted aromatic heterocyclic ring, and
R$^2$ is a group of formula (II),

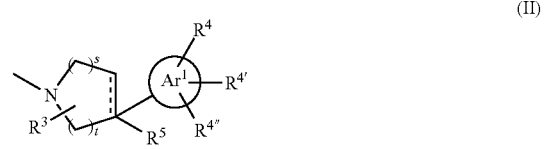

wherein
in the formula (II), ------
is a single bond or a double bond,
in the formula (II),
s is an integer of 1 or 2,
t is an integer of 1 or 2,
sum of s and t is 3,
$R^3$ is a hydrogen atom, a halogen atom, an optionally substituted alkyl, a hydroxyl, an alkoxy, a carboxy or an alkoxycarbonyl,
ring $Ar^1$ is an aryl or an aromatic heterocyclic ring,
$R^4$, $R^{4'}$, $R^{4''}$ are the same or different and each is a hydrogen atom, a halogen atom, an optionally substituted alkyl, an optionally substituted alkenyl, an optionally substituted alkynyl, a hydroxyl, an alkoxy, a carboxy, an alkoxycarbonyl, an acyl, —O(C=O)$R^{4a}$ (wherein $R^{4a}$ is an optionally substituted $C_{1-6}$ alkyl), —(C=O)$NR^{4a'}R^{4a''}$ (wherein $R^{4a'}$ and $R^{4a''}$ are the same or different and each is a hydrogen atom or an optionally substituted $C_{1-6}$ alkyl, or $R^{4a'}$ and $R^{4a''}$ are taken together to form an optionally substituted 5- to 7-membered non-aromatic heterocyclic ring), —NH(C=O)$R^{4a}$ (wherein $R^{4a}$ is an optionally substituted $C_{1-6}$ alkyl), —$SO_2NR^{4a'}R^{4a''}$ (wherein $R^{4a'}$ and $R^{4a''}$ are the same or different and each is a hydrogen atom or an optionally substituted $C_{1-6}$ alkyl, or $R^{4a'}$ and $R^{4a''}$ are taken together to form an optionally substituted 5- to 7-membered non-aromatic heterocyclic ring), —$NHSO_2R^{4a}$ (wherein $R^{4a}$ is an optionally substituted $C_{1-6}$ alkyl), an amino, an alkylamino, —$SR^{4a}$ (wherein $R^{4a}$ is an optionally substituted $C_{1-6}$ alkyl), —$SO_2R^{4a}$ is an optionally substituted $C_{1-6}$ alkyl), a cyano, an optionally substituted phenyl or an optionally substituted heterocyclic ring, or
$R^4$ and $R^{4'}$ are taken together to form an $C_{1-3}$ alkylenedioxy, and
$R^5$ is absent, or a hydrogen atom, a halogen atom, an optionally substituted alkyl, a hydroxyl, an alkoxy, an alkoxycarbonyl, an acyl, —(C=O)$NR^{5a}R^{5a'}$ (wherein $R^{5a}$ and $R^{5a'}$ are the same or different and each is a hydrogen atom or an optionally substituted $C_{1-6}$ alkyl), —NH(C=O)$R^{5a''}$ (wherein $R^{5a''}$ is an optionally substituted $C_{1-6}$ alkyl), an amino, an alkylamino, —$SR^{5a}$ (wherein $R^{5a}$ is a hydrogen atom or an optionally substituted $C_{1-6}$ alkyl) or a cyano, ------
or a pharmaceutically acceptable salt thereof.

2. The indazole compound of claim 1,
wherein, in the formula (I),
$R^2$ is a group of formula (II)

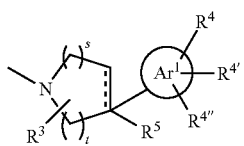

(II)

wherein
in the formula (II), ------
is a single bond or a double bond,
s is an integer of 1 or 2,
t is an integer of 1 or 2,
sum of s and t is 3,
$R^3$ is a hydrogen atom, a halogen atom, an optionally substituted alkyl, a carboxyl, an alkoxycarbonyl, a hydroxy or an alkoxy,
ring $Ar^1$ is a phenyl or an aromatic heterocyclic ring,
$R^4$, $R^{4'}$ and $R^{4''}$ are the same or different and each is a hydrogen atom, a halogen atom, an optionally substituted alkyl, an alkoxycarbonyl, a hydroxy, an alkoxy, a sulfonamide, a mercapto, a sulfinyl, a sulfonyl, an amino or an alkylamino, and
$R^5$ is absent, or a hydrogen atom, a halogen atom, an optionally substituted alkyl, a hydroxy, an alkoxy, an amino, an alkylamino, a sulfanyl or a cyano, ------
or a pharmaceutically acceptable salt thereof.

3. The indazole compound of claim 1,
wherein,
in the formula (I),
$R^1$ is a hydrogen atom or an optionally substituted alkyl,
in the formula (II), ------ is a single bond,
s is an integer of 1,
t is an integer of 2,
$R^3$ is a hydrogen atom,
ring $Ar^1$ is a phenyl or a thiophene,
$R^4$, $R^{4'}$, $R^{4''}$ are the same or different and each is a hydrogen atom, a halogen atom, an optionally substituted alkyl, a hydroxy, an alkoxy, —$SR^{4a}$ (wherein $R^{4a}$ is an optionally substituted $C_{1-6}$ alkyl) or an cyano, and
$R^5$ is a hydroxy or a cyano,
or a pharmaceutically acceptable salt thereof.

4. The indazole compound of claim 1,
wherein,
in the formula (I),
$R^1$ is a hydrogen atom,
in the formula (II), ------ is a single bond,
s is an integer of 1,
t is an integer of 2,
$R^3$ is a hydrogen atom,
ring $Ar^1$ is a phenyl,
$R^4$, $R^{4'}$, $R^{4''}$ are the same or different and each is a hydrogen atom, a halogen atom or an optionally substituted alkyl, and
$R^5$ is a hydroxy or a cyano
or a pharmaceutically acceptable salt thereof.

5. The indazole compound of claim 1,
wherein,
in the formula (I), ------ is a single bond,
$R^1$ is a hydrogen atom, and
in the formula (II),
s is an integer of 1,
t is an integer of 2,
$R^3$ is a hydrogen atom,
ring $Ar^1$ is a phenyl,
$R^4$, $R^{4'}$, $R^{4''}$ are the same or different and each is a hydrogen atom, a halogen atom or an optionally substituted alkyl, and
$R^5$ is a hydroxyl,
or a pharmaceutically acceptable salt thereof.

6. The indazole compound of claim 1, which is selected from
4-[4-chloro-3-(trifluoromethyl)phenyl]-4-hydroxy-1-piperidinecarboxylic acid (1H-indazol-3-yl)amide,
4-hydroxy-4-[3-(trifluoromethyl)phenyl]-1-piperidinecarboxylic acid (1H-indazol-3-yl)amide,
4-(4-chlorophenyl)-4-hydroxy-1-piperidinecarboxylic acid (1H-indazol-3-yl)amide,
4-[3-fluoro-5-(trifluoromethyl)phenyl]-4-hydroxy-1-piperidinecarboxylic acid (1H-indazol-3-yl)amide, 4-[4-fluoro-3-(trifluoromethyl)phenyl]-4-hydroxy-1-piperidinecarboxylic acid (1H-indazol-3-yl)amide,
4-hydroxy-4-[4-methyl-3-(trifluoromethyl)phenyl]-1-piperidinecarboxylic acid (1H-indazol-3-yl)amide,
4-(3,5-difluorophenyl)-4-hydroxy-1-piperidinecarboxylic acid (1H-indazol-3-yl)amide,
4-(3-chloro-4-fluorophenyl)-4-hydroxy-1-piperidinecarboxylic acid (1H-indazol-3-yl)amide,
4-(3-chloro-2-fluorophenyl)-4-hydroxy-1-piperidinecarboxylic acid (1H-indazol-3-yl)amide,
4-(3,4-dichlorophenyl)-4-hydroxy-1-piperidinecarboxylic acid (1H-indazol-3-yl)amide,
4-(3-chloro-5-fluorophenyl)-4-hydroxy-1-piperidinecarboxylic acid (1H-indazol-3-yl)amide,
4-(4-chloro-3-methylphenyl)-4-hydroxy-1-piperidinecarboxylic acid (1H-indazol-3-yl)amide,
4-(3-chlorophenyl)-4-hydroxy-1-piperidinecarboxylic acid (1H-indazol-3-yl)amide,
4-(1,3-benzodioxol-5-yl)-4-hydroxy-1-piperidinecarboxylic acid (1H-indazol-3-yl)amide,
4-hydroxy-4-(3-methylphenyl)-1-piperidinecarboxylic acid (1H-indazol-3-yl)amide,
4-(3-cyanophenyl)-4-hydroxy-1-piperidinecarboxylic acid (1H-indazol-3-yl)amide,
4-hydroxy-4-[3-(methylthio)phenyl]-1-piperidinecarboxylic acid (1H-indazol-3-yl)amide,
4-(3-ethylphenyl)-4-hydroxy-1-piperidinecarboxylic acid (1H-indazol-3-yl)amide,
4-(2,5-dichlorophenyl)-4-hydroxy-1-piperidinecarboxylic acid (1H-indazol-3-yl)amide,
4-[3,5-bis(trifluoromethyl)phenyl]-4-hydroxy-1-piperidinecarboxylic acid (1H-indazol-3-yl)amide,
4-[2-fluoro-5-(trifluoromethyl)phenyl]-4-hydroxy-1-piperidinecarboxylic acid (1H-indazol-3-yl)amide,
4-[2-chloro-5-(trifluoromethyl)phenyl]-4-hydroxy-1-piperidinecarboxylic acid (1H-indazol-3-yl)amide,
4-cyano-4-(2-methoxyphenyl)-1-piperidinecarboxylic acid (1H-indazol-3-yl)amide,
4-cyano-4-[3-(trifluoromethyl)phenyl]-1-piperidinecarboxylic acid (1H-indazol-3-yl)amide,
4-cyano-4-(2-fluorophenyl)-1-piperidinecarboxylic acid (1H-indazol-3-yl)amide,
4-[4-chloro-3-(trifluoromethyl)phenyl]-4-cyano-1-piperidinecarboxylic acid (1H-indazol-3-yl)amide,
4-(5-bromo-2-thienyl)-4-cyano-1-piperidinecarboxylic acid (1H-indazol-3-yl)amide,
4-cyano-4-(3,5-difluorophenyl)-1-piperidinecarboxylic acid (1H-indazol-3-yl)amide,
4-(4-bromo-2-chlorophenyl)-4-cyano-1-piperidinecarboxylic acid (1H-indazol-3-yl)amide,
4-phenyl-1,2,3,6-tetrahydropyridine-1-carboxylic acid (1H-indazol-3-yl)amide,
4-(4-fluorophenyl)-1,2,3,6-tetrahydropyridine-1-carboxylic acid (1H-indazol-3-yl)amide,
4-(2-fluorophenyl)-1,2,3,6-tetrahydropyridine-1-carboxylic acid (1H-indazol-3-yl)amide,
4-(3-chloro-4-fluorophenyl)-1,2,3,6-tetrahydropyridine-1-carboxylic acid (1H-indazol-3-yl)amide,
4-(3-fluorophenyl)-1,2,3,6-tetrahydropyridine-1-carboxylic acid (1H-indazol-3-yl)amide,
4-(2,3-difluorophenyl)-1,2,3,6-tetrahydropyridine-1-carboxylic acid (1H-indazol-3-yl)amide,
4-(5-chloro-2-thienyl)-1,2,3,6-tetrahydropyridine-1-carboxylic acid (1H-indazol-3-yl)amide,
4-(3-methyl-2-thienyl)-1,2,3,6-tetrahydropyridine-1-carboxylic acid (1H-indazol-3-yl)amide,
4-(2-thienyl)-1,2,3,6-tetrahydropyridine-1-carboxylic acid (1H-indazol-3-yl)amide,
4-[3-(trifluoromethyl)phenyl]-1,2,3,6-tetrahydropyridine-1-carboxylic acid (1H-indazol-3-yl)amide,
4-(3,4-dimethoxyphenyl)-1,2,3,6-tetrahydropyridine-1-carboxylic acid (1H-indazol-3-yl)amide,
4-[3-(dimethylamino)phenyl]-1,2,3,6-tetrahydropyridine-1-carboxylic acid (1H-indazol-3-yl)amide,
4-[3-(trifluoromethyl)phenyl]piperidine-1-carboxylic acid (1H-indazol-3-yl)amide,
4-[4-chloro-3-(trifluoromethyl)phenyl]-4-methoxypiperidine-1-carboxylic acid (1H-indazol-3-yl)amide,
4-[4-chloro-3-(trifluoromethyl)phenyl]-4-fluoropiperidine-1-carboxylic acid (1H-indazol-3-yl)amide,
4-(2-fluoro-5-methylphenyl)-4-hydroxy-1-piperidinecarboxylic acid (1H-indazol-3-yl)amide,
4-(3-chloro-2-methylphenyl)-4-hydroxy-1-piperidinecarboxylic acid (1H-indazol-3-yl)amide,
4-(3-chloro-4-methylphenyl)-4-hydroxy-1-piperidinecarboxylic acid (1H-indazol-3-yl)amide,
4-(3-fluoro-2-methylphenyl)-4-hydroxy-1-piperidinecarboxylic acid (1H-indazol-3-yl)amide,
4-(5-fluoro-2-methylphenyl)-4-hydroxy-1-piperidinecarboxylic acid (1H-indazol-3-yl)amide,
4-(4-fluoro-3-methylphenyl)-4-hydroxy-1-piperidinecarboxylic acid (1H-indazol-3-yl)amide,
4-(3-fluoro-5-methylphenyl)-4-hydroxy-1-piperidinecarboxylic acid (1H-indazol-3-yl)amide,
4-(2,5-dimethylphenyl)-4-hydroxy-1-piperidinecarboxylic acid (1H-indazol-3-yl)amide,
4-hydroxy-4-[2-methyl-3-(trifluoromethyl)phenyl]-1-piperidinecarboxylic acid (1H-indazol-3-yl)amide,
4-hydroxy-4-[2-methyl-5-(trifluoromethyl)phenyl]-1-piperidinecarboxylic acid (1H-indazol-3-yl)amide,
4-(3,4-dimethylphenyl)-4-hydroxy-1-piperidinecarboxylic acid (1H-indazol-3-yl)amide,
4-(3,5-dimethylphenyl)-4-hydroxy-1-piperidinecarboxylic acid (1H-indazol-3-yl)amide, and
4-(2,3-dimethylphenyl)-4-hydroxy-1-piperidinecarboxylic acid (1H-indazol-3-yl)amide,
or a pharmaceutically acceptable salt thereof.

7. The indazole compound of claim 1, which is 4-hydroxy-4-(3-methylphenyl)-1-piperidinecarboxylic acid (1H-indazol-3-yl)amide, or a pharmaceutically acceptable salt thereof.

8. The indazole compound of claim 1, which is 4-(3-chloro-2-fluorophenyl)-4-hydroxy-1-piperidinecarboxylic acid (1H-indazol-3-yl)amide, or a pharmaceutically acceptable salt thereof.

9. The indazole compound of claim 1, which is 4-(4-fluorophenyl)-1,2,3,6-tetrahydropyridine-1-carboxylic acid (1H-indazol-3-yl)amide, or a pharmaceuticallyacceptable salt thereof.

10. A pharmaceutical composition comprising a therapeutically effective amount of an indazole compound of claim 1 or a pharmaceutically acceptable salt thereof, and a pharmaceutically acceptable carrier.

11. The pharmaceutical composition of claim 10, wherein said composition is in a form suitable for oral administration selected from the group consisting of a tablet, a capsule, a powder, a liquid, and an elixir.

12. The pharmaceutical composition of claim 10, wherein said indazole compound of claim 1 or a pharmaceutically acceptable salt thereof is contained in an amount ranging from 5-95 wt % relative to the total weight of the pharmaceutical composition.

13. The pharmaceutical composition of claim 10, wherein said indazole compound of claim 1 or a pharmaceutically acceptable salt thereof is contained in an amount ranging from 5-90 wt % relative to the total weight of the pharmaceutical composition.

14. The pharmaceutical composition of claim 10, wherein said composition is in a foam suitable for parenteral administration.

15. The pharmaceutical composition of claim 14, wherein said indazole compound of claim 1 or a pharmaceutically acceptable salt thereof is contained in an amount ranging from 0.5-20% by weight relative to the total weight of the pharmaceutical composition.

16. The pharmaceutical composition of claim 14, wherein said indazole compound of claim 1 or a pharmaceutically acceptable salt thereof is contained in an amount ranging from 1-10% by weight relative to the total weight of the pharmaceutical composition.

* * * * *

UNITED STATES PATENT AND TRADEMARK OFFICE
CERTIFICATE OF CORRECTION

PATENT NO.        : 7,994,196 B2
APPLICATION NO.   : 10/589130
DATED             : August 9, 2011
INVENTOR(S)       : Akihiro Takemiya et al.

It is certified that error appears in the above-identified patent and that said Letters Patent is hereby corrected as shown below:

Column 111, lines 2-3:    "in the formula (II), ------- is a single bond or a double bond," should read --in the formula (II), ------- is a single bond or a double bond,--

Column 111, lines 63-64:  "in the formula (II), ------- is a single bond or a double bond," should read --in the formula (II), ------- is a single bond or a double bond,--

Column 115, line 7:       "foam" should read --form--

Signed and Sealed this
Eighth Day of November, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,994,196 B2 | Page 1 of 1 |
| APPLICATION NO. | : 10/589130 | |
| DATED | : August 9, 2011 | |
| INVENTOR(S) | : Akihiro Takemiya et al. | |

It is certified that error appears in the above-identified patent and that said Letters Patent is hereby corrected as shown below:

Column 111, line 46: delete " ----- "

Column 112, line 12: delete " ----- "

Signed and Sealed this
Ninth Day of October, 2012

David J. Kappos
*Director of the United States Patent and Trademark Office*